US007122517B2

(12) United States Patent
Hudson et al.

(10) Patent No.: US 7,122,517 B2
(45) Date of Patent: Oct. 17, 2006

(54) CRYSTALLIZED STRUCTURE OF TYPE IV COLLAGEN NC1 DOMAIN HEXAMER

(75) Inventors: Billy G. Hudson, Nashville, TN (US); Munirathinam Sundaramoorthy, Nashville, TN (US)

(73) Assignee: Kansas University Medical Center, Kansas City, KS (US)

( * ) Notice: Subject to any disclaimer, the term of this patent is extended or adjusted under 35 U.S.C. 154(b) by 618 days.

(21) Appl. No.: 10/206,699

(22) Filed: Jul. 26, 2002

(65) Prior Publication Data

US 2003/0100510 A1   May 29, 2003

Related U.S. Application Data

(60) Provisional application No. 60/385,362, filed on Jun. 3, 2002, provisional application No. 60/366,854, filed on Mar. 22, 2002, provisional application No. 60/351,289, filed on Oct. 29, 2001, provisional application No. 60/308,523, filed on Jul. 27, 2001.

(51) Int. Cl.
*A61K 38/00* (2006.01)
*A61K 38/08* (2006.01)
*A61K 38/10* (2006.01)

(52) U.S. Cl. .......................... 514/4; 530/326; 530/327; 530/328

(58) Field of Classification Search ................ 514/4; 530/326, 327, 328
See application file for complete search history.

(56) References Cited

FOREIGN PATENT DOCUMENTS

| WO | 96/00582 | 11/1996 |
|----|----------|---------|
| WO | 99/49885 | 7/1999 |
| WO | 00/59532 | 12/2000 |
| WO | 01/51523 | 7/2001 |
| WO | 03/012122 | 2/2003 |
| WO | 04/067762 | 8/2004 |

OTHER PUBLICATIONS

Johnson and Tracey, 'Peptide and Protein Drug Delivery', In: Encyclopedia of Controlled Drug Delivery, vol. 2, 1999, pp. 816-833.*
Maeshima Yohei, et al., (2001) JBC Papers in Press, "Extracellular matrix-derived peptide binds to αvβ3 integrin and inhibits angiogenesis", pp. 1-39. Aug., 2001.
Maeshima, Yohei, et al., (2001) The Journal of Biological Chemistry, "Identification of the anti-angiogenic site within vascular basement membrane-derived Tumstatin", vol.: 276(18), pp. 15240-15248.
Appelt, K. (1993) *Perspectives in Drug Discovery and Design*, "Crystal Structures of HIV-1 Protease Inhibitor Complexes," 1:23-48.
Bachinger, H.P. et al., (1980) *Eur. J. Biochem.*, "Folding Mechanism of the Triple Helix in Type-III Collagen and Type-III pN-Collagen," 106:619-632.
Barton, G. J. (1993) *Prot. Eng.*, "ALSCRIPT: A Tool To Format Multiple Sequence Alignments," 6:37-40.
Blumberg, B. et al., (1988) *J. Biol. Chem.*, "Drosophila Basement Membrane Procollagen α1 (IV)," 263(34):18328-18337.
Borza, D. B. et al. (2001) *J Biol. Chem.*, "The NC1 Domain of Collagen IV Encodes a Novel Network Composed of the α1, α2, α5, and α6 Chanins in Smooth Muscle Basement Membranes," 276(30):28532-28540.
Boute, N. et al. (1996) *Biol. Cell*, "Type IV Collagen in Sponges, the Missing Link in Basement Membrane Ubiquity," 88:37-44.
Boutaud, A. et al., (2000) *J. Biol. Chem.*, "Type IV Collagen of the Glomerular Basement Membrane," 275:30716-30724.
Brooks, P. C. et al., (1994) *Science*, "Requirement of Vascular Integrin α₁β₃ for Angiogenesis," 264:569-571.
Brooks. P. C. et al., (1997) *J. Clin. Invest.*, "Insulin-like Growth Factor Receptor Cooperates With Integrin αvβ5 to Promote Tumor Cell Dissemination in Vivo," 99:1390-1398.
Brooks, P. C. et al., (1998) *Cell*, "Disruption of Angiogenesis by PEX, a Noncatalytic Metalloproteinase Fragment with Integrin Binding Activity," 92:391-400.
Colorado, et al., (2000) Cancer Research, "Anti-Angiogenic Cues from Vascular Basement Membrane Collagen", vol.: 60, pp. 2520-2526.
Cosgrove, D. et al., (1996) *Genes & Dev.*, "Collagen COL4A3 Knockout: A Mouse Model for Autosomal Alport Sundrome," 10(23):2981-92.
Dion, A. S., and Myers, J. C. (1987) *J Mol. Biol.*, "COOH-terminal Propeptides of the Major Human Procollagens Structural, Functional and Genetic Comparisons," 193(1):127-43.
Dolz, R. et al., (1988) *Eur J Biochem.*, "Folding of Collagen IV," 178(2), 357-66.
Dvorak, H. F. et al., (1987) *Lab. Invest.*, "Fibrin Containing Gels Induce Angiogenesis," 57:673-686.
Exposito, J. Y. et al., (1993) *J Biol Chem.*, "Complete Primary Structure of a Sea Urchin Type IV Collagen α Chain and Analysis of the 5'End of Its Gene," 268(7):5249-54.

(Continued)

*Primary Examiner*—Karen A. Canella
(74) *Attorney, Agent, or Firm*—McDonnell Boehnen Hulbert & Berghoff LLP

(57) ABSTRACT

The present invention provides a crystallized NC1 domain hexamer of Type IV collagen, and methods for making the crystal, wherein the NC1 domain hexamer is crystallized such that the three dimensional structure of the crystallized NC1 domain hexamer can be determined to a resolution of at least 3 Å or better. The present invention also provides a method for designing compounds to inhibit angiogenesis, tumor growth, tumor metastasis, endothelial cell adhesion and/or proliferation, and/or basal lamina assembly, comprising analyzing the three dimensional structure of a crystallized Type IV collagen NC1 domain hexamer produced by the methods of the invention, and identifying and synthesizing compounds that target regions of the NC1 domain that have been identified by the analysis as being important for type IV collagen heterotrimer and hexamer assembly. The present invention also provides novel polypeptides designed by the rational drug design methods of the present invention, based on an analysis of the type TV collagen NC1 hexamer structure disclosed herein.

9 Claims, 11 Drawing Sheets

OTHER PUBLICATIONS

Fawzi, A., et al., (2000), "Cellular Signal, A Peptide of the α3(IV) Chain of Type IV Collagen Modulates Stimulated Neutrophil Function Via Activation of cAMP-dependent Protein Kinase and Ser/Thr Protein Phosphatase," 12:327-335.

Folkman, J. (1985) *Perspect, Biol. Med.*, "Toward an Understanding of Angiogenesis: Search and Discovery," 29:10-36.

Fowler, S. J., et al., (2000) *J Biol Chem.*, "Characterization of Hydra Type IV Collagen," 275(50):39589-99.

Gunwar, S., et al., (1998) *J. Biol. Chem.*, "Glomerular Basement Membrane," 273(15):8767-8775.

Gunwar, S. et al., (1991) *J. Biol. Chem.*, "Properties of the Collagenous Domain of the α3(IV) Chain, the Goodpastuyre Antigen, of Lens Basement Membrane Collagen," 266(21):14088-94.

Guo, X. D., and Kramer, J. M. (1989) *J. Biol. Chem.*, "The Two *Caenorhabditis Elegans* Basement Membrane (Type IV) Collagen Genes Are Located on Separate Chromosomes," 264(29):17574-82.

Guo, X. et al., (1991) *Nature*, "Embryonic Lethality Caused By Mutations In Basement Membrane Collagen of C. *elegans*" 349:707-709.

Han, J. et al., (1997) *Journal of Biological Chemistry*, "A Cell Binding Domain from the α3 Chain of Type IV Collagen Inhibits Proliferation of Melanoma Cells," 272:20395-20401.

Hellmark, et al., (1996), Clin Exp Immunol, Epitope Mapping of anti-glomerular basement membrane (GBM) antibodies with synthetic peptides, vol.: 105: pp. 504-510.

Hohenester, E. et al., (1998) *EMBO J.*, "Crystal Structure of the Angiogenesis Inhibitor Endostatin at 1.5 Å Resolution," 17:1656-1664.

Hudson, B. G. et al., (1993) *J. Biol. Chem.*, "Type IV Collagen: Structure, Gen Organization, and Role in Human Diseases," 268(35):26033-6.

Kashtan, C. E., and Michael, A. F. (1993) *Am. J. Kid. Dis.*, "Alport Syndrome: From Bedside to Genome to Bedside," 22:627-640.

Kashtan, C. E., and Michael, A. F. (1996) *Kidney Int.*, "Alport Syndrome: Perspectives in Clinical Nephrology," 50:1445-1463.

Kefalides, N. A. et al. (1999) *Medicina*, "Suppression of Tumor Cell Growth by Type IV Collagen and a Peptide from the NCI Domain of the α3 (IV) Chain," 59:553.

Koliakos, et al., (1989), The Journal of Biological Chemistry, "The Binding of Heparin to Type IV Collagen: Domain Specificity with Identification of Peptide Sequences from the alpha 1 (IV) and alpha2 (IV) which preferentially bind heparin", vol.: 264(4), pp. 2313-2323.

Lam, P. Y. S. et al., (1994) *Science*, "Rational Design of Potent, Bioavailable, Nonpeptide Cyclic Ureas as HIV Protease Inhibitors," 263:380-384.

Langeveld, J. P. M. et al., (1988) *J. Biol. Chem.*, "Structural Heterogeneity of the Noncollagenous Domain of Basement Membrane Collagen," 263(21):10481-8.

Laskowski, R. A. (1995) *J. Mol. Graph.*, "SURFNET: A Program for Visualization Molecular Surfaces, Cavities, and Intermolecular Interactions," 13:323-330.

Laskowski, R. A. et al., (1993) *J. Appl. Cryst.*, "PROCHECK: A Program to Check the Sterochemical Quality of Protein Structures," 26:283-291.

Lees, J. F. et al., (1997) *EMBO J.*, "Identification of the Molecular Recognition Sequence Which Determines the Type-specific Assembly of Procollagen," 16(5):908-916.

Luo, A. M. et al., (2002), J. Lab Clin. Med., "Synthetic Peptides of Goodpasture's Antigen In Antiglomerular Basement Membrane Nephritis in Rats," 139(5): 303-310.

Marneros, A.G., and Olsen, B. R. (2001), "Matrix Biol., The Role of Collagen-Derived Proteolytic Fragments in Angiogenesis," 20:337-345.

Maeshima, et al., (2001), The Journal of Biological Chemistry, "Extracellular Matrix-derived Peptide Binds to $α_vβ_3$ Integrin and Inhibits Angiogenesis", vol.: 276(34), pp. 31959-31968.

Maeshima, et al., (2000), The Journal of Biological Chemistry, "Distinct Antitumor Properties of a Type IV Collagen Domain Derived From Basement Membrane", vol.: 275(28), pp. 21340-21348.

Martin, G. R. et al., (1988) *Adv. Protein Chem.*, "Basement Membrane Proteins: Molecular Structure and Function," 39:1-50.

McLaughlin, S. H., and Bulleid, N. J. (1998) *Matrix Biology*, "Molecular Recognition in Procollagen Chain Assembly," 16:369-377.

Miner, J. H., and Sanes, J. R. (1996) *J. Cell Biol.*, "Molecular and Functional Defects in Kidneys of Mice Lacking Collagen α3(IV): Implications for Alport Syndrome," 135(5):1403-13.

Miner, J.H. and Sanes, J. R. (1999) *Kidney International*, "Renal Basement Membrane Components," 56:2016-2024.

Myllyharju, J., and Kivirikko, K. I. (2001) *Ann. Med.*, "Collagens and Collagen-related Diseases," 33:7-21.

Netzer, K. O. et al., (1998) *Protein Sci.*, "Comparative Analysis of the Noncollagenous NC1 Domain of Type IV Collagen: Identification of Structural Features Important for Assembly, Function, and Pathogenesis," 7(6), 1340-51.

Nicholls, A. et al., (1991) *Proteins*, "Protein Folding and Association: Insights From the Interfacial and Thermodynamic Properties of Hydrocarbons," 11:281-296.

Nicosia, R. F. et al., (1994) *Exp. Biology*, "Modulation of Angiogenesis in Vitro by Laminin-Entactin Complex," 164:197-206.

Peczon, B. D. et al., (1982) *Exp. Eye Res.*, "Probing the Subunit Structure of Cow Anterior Lens Capsule with the Detergent, Sodium Dodecyl Sulfate," 35:643-651.

Petitclerc, E., et al., (2000), *J. Biol. Chem.*, "New Functions for Non-Collagenous Domains of Human Collagen Type IV," 275(11):8051-8061.

Phelps, et al., (1996), The Journal of Biological Chemistry, "Direct Identification of Naturally Processed Autoantigen-derived Peptides Bound to HLA-DR15", vol.: 271 (31), pp. 18549-18553.

Phelps, et al., (1998), The Journal of Biological Chemistry, "Presentation of the Goodpasture Autoantigen to CD4 T Cells is Influenced more by Processing Constraints than by HLA Class II Peptide Binding Preferences", vol.: 273 (19), pp. 11440-11447.

Pihlajaniemi, T. (1996) in *Molecular Pathology and Genetics of Alport Syndrome* (Trygvasson, K., ed), "Molecular Properties of the Glomerular Basement Membrane," 117:46-79.

Prestayko, A. W. et al.,(1998) *Proceedings of the Annual Meeting of the American Association for Cancer Research*, "Type IV Collagen Domains Inhibit Adhesion and Migration of Tumor Cells and Block Angiogenesis," 39:45.

Prockop, D. J., and Kivirikko, K. I. (1995) *Ann. Rev. Biochem.*, "COLLAGENS: Molecular Biology, Diseases, and Potentials for Therapy," 64:403-34.

Rosenbloom, J. et al., (1976) *J. Biol. Chem.*, "Termination of Procollagen Chain Synthesis by Puromycin," 251:2070-2076.

Sarras M. P., Jr. et al., (1991) *Dev. Biol.*, "Extracellular Matrix (Mesoglea) of Hydra Vulgaris," 148:495-500.

Sarras M. P., Jr. et al. (1993) *Dev. Biol.*, "Extracellular Matrix (Mesoglea) of Hydra Vulgaris," 157:383-398.

Sasaki, T. et al., (2000) *J. Mol. Biol.*, "Endostatins Derived from Collagens XV and XVIII Differ in Structural and Binding Properties, Tissue Distribution and Anti-Angiogenic Activity," 301:1179-1190.

Schlunegger, M. P., Bennett, M. J., and Eisenberg, D. (1997) *Advances in Protein Science*"Oligomer Formation by 3D Domain Swapping: a Model for Protein Assembly and Misassembly" 50, 61-132.

Schofield, J. D. et al., (1974) *Biochemistry*, "Formation of Interchain Disulfide Bonds and Helical Structure during Biosynthesis of Procollagen by Embryonic Tendon Cells," 13:1801-1806.

Setty, S. et al., (1998) *Journal of Biological Chemistry*, "Interactions of Type IV Collagen and Its Domains with Human Mesangial Cells," 273:12244-12249.

Shahan, T.A., et al., (1999), "Connect. Tissue Res., Inhibition of Tumor Cell Proliferation by Type IV Collagen Requires Increased Levels of cAMP," 40(3):221-232.

Sibley, M. H. et al., (1993) *J. Cell Biol.*, "Genetic Identification, Sequence, and Alternative Splicing of the *Caenorhabditis Elegans* α2(IV) Collagen Gene," 123(1):255-64.

Sibley, M. H. et al., (1994) *EMBO J.*, "Mutations in the α2(IV) Basement Membrane Collagen Gene of *Caenorhabditis Elegans* Produce Phenotypes of Differing Severities," 13:3278-3285.

Siebold, B. et al., (1988) *Eur. J. Biochem.*, "The Arrangement of Intra- and Intermolecular Disulfide Bonds in the Carboxyterminal, Non-Collagenous Aggregation and Cross-Linking Domain of Basement-Membrane Type IV Collagen," 176(3):617-24.

Stubbs, M. et al., (1990) *J. Mol. Biol.*, "Crystals of the NC1 Domain of Human Type IV Collagen," 211:683-684.

Sundaramoorthy, et al., (2002) The Journal of Biological Chemistry, "Crystal Structure of NC1 Domains", vol.: 277(34), pp. 31142-31153.

Timpl, R. et al., (1985) *Ann. NY Acad. Sci.*, "Structure and Biology of the Globular Domain of Basement Membrane Type IV Collagen$^α$," 460:58-72.

Timpl, R. et al., (1981) *Eur. J. Biochem.*, "A Network Model for the Organization of Type IV Collagen Molecules in Basement Membranes," 120(2), 203-11.

Timpl, R., and Brown, J. C. (1996) *Bioessays*, "Supramolecular Assembly of Basement Membranes," 18(2):123-131.

Tzinia, A.K., et al., (2002), Experimental Cell Research, "Effects of Collagen IV on Neuroblastoma Cell Matrix-Related Functions," 274:169-177.

Uitto, V. J. et al., (1981) *Arch. Biochem. Biophys.*, "Synthesis of Type I Procollagen: Formation of Interchain Disulfide Bonds before Complete Hydroxylation of the Protein," 210:445-454.

Uitto, J., and Prockop, D. J. (1973) *Biochem. Biophys. Res. Commun.*, "Rate of Helix Formation by Intracellular Procollagen and Protocollagen. Evidence for a Role for Disulfide Bonds," 55:904-911.

Varner, J. A. et al., (1995) *Cell Adhesion and Communication*, "REVIEW: The Integrin $α_vβ_3$: Angiogenesis and Apoptosis," 3:367-374.

Weber, M. (1992) *Kidney International*, "Basement Membrane Proteins," 41:620-628.

Wlodawer, A., and Erickson, J. W. (1993) *Ann. Rev. Biochem.*, "Structure-Based Inhibitors of HIV-1 Protease," 62:543-585.

Zhang, X. et al., (1994) *Dev Biol.*, "Hydra Cell Aggregate Development is Blocked by Selective Fragments of Fibronectin and Type IV Collagen," 164(1):10-23.

Zhou, J. et al., (1994) *J. Biol. Chem.*, "Complete Primary Structure of the Sixth Chain of Human Basement Membrane Collagen, α6(IV)," 269:13193-13199.

\* cited by examiner

CRYSTALLIZED STRUCTURE OF TYPE IV COLLAGEN NC1 DOMAIN HEXAMER

CROSS REFERENCE

This application claims priority to U.S. Provisional Patent Application Ser. Nos. 60/308,523 filed Jul. 27, 2001; 60/351,289 filed Oct. 29, 2001; 60/366,854 filed Mar. 22, 2002; and 60/385,362 filed Jun. 3, 2002.

STATEMENT OF GOVERNMENT INTEREST

This work was supported by Grants DK18381 and DK53763 from the National Institutes of Health, and thus the U.S. government may have certain rights in the invention.

FIELD OF THE INVENTION

The present invention relates to the fields of crystallography, molecular biology, protein chemistry, angiogenesis, tumor growth and metastasis, and basement membrane assembly

BACKGROUND OF THE INVENTION

The basement membrane (basal lamina) is a sheet-like extracellular matrix (ECM), which is a basic component of all tissues. The basal lamina provides for the compartmentalization of tissues, and acts as a filter for substances traveling between tissue compartments. Typically the basal lamina is found closely associated with an epithelium or endothelium in all tissues of an animal, including blood vessels and capillaries. The basal lamina components are secreted by cells and then self assemble to form an intricate extra-cellular network. The formation of biologically active basal lamina is important to the development and differentiation of the associated cells.

Type IV collagen has been shown to be a major structural component of basement membranes, and consists of a family of six homologous α chains, designated α1(IV) through α6(IV). Each α chain is characterized by a non-collagenous (NC1) domain at the carboxyl terminus; a long, helical collagenous domain in the middle region; and a 7S collagenous domain at the amino terminus. (Martin, et. al., 1988, Adv. Protein Chem. 39:1–50; Gunwar, et. al. 1991, J. Biol. Chem. 266:14088–14094). Three α chains assemble into triple helical molecules, the "heterotrimer." The heterotrimer, once formed in the endoplasmic lumen, is secreted into the extracellular space, where two such heterotrimers assemble into a hexamer via C-terminal interactions, and then into a supramolecular network through N-terminal associations. The NC1 domains play the dominant role in this assembly, by determining the C-terminal dimeric association, leading to hexamer assembly.

The chain composition, and thus the properties of type IV collagen networks, are influenced by two factors. First, the chain composition of networks is limited by chain availability: the six α chains show a tissue-specific expression pattern, with the α1 and α2 chains being ubiquitous, and the α3–α6 chains having a more restricted tissue distribution. Second, the NC1 domain confers specificity to the chain-specific assembly of networks. Thus, as yet unidentified recognition sequences must exist within the NC1 domain that direct the selection of chains to form triple helical protomers, and that direct triple helical protomers to form hexamers and, thus, collagen networks. While numerous type IV collagen hexamers are theoretically possible that differ in kind and α chain stoichiometry, only three have been identified: $[\alpha1_2\alpha2]_2$, $[\alpha3\alpha4\alpha5]_2$, and $[(\alpha1_2\alpha2)(\alpha5_2\alpha6)]$.

Angiogenesis, the process of formation of new blood vessels, plays an important role in physiological processes such as embryonic and postnatal development, as well as in wound repair. Formation of blood vessels can also be induced by pathological processes involving inflammation (e.g., diabetic retinopathy and arthritis) or neoplasia (e.g., cancer) (Folkman, 1985, Perspect, Biol. Med., 29, 10). Neovascularization is regulated by angiogenic growth factors secreted by tumor or normal cells as well as by the composition of the extracellular matrix and the activity of endothelial enzymes (Nicosia and Ottinetti, 1990, Lab. Invest., 63, 115).

A common feature of all solid tumor growth is the requirement for a blood supply. Therefore, numerous laboratories have focused on developing anti-angiogenic compounds based on growth factors and their receptors. While this approach has led to some success, the number of growth factors known to play a role an angiogenesis is large. Therefore, the possibility exists that growth factor antagonists may have only limited use in treating cancer, since tumors and associated inflammatory cells likely produce a wide variety of factors that can induce angiogenesis.

In this regard, a strategy that targets a common feature of angiogenesis, such as endothelial cell adhesion to the extracellular matrix (ECM), might be expected to have a profound physiological impact on tumor growth in humans. This notion is supported by the fact that antagonists of specific ECM cell adhesion receptors such as $\alpha v \beta 3$ and $\alpha v \beta 5$ integrins can block angiogenesis. Furthermore, the $\alpha v \beta 3$ integrin is expressed most prominently on cytokine-activated endothelial and smooth muscle cells, and has been shown to be required for angiogenesis. (Varner et al., Cell Adhesion and Communication 3:367–374 (1995); Brooks et al., Science 264:569–571 (1994)). Based on these findings, a potentially powerful new approach to anti-angiogenic therapy is to specifically target critical regulatory domains within distinct ECM components.

Specific type IV collagen α(IV) NC1 domains have been demonstrated to be effective inhibitors of angiogenesis, tumor growth, tumor metastasis, cell binding to basement membranes, and assembly of Type IV collagen molecules (see, for example, U.S. Pat. Nos. 5,691,182; 5,856,184; 6,361,994; and 6,358,735). Despite the above, it would be of significant value to the art to identify further compounds capable of inhibiting these processes.

It is therefore highly desirable to provide a method of deducing the crystal structure of type IV collagen NC1 domains, and of providing a method of using this structure to design compounds that inhibit assembly of the type IV collagen heterotrimer and/or the type IV collagen hexamer.

SUMMARY OF THE INVENTION

In one aspect, the present invention provides a crystallized NC1 domain hexamer of Type IV collagen, and methods for making the crystal, wherein the NC1 domain hexamer is crystallized such that the three dimensional structure of the crystallized NC1 domain hexamer can be determined to a resolution of at least 3 Å or better.

In another aspect, the present invention provides a method for designing compounds to inhibit angiogenesis, tumor growth, tumor metastasis, endothelial cell adhesion and/or proliferation, and/or basal lamina assembly, comprising analyzing the three dimensional structure of a crystallized Type IV collagen NC1 domain hexamer produced by the methods of the invention, and identifying and synthesizing compounds that target regions of the NC1 domain that have been identified by the analysis as being important for type IV collagen heterotrimer and hexamer assembly. Such compounds can be used to inhibit angiogenesis, tumor growth, tumor metastasis, endothelial cell adhesion and/or proliferation, and basal lamina assembly.

In another aspect, the present invention provides novel polypeptides designed by the rational drug design methods of the present invention, based on an analysis of the type IV collagen NC1 hexamer structure disclosed herein. As a result of the information available from the crystal structure, it is possible to predict individual NC1 domain sequences that are critical for assembly of the type IV collagen heterotrimer and/or hexamer. Thus, it is also possible to design therapeutic polypeptides that will interfere with those interactions, and to inhibit assembly of the type IV collagen heterotrimer and/or the type IV collagen hexamer. Such therapeutic polypeptides can be used to inhibit or disrupt type IV collagen assembly, and thus are useful to inhibit angiogenesis, angiogenesis-mediated disorders, tumor growth, tumor metastasis, endothelial cell adhesion and/or proliferation, and basal lamina assembly.

BRIEF DESCRIPTION OF THE FIGURES

FIG. 1. Alignment of six human αNC1 chains grouped as α1-like (1, 3, & 5) and α2-like (2, 4, & 6) families. The cysteine pairs intrachain disulfides are labeled with identical numbers at the bottom. Six segments that form the trimer-trimer interface are boxed and three major segments at the monomer-monomer are highlighted with larger font size. The most important segments forming generic and specific interactions are identified at the bottom with darkly shaded bars, respectively.

DETAILED DESCRIPTION OF THE PREFERRED EMBODIMENTS

Figure 2A:
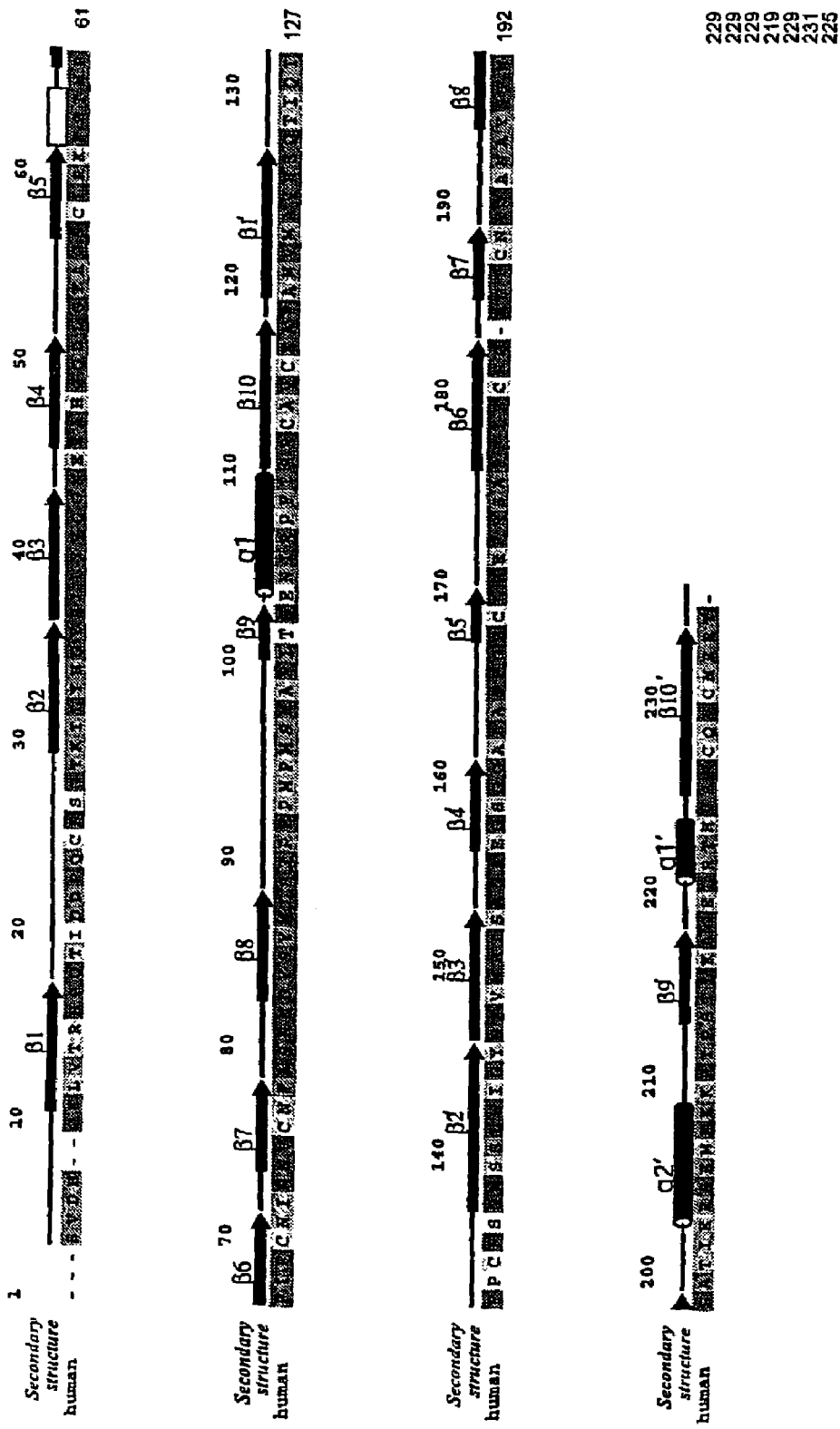
FIG. 2. (a) α1 chains and (b) α2 chains. Secondary structural elements are assigned based on the crystal structure. Both α1 and α2 structures contain β-strands β1–β10 and β1'–β10' and a $3_{10}$ helices g1 and g1'. The differences in secondary structures are a $3_{10}$ helix in α1 and β-stand βp' in α2 at the equivalent regions in the two sequences. The partner of βp' strand of α2 chain is in one of the two α1 chains. The corresponding region in α2 and the other α1 chains are extended structures. These regions marked by boxes. The secondary structures were from PROCHECK (61).

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), and *Gene Transfer and Expression Protocols*, pp. 109–128, ed. E. J. Murray, The Humana Press Inc., Clifton, N.J.).

Type IV collagens are synthesized and assembled as heterotrimers inside the cells, which are then secreted extracellularly where hexamer assembly, and subsequent basement membrane (basal lamina) assembly, occurs.

The present work has elucidated the structure of the type IV collagen $[(\alpha 1)_2(\alpha 2)]_2$ NC1 hexamer. Knowledge of this structure has utility in the design of compounds that can inhibit assembly of type IV collagen heterotrimers and hexamers, and thus are beneficial in the inhibition of angiogenesis, angiogenesis-mediated disorders, tumor growth, tumor metastasis, endothelial cell adhesion and/or proliferation, and basal lamina assembly.

Knowledge of the structure of the type IV collagen $[(\alpha 1)_2(\alpha 2)]_2$ NC1 hexamer structure provided by the present invention also has utility in the design of compounds that promote heterotrimer and hexamer assembly by providing tools and reagents for increasing the understanding of type IV collagen assembly, and thus also of basal lamina/basement membrane structure and function in general.

In one aspect, the present invention is directed to the three-dimensional structure of an isolated and purified type IV collagen $[(\alpha 1)_2(\alpha 2)]_2$ NC1 domain hexamer ("hexamer"), such that the three dimensional structure of the crystallized type IV collagen $[(\alpha 1)_2(\alpha 2)]_2$ NC1 hexamer can be determined to a resolution of 3.0 Å or better, preferably 2.2 Å or better, and most preferably 2.0 Å or better, and wherein the crystals are of space group P2$_1$, with an approximate a=129.41 Å; approximate b=143.87 Å; approximate c=162.92 Å; and approximate β=91.3° at room temperature and 4 hexamers in the asymmetric unit. Alternatively, the crystal has an approximate a=127.16 Å; approximate b=139.57 Å; approximate c=160.20 Å; and approximate β=91.3° and 4 hexamers in the asymmetric unit. In a further alternative, the crystals may have an approximate a=79.79 Å; approximate b=137.20 Å; approximate c=126.69 Å; and approximate β=90.30 at room temperature and 2 hexamers in the asymmetric unit.

In another aspect, the invention provides a method for crystallizing a type IV collagen $[(\alpha 1)_2(\alpha 2)]_2$ NC1 hexamer to a resolution of less than about 3.0 Å or better, preferably 2.2 Å or better, and most preferably 2.0 Å or better, wherein the type IV collagen $[(\alpha 1)_2(\alpha 2)]_2$ NC1 hexamer is present at a concentration of about 0.5 mg/ml to about 50 mg/ml, more preferably from about 1 mg/ml to about 15 mg/ml and most preferably about 10 mg/ml, and the crystallization takes place at 4° C. to 32° C., more preferably from 10° C. to 26° C., even more preferably at about 16° to 24° C., and even more preferably 20° C., to thereby obtain crystals of space group $P2_1$. The crystals may have an approximate a=129.41 Å; approximate b=143.87 Å; approximate c=162.92 Å; and approximate β=91.30 at room temperature and 4 hexamers in the asymmetric unit. Alternatively, cryocooling of the crystals may yield a crystal with an approximate a=127.16 Å; approximate b=139.57 Å; approximate c=160.20 Å; and approximate β=91.3° and 4 hexamers in the asymmetric unit. In a further alternative, the crystals may have an approximate a=79.79 Å; approximate b=137.20 Å; approximate c=126.69 Å; and approximate β=90.3° at room temperature and 2 hexamers in the asymmetric unit.

The crystallization, in one embodiment, may occur using hanging drops and the vapor diffusion method over 10% (w/v) PEG 20K. Alternatively, other crystallization methods may be used. For instance, a temperature variation may be used to produce crystals, or crystallization in space may be used to improve resolution. The crystallization, in another embodiment, may occur over 20% PEG 3350. In addition, other chemicals can be used in the place of PEG 20K or 3350. For instance, organic chemicals (e.g. isopropanol), inorganic chemicals (e.g. $(NH_4)_2SO_4$, $NaH_2PO_4$), and other molecular weight PEG may be used. Further details of the method are as described below.

In a further aspect, the present invention provides a method for determining the three dimensional structure of the crystallized type IV collagen $[(\alpha 1)_2(\alpha 2)]_2$ NC1 hexamer, comprising the steps of crystallizing the type IV collagen $[(\alpha 1)_2(\alpha 2)]_2$ NC1 hexamer as described above, and then analyzing the type IV collagen $[(\alpha 1)_2(\alpha 2)]_2$ NC1 hexamer to determine its three dimensional structure. In a preferred embodiment, the analyzing is by x-ray diffraction. Data sets generated from the diffraction analysis can be analyzed using any appropriate software, including but not limited to the DENZO and SCALEPACK programs of the HKL2000 suite (39), the SOLVE program (40), the RESOLVE (41) program, and/or the FFT program of CCP4 suite (42). Tracing of the polypeptides from the resulting analysis can be accomplished using any suitable software, including but not limited to the TOM FRODO graphics program (43). The final structure analysis can be accomplished using any appropriate software, including but not limited to SETOR (45), GRASP(46), and SURFNET(47) graphics software packages, various utility programs in the CCP4 suite, and HBPLUS(48) and protein-protein interaction web server (http://www.biochem.ucl.ac.uk/bsm/PP/server/).

By analyzing the three-dimensional structure of the type IV collagen $[(\alpha 1)_2(\alpha 2)]_2$ hexamer, one of skill in the art can determine the critical sites for type IV collagen NC1 domain heterotrimer and hexamer assembly, as described below.

Another aspect of the invention is to use the three-dimensional structure of the type IV collagen $[(\alpha 1)_2(\alpha 2)]_2$ hexamer to solve the three-dimensional structure of a different type IV collagen NC1 domain hexamer crystal, or crystal of a mutant, homologue or co-complex of type IV collagen NC1 domain hexamer.

A further aspect of this invention is to use the three-dimensional structure of type IV collagen $[(\alpha 1)_2(\alpha 2)]_2$ hexamer to design inhibitors of the assembly of heterotrimers and hexamers of type IV collagen, including the type IV collagen $[(\alpha 1)_2(\alpha 2)]_2$ NC1 hexamer. These inhibitors may be used as therapeutics to inhibit undesired angiogenesis, angiogenesis-mediated disorders, tumor growth, tumor metastasis, endothelial cell adhesion and/or proliferation, and basal lamina assembly. This embodiment comprises:

(a) obtaining crystals of an NC1 hexamer of type IV collagen, wherein the crystal comprises an $[(\alpha 1)_2.\alpha_2]_2$ NC1 hexamer of type IV collagen, wherein the crystal consists of space groups $P2_1$ with approximate a=between 127.16 Å and 129.41 Å, b=between 139.57 Å and 143.87 Å; c=between 160.20 Å and 162.92 Å; β=91.3°, such that the three-dimensional structure of the crystallized NC1 domain hexamer can be determined to a resolution of 3 Å or better;

(b) analyzing the three-dimensional structure of the crystallized NC1 domain hexamer of type IV collagen; and (c) designing a potential inhibitor of type IV collagen assembly that targets one or more regions of a type IV collagen NC1 α chain selected from the group consisting of:

(i) Inter-chain domain swapping region;
(ii) Intra-chain domain swapping region;
(iii) Specificity region;
(iv) Specificity region partner;
(v) Hexamer interface;
(vi) Monomer-monomer interface; and
(vii) Hypervariable region.

As used herein "target" or "targeting" refers to compounds that will interact with this region, via covalent or non-covalent means. The definitions of the various regions are discussed below.

As discussed above, the NC1 domains drive the selection process for type IV collagen chain assembly, and thus analysis of NC1 domain assembly correlates with type IV collagen assembly. Furthermore, given the high degree of homology of the different NC1 domains, analysis of the $[(\alpha 1)_2(\alpha 2)]_2$ NC1 hexamer crystal structure provides insights into the structure of other hexamer types, as well as inhibiters of such assembly.

As used herein, "inhibiting assembly of heterotrimers and hexamers of type IV collagen" means to inhibit initial assembly of such heterotrimers and/or hexamers, or to disrupt the assembly of already assembled heterotrimers and hexamers of type IV collagen NC1 domains. In a highly preferred embodiment, the therapeutic compounds identified herein inhibit the initial assembly of such heterotrimers and/or hexamers of type IV collagen NC1 domains.

The inhibitors can comprise peptides, or antibodies directed against peptides derived from the critical regions that would be expected to interfere with type IV collagen heterotrimer and/or hexamer assembly. Alternatively, small molecules that are identified based on their potential to inhibit such assembly. Electronic screening of large, structurally diverse compound libraries, such as the Available Chemical Directory (ACD) can identify new structural classes of such modulators that would be expected to interact with the identified critical regions. Additionally, knowledge of the type IV collagen $[(\alpha 1)_2(\alpha 2)]_2$ NC1 hexamer structure permits "de novo design" of compounds to inhibit assembly of any type IV collagen NC1 domain heterotrimers and/or hexamers.

Potential inhibitors can be examined in silico through the use of computer modeling, using a docking program such as GRAM, DOCK, or AUTODOCK [Dunbrack et al., 1997, supra]. These procedures can include computer fitting of candidate compounds to the type IV collagen $[(\alpha1)_2(\alpha2)]_2$ NC1 hexamer to predict how the shape and chemical structure of the candidate compound will interfere with assembly of the type IV collagen heterotrimer and/or hexamer. Computer programs can also be used to estimate the attraction, repulsion, and steric hindrance of the candidate compound to the relevant binding site on the type IV collagen $[(\alpha1)_2(\alpha2)]_2$ hexamer. Generally the tighter the fit (e.g., the lower the steric hindrance, and/or the greater the attractive force), the more potent the candidate compound will be, and the less likely that the candidate compound will induce significant side effects due to unwanted interactions with other proteins.

Potential small molecule inhibitors can be obtained, for example, by screening random peptide libraries produced, for example, in recombinant bacteriophage (Scott and Smith, Science, 249:386–390 (1990); Cwirla et al., Proc. Natl. Acad. Sci., 87:6378–6382 (1990); Devlin et al., Science, 249:404–406 (1990)), or a combinatorial chemical library. Candidate compounds selected in this manner can be systematically modified by computer modeling programs until one or more promising candidate compounds are identified. Such analysis has been shown to be effective, for example, in the development of HIV protease inhibitors (Lam et al., Science 263:380–384 (1994); Wlodawer et al., Ann. Rev. Biochem. 62:543–585 (1993); Appelt, Perspectives in Drug Discovery and Design 1:23–48 (1993); Erickson, Perspectives in Drug Discovery and Design 1:109–128 (1993)).

Such computer modeling allows the selection of a finite number of rational chemical modifications, as opposed to the countless number of essentially random chemical modifications that could be made. Thus, the use of the three-dimensional structure disclosed herein, in conjunction with computer modeling, enables rapid screening in silico, which dramatically increases screening speed and efficiency.

Once such candidate compounds are identified, they are chemically synthesized, and their biological activity is assayed, as discussed below. For those compounds that show activity, they can be complexed with the type IV collagen $[(\alpha1)_2(\alpha2)]_2$ NC1 hexamer crystal for further X-ray diffraction analysis to map the interactions of the compound with the crystal structure. The three-dimensional structure of the supplemental crystal can be determined by Molecular Replacement Analysis, which involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Using this approach, it is possible to use the structure of the type IV collagen $[(\alpha1)_2(\alpha2)]_2$ NC1 hexamer disclosed herein to solve the three-dimensional structures of any such type IV collagen hexamer or co-complex.

Functional Assays

Any assay that can be used to test the effect of the candidate compounds on the in vitro or in vivo assembly of type IV collagen heterotrimers and/or hexamers can be used to verify the efficacy of the candidate compounds identified by the methods of the invention. Furthermore, any assay that can be used to test the effect of the candidate compounds on angiogenesis, tumor growth, tumor metastasis, and endothelial cell adhesion and/or motility can be used to verify their inhibitory activity. Such assays include, but are not limited to, the following.

Assembly Assay

In one example, the methods employed are as described in Boutaud et al., JBC 275 (39):30716–30724 (2000). Native GBM hexamers are isolated by standard methods and dissociated by dilution (<50 µg/ml) into a solution of 50 mM formic acid buffered at pH 3.0 with Tris base. Under these conditions, complete dissociation to NC1 monomers and dimers occurs, as can be verified by HPLC or FPLC gel filtration. The absence of salt from the buffer is optimal for complete hexamer dissociation. Reassembly of the dissociated NC1 domains is performed by changing the buffer to Tris-buffered saline (50 mM Tris, pH 7.4, 150 mM NaCl) by repeated dilution-concentration cycles. After incubating the NC1 domains at a concentration of about 1 mg/ml for 24 hours at room temperature, in the presence or absence of the candidate compounds at a desired concentration(s), the reaction products are separated according to their molecular weights using gel filtration chromatography. Quantification of the relative amounts of the various species in the mixture is done by peak area analysis from the HPLC profiles.

Hexamer assembly from purified α1–α6 NC1 domains is carried out similarly.

In all experiments, the ratio of the NC1 domains in the association mixture is preferably kept at 1:1. The isolated NC1 hexamers can subsequently be analyzed for composition by immunoprecipitation followed by Western blotting; for overall appearance (size and shape) by electron microscopy; and for molecular weight by sedimentation equilibrium ultracentrifugation.

In Vitro Effect on Angiogenesis

With modifications, the procedures of Nicosia and Ottinetti, (1990, Lab. Invest., 63, 115) and Nicosia, et. al. (1994, Exp. Biology, 164, 197–206) are utilized for experiments designed to test the effect of the drug candidates on angiogenesis under in vitro conditions. The model has been used to study the effects of growth factors and extracellular matrix molecules on the angiogenic response, and employs aortic ring cultures in three-dimensional collagen gels under serum-free conditions.

Experiments are performed with 1–3 month old Swiss Webster male mice. Following anesthesia, the thoracic aorta is excised under aseptic conditions and transferred to sterile MCDB 131 sterile growth medium (Clonetics, San Diego, Calif.) containing antibiotics. Fat is dissected away from the aorta and approximately six to eight 1 mm thoracic segments are obtained from each specimen. Segments are transferred to 48 well tissue culture plates. The wells of these plates are layered with 100 microliters of Matrigel™ (EHS basement membrane, Collaborative Biomedical Products, Bedford, Mass.) prior to transfer of the aortic segments. The Matrigel™ is diluted 1:1 with MCDB 131 growth medium prior to use. The segments are centered in the wells and an additional 100 microliters of Matrigel™ is then placed over the specimens. The aortic segments are therefore embedded in the basement membrane matrix. Each well then receives 300 microliters of MCDB 131 growth medium. The plates are placed in an incubator maintained at 37° C. with 5% $CO_2$. Specimens are observed daily over a 7 day period. Newly growing microvessels are counted using an inverted phase microscope at various times during the culture period. To test for the effect of drug candidates on angiogenesis, the drug candidates are mixed with the Matrigel™ and with the MCDB 131 growth medium, and the growth of microvessels from the cultured tissue into the matrix is analyzed.

Subcutaneous Fibrin Implant Angiogenesis

The drug candidates are injected intravenously into rats containing fibrin implants surgically placed subcutaneously, a modified version of the method described by Dvorak et al. (Lab. Invest. 57(6):673–686 (1987)). For example, rats are given tail vein injections of either control, or various concentrations of the drug candidates. The implants are then removed at appropriate times, and directly analyzed using an inverted microscope. The analysis involved counting the number of blood vessels per implant that grow into the fibrin in the control and experimental group.

Chick Embryo CAM Angiogenesis Assay

Angiogenesis is induced in the CAMs of 10 day old chick embryos with bFGF as described (Brooks et al., Cell 92:391–400 (1998)). Twenty four hours later, the embryos are systemically treated with various concentrations of the drug candidates, in a total volume of 100 μl of sterile phosphate buffered saline (PBS). Two days later, the embryos are sacrificed and the filter discs and CAM tissues removed. Angiogenesis is quantitated by counting the number of angiogenic blood vessel branch points in the confined area of the filter disc. The Angiogenic Index is defined as the number of branch points from experimental treatment minus control treatment.

Chick Embryo Tumor Growth Assay

Briefly, single cell suspensions of distinct tumor types are applied to the CAM of 10 day old chick embryos. The tumors may include, for example, CS-1 Melanoma cells, HT1080 human fibrosarcoma cells, and Hep-3 human epidermoid carcinoma cells. The embryos are injected systemically with varying concentrations of the drug candidates 24 hours later. The embryos are allowed to incubate for a total of 7 days, at which time they are sacrificed. The resulting tumors are resected and wet weights determined compared to control.

Immobilized NC1 Domains Support Human Endothelial Cell Adhesion

In order for new blood vessels to form, endothelial cells must have the capacity to adhere and migrate through the ECM. Moreover, this endothelial cell-ECM interaction may facilitate signal transduction events required for new blood vessel formation. Therefore, the ability of drug candidates to support endothelial cell attachment can be assessed.

Microtiter plates are coated with varying amounts of the drug candidates, followed by incubation with 1% bovine serum albumin (BSA) to block non-specific interactions. Endothelial cells, such as human ECV304 cells, are then allowed to attach to the immobilized polypeptides for varying time periods Non-adherent cells are removed by washing and attached cells are quantified by measuring the optical density of crystal violet eluted from attached cells.

In vitro Endothelial Cell Migration

Invasive cellular processes, such as angiogenesis and tumor metastasis, also require cellular motility. Thus, the ability of the drug candidates to support human endothelial cell migration can be tested in vitro. These experiments are conducted essentially according to the methods in Brooks et al., J. Clin. Invest. 99:1390–1398 (1997).

In vivo Endothelial Cell Migration

The ability of the drug candidates to support human endothelial cell migration can be tested in vivo. For example, drug candidates can be tested in the metastatic Lewis lung mouse tumor model using a standard protocol which is considered to be a good model of both metastasis and angiogenesis of lung tumors. (See for example, Teicher et al., Anticancer Res. 18:2567–2573 (1998); Guibaud et al., Anticancer Drugs 8:276–282 (1997); Anderson et al., Cancer Res. 56:715–718 (1996)).

Drug candidates are administered intravenously once every 2 days for a desired number of doses starting one day after tumor inoculation. All animals are weighed twice a week throughout the study. Starting one day after the last treatment, 1 or more mice are periodically sacrificed from each control group to measure pulmonary tumor burden. The experiment is terminated when the lungs of control animals have sufficient tumor mass to provide meaningful evaluation. At that time, the lungs of all remaining animals are excised, weighed, and the number of tumor foci greater than 2 mm in diameter counted.

In another aspect, the present invention provides an inhibitor of type IV collagen assembly identified by any of the methods described above.

In another aspect, the present invention provides an inhibitor of one or more process selected from the group consisting of angiogenesis, tumor growth, tumor metastasis, endothelial cell adhesion, endothelial cell proliferation, and basal lamina assembly, identified by any of the methods described above.

In another aspect, the present invention provides novel polypeptides that can be used to inhibit or disrupt type IV collagen assembly, and thus are useful to inhibit angiogenesis, angiogenesis-mediated disorders, tumor growth, tumor metastasis, endothelial cell adhesion and/or proliferation, and basal lamina assembly.

The term "polypeptide" is used in its broadest sense to refer to a compound of two or more subunit amino acids, amino acid analogs, or peptidomimetics. The subunits are linked by peptide bonds. The polypeptides described herein may be chemically synthesized or recombinantly expressed.

Preferably, the polypeptides of the present invention are chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile Nα-amino protected 9-fluorenylmethoxycarbonyl (Fmoc) amino acids first described by Carpino and Han (1972, J. Org. Chem. 37:3403–3409). Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art.

Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers. The polypeptides of the invention may comprise D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine.

In addition, the polypeptides can have peptidomimetic bonds, such as ester bonds, to prepare peptides with novel properties. For example, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo.

As discussed above, type IV collagens are synthesized and assembled as heterotrimers inside the cells, which are then secreted extracellularly where hexamer assembly, and subsequent basement membrane assembly, occurs. The polypeptides disclosed herein can work intra-cellularly to prevent heterotrimer assembly, which also necessarily inhibits hexamer assembly, and provide the desired therapeutic result. Alternatively (or additionally), the polypeptides disclosed herein can work extracellularly, to inhibit hexamer assembly, and/or to disrupt assembled hexamers, providing the desired therapeutic result.

Such polypeptides can be selected based on their utility in inhibiting generic heterotrimer assembly (ie: not α chain specific); specific heterotrimer assembly (ie: αchain specific); generic hexamer assembly (ie: not α chain specific); and/or specific hexamer assembly (ie: not α chain specific). Without knowledge of the type IV collagen $[(\alpha 1)_2(\alpha 2)]_2$ NC1 hexamer structure described herein, the design of inhibitors with such desired properties would not be available to those skilled in the art.

The single letter abbreviation for amino acids is used herein; "norL" refers to nor leucine.

In one embodiment, the polypeptides consist of at least 8 contiguous amino acids of general formula I:

PF(R1)(R2)CN(R3)(R4)(R5)VC(R6)(R7)A (SEQ ID NO:1)

R1 is selected from the group consisting of L, M, A, V, norL, and I;

R2 is selected from the group consisting of F and Y;

R3 is selected from the group consisting of I, V, L, norL, A, and P;

R4 is selected from the group consisting of N, G, and H;

R5 is selected from the group consisting of N, D, Q, and E;

R6 is selected from the group consisting of N, Y, and H; and

R7 is selected from the group consisting of F and Y.

This general formula I is derived from a consensus sequences of type IV collagen NC1 α1–α6 domains at the inter-chain domain swapping region ("Inter-CDSR") that includes the β6–β7 strands in the crystal structure, as further described below. This region is involved in interchain interactions within the heterotrimer, and a substantial portion of the sequence is also present at the hexamer interface, and thus is involved in hexamer assembly/stabilization. As such, peptides of general formula I are useful for inhibiting appropriate interchain interactions, and thus for disrupting optimal heterotrimer and hexamer assembly.

In various further embodiments, the polypeptides consists of at least 9, 10, 11, 12, 13, or 14 amino acids of general formula I. In a preferred embodiment, the polypeptide consists of 14 amino acids of general formula I.

In a preferred embodiment, the polypeptides consist at least 8 contiguous amino acids of general formula II, with the further limitation that R2 is F; R4 is N; R5 is selected from the group consisting of N and D; R6 is N; and R7 is F. Polypeptides of this embodiment are derived from a consensus sequences of type IV collagen NC1 α1, α3, and α5 domains at the Inter-CDSR.

In a further preferred embodiment, the polypeptides consist at least 8 contiguous amino acids of general formula I, with the further limitation that R2 is Y; R3 is selected from the group consisting of P and I; R5 is selected from the group consisting of D, Q, and E; R6 is selected from the group consisting of Y and H; and R7 is Y. Polypeptides of this embodiment are derived from a consensus sequences of type IV collagen NC1 α2, α4, and α6 domains at the Inter-CDSR.

In a further preferred embodiment, the polypeptides according to formula 1 consist of at least 8 contiguous amino acids of a sequence selected from the group consisting of PFLFCNINNVCNFA (α1) (SEQ ID NO:2); PFLFCNVND-VCNFA (α3) (SEQ ID NO:3); PFMFCNINNVCNFA (α5) (SEQ ID NO:4); PFLYCNPGDVCYYA (α2) (SEQ ID NO:5); PFAYCNIHQVCHYA (α4) (SEQ ID NO:6); and PFIYCNINEVCHYA (α6) (SEQ ID NO:7). These sequences represent the Inter-CDSR sequences from the individual type IV collagen α1–α6 NC1 domains. In various further embodiments, the polypeptides consist of at least 9, 10, 11, 12, 13, or 14 amino acids of one of the recited sequences. In a preferred embodiment, the polypeptide consists of 14 amino acids of one of the recited sequences.

In another embodiment, the polypeptides of the present invention consist of at least 7 contiguous amino acids of general formula II:

PF(R1)EC(R2)G(R3)(R4)GTC(R5) (SEQ ID NO:8)

R1 is selected from the group consisting of L, A, V, norL, and I;

R2 is selected from the group consisting of H, N, Q, and S;

R3 is selected from the group consisting of G, R, A, or is absent;

R4 is selected from the group consisting of R and Q; and

R5 is selected from the group consisting of N and H.

This general formula is derived from a consensus sequences of type IV collagen NC1 α1–α6 domains at the intra-chain domain swapping region ("Intra-CDSR") that includes the β6'–β7' strands in the crystal structure, as further described below. This region is involved in monomer-monomer interactions within the heterotrimer, and a substantial portion of the sequence is also present at the hexamer interface, and thus is involved in hexamer assembly/stabilization. As such, peptides of this general formula are useful for inhibiting both heterotrimer and hexamer interactions of type IV collagen.

In various further embodiments, the polypeptides consists of at least 8, 9, 10, 11, 12, or 13 amino acids of general formula II. In a preferred embodiment, the polypeptide consists of 13 amino acids of general formula II.

In a preferred embodiment, the polypeptides consist at least 7 contiguous amino acids of general formula II, with the further limitation that R2 is H; R3 is R; R4 is G; and R5 is N. Polypeptides of this embodiment are derived from a consensus sequence of the intra-CDSR sequences of the type IV collagen (α1, α3, and α5 NC1 domains.

In a further preferred embodiment, the polypeptides consist at least 7 contiguous amino acids of general formula II, with the further limitation that R2 is selected from the group consisting of N, Q, and S; R3 is selected from the group consisting of G, R, and A; R4 is selected from the group consisting of R and Q; and R5 is H. Polypeptides of this embodiment are derived from a consensus sequence of the intra-CDSR sequences of the type IV collagen α2, α4, and α6 NC1 domains.

In a further embodiment, the polypeptides according to general formula II consist of at least 7 contiguous amino acids of a sequence selected from the group consisting of PFIECHGRGTCN (α1 and α5) (SEQ ID NO:9); PFLECHGRGTCN (α3) (SEQ ID NO:10); PFIECNGGRGTCH (α2) (SEQ ID NO:11); PFLECQGRQGTCH (α4) (SEQ ID NO:12); and PFIECSGARGTCH (α6) (SEQ ID NO:13). These sequences represent the Intra-CDSR sequences from the individual type IV collagen α1–α6 NC1 domains. In various further embodiments, the polypeptides of this embodiment consist of at least 8, 9, 10, 11, 12, or 13 amino acids of one of the recited sequences. In a most preferred embodiment, the polypeptides consist of 12 (α1, α3, α5) or 13 (α2, α4, α6) contiguous amino acids of any one the recited sequences.

In a further embodiment, the full length Intra-CDSR polypeptides (e.g.: SEQ ID NO: 9, 10, 11, 12, or 13) may optionally further include 0–5 amino acids at either or both the amino and carboxyl terminus that are derived from the same α chain, in order to provide appropriate secondary structural characteristics to the polypeptide for optimal inhibitory activity. Thus, the polypeptides of the invention derived from the Intra-CDSR sequence of the α1-like NC1 chains can thus be selected from the group consisting of at least 12, 13, 14, 15, 16, 17, 18, 19, 20, 21, or 22 amino acids of a sequence selected from the group consisting of:

```
                                          (SEQ ID NO:14)
α1:     (E)(F)(R)(S)(A)PFIECHGRGTCN(Y)(Y)(A)(N)(A);

(SEQ ID NO:15)
α3:     (E)(F)(R)(A)(S)PFLECHGRGTCN(Y)(Y)(S)(N)(S);
        and (SEQ ID NO:16)
α5:     (E)(F)(R)(S)(A)PFIECHGRGTCN(Y)(Y)(A)(N)(S);
``` wherein the residues in parenthesis are the flanking sequences of the Intra-CDSR.

Alternatively, the polypeptides of the invention derived from the Intra-CDSR sequence of the α2-like NC1 chains can thus be selected from the group consisting of at least 13, 14, 15, 16, 17, 18, 19, 20, 21, 22, or 23 amino acids of a sequence selected from the group consisting of:

```
                                          (SEQ ID NO:17)
α2:     (D)(F)(R)(A)(T)PFIECNGGRGTCH(Y)(Y)(A)(N)(K);

(SEQ ID NO:18)
α4:     (D)(F)(R)(A)(A)PFLECQGRQGTCH(F)(F)(A)(N)(K);
        and (SEQ ID NO:19)
α6:     (D)(F)(R)(A)(T)PFIECSGARGTCH(Y)(F)(A)(N)(K);
``` wherein the residues in parenthesis are the flanking sequences of the Intra-CDSR.

The Inter CDSR sequence, while widely separated in the linear sequence of a given type IV collagen NC1 domain from the Intra-CDSR sequence in the same α chain (separated by approximately 100 amino acids), is present in close spatial proximity (within approximately 2 amino acids) to the Inter-CDSR sequence in the same α chain based on the derived crystal structure data. Thus, in another embodiment, the present invention provides chimeric polypeptides comprising:

(a) one or more Inter-CDSR polypeptides of general formula I;

(b) one or more Intra-CDSR polypeptides of general formula II; and (c) a linker polypeptide between the Intra-CDSR polypeptide and the Inter-CDSR polypeptide consisting of between 0–20 amino acids.

In preferred embodiments, the Inter-CDSR and/or the Intra-CDSR portion of the chimeric polypeptides consists of 8, 9, 10, 11, 12, 13, or 14 amino acids of general formula I and 7, 8, 9, 10, 11, 12, 13 amino acids of general formula II, respectively. In various other preferred embodiments, the linker polypeptide consists of 0, 1, 2, 3, 4, 5, 6, 7, 8, 9, 10, 11, 12, 13, 14, 15, 16, 17, 18, 19, or 20 amino acids. The optimal length of the spacer depends, at least in part, on the length of the Inter-CDSR and Intra-CDSR, as well as the position of the sequences within the full length Inter-CDSR and Intra-CDSR used to create the chimera. For example, if a full length Inter-CDSR and a full length Intra-CDSR were used, then the spacer is preferably between 0–5 amino acids in length, more preferably between 1–4 amino acids in length, and most preferably 2–3 amino acids in length. Based on the teachings herein, it will be apparent to one of skill in the art to design further such chimeric polypeptides.

In a most preferred embodiment of these chimeric polypeptides, the Inter-CDSR polypeptide is selected from the group consisting of PFLFCNINNVCNFA (SEQ ID NO:2), PFLFCNVNDVCNFA (SEQ ID NO:3), PFMFCNINNVCNFA (SEQ ID NO:4), PFLYCNPGDVCYYA (SEQ ID NO:5), PFAYCNIHQVCHYA (SEQ ID NO:6), and PFIYCNINEVCHYA (SEQ ID NO:7); the Intra-CDSR polypeptide is selected from the group consisting of PFIECHGRGTCN (SEQ ID NO:9), PFLECHGRGTCN (SEQ ID NO:10), PFIECNGGRGTCH (SEQ ID NO:11), PFLECQGRQGTCH (SEQ ID NO:12), and PFIECSGARGTCH (SEQ ID NO:13); and the linker polypeptide is 1, 2, 3, 4, or 5 amino acids; most preferably 2 amino acids.

In another embodiment, the polypeptides of the present invention consist of a sequence of an amino acids of general formula III:

F(R1)T(R2) (SEQ ID NO:20)

wherein R1 is selected from the group consisting of S and T; and

R2 is selected from the group consisting of M and L.

This general formula III is derived from a consensus sequences of type IV collagen NC1 α1–α6 domains at the specificity region ("SR") between the β5–β6 strands in the crystal structure, as further described below. This region is involved in specific recognition between monomers, by recognizing the specificity region partner ("SRP") in the monomer with which the SR of a given α chain interacts As such, peptides of general formula III are useful for inhibiting both heterotrimer and hexamer interactions of type IV collagen.

In a further embodiment, the SR polypeptides are selected from the group consisting of FSTM (α1, α2, α6, and α6) (SEQ ID NO:21), FTTM (α3) (SEQ ID NO:22) and FTSL (α4) (SEQ ID NO:23).

In a further embodiment, the SR polypeptides (e.g.: SEQ ID NO:21, 22, and 23) may optionally further include 0–5 amino acids at either or both the amino and carboxyl terminus that are derived from the same α chain, in order to provide appropriate secondary structural characteristics to the polypeptide for optimal inhibitory activity. Thus, according to this embodiment, the polypeptides of the invention derived from the SR sequence of the NC1 α chains can be selected from the group consisting of:

α1 X1-FSTM-Z1, wherein X1 is 0, 1, 2, 3, 4, or 5 amino acids of the sequence SCLRK (SEQ ID NO: 24), and Z1 is 0, 1, 2, 3, 4, or 5 amino acids of the sequence PFLFC (SEQ ID NO: 25) (the full sequence would thus be SCLRKFST-MPFLFC) (SEQ ID NO: 26);

α3: X3-FTTM-Z3, wherein X3 is 0, 1, 2, 3, 4, or 5 amino acids of the sequence SCLQR (SEQ ID NO: 27), and Z3 is 0, 1, 2, 3, 4, or 5 amino acids of the sequence PFLFC(SEQ ID NO: 25) (the full sequence would thus be SCLQRFTT-MPFLFC) (SEQ ID NO:28);

α5: X5-FSTM-Z5, wherein X5 is 0, 1, 2, 3, 4, or 5 amino acids of the sequence SCLRR (SEQ ID NO: 29), and Z5 is 0, 1, 2, 3, 4, or 5 amino acids of the sequence PFMFC (SEQ ID NO: 30) (the full sequence would thus be SCLRRFST-MPFMFC) (SEQ ID NO: 31);

α2: X2-FSTM-Z2, wherein X2 is 0, 1, 2, 3, 4, or 5 amino acids of the sequence SCLAR (SEQ ID NO: 32), and Z2 is 0, 1, 2, 3, 4, or 5 amino acids of the sequence PFLYC (SEQ ID NO: 33) (the full sequence would thus be SCLARFST-MPFLYC) (SEQ ID NO: 34);

α4: X4-FSTL-Z4, wherein X4 is 0, 1, 2, 3, 4, or 5 amino acids of the sequence SCLPV (SEQ ID NO: 35), and Z4 is 0, 1, 2, 3, 4, or 5 amino acids of the sequence PFAYC (SEQ ID NO: 36) (the full sequence would thus be SCLPVFSTLP-FAYC) (SEQ ID NO: 37); and (α6: X6-FSTM-Z6, wherein X6 is 0, 1, 2, 3, 4, or 5 amino acids of the sequence SCLPR (SEQ ID NO: 38), and Z6 is 0, 1, 2, 3, 4, or 5 amino acids of the sequence PFIYC (SEQ ID NO: 39) (the full sequence would thus be SCLPRFST-MPFIYC) (SEQ ID NO: 40).

In another embodiment, the polypeptides of the invention consist of an amino acid sequence of general formula IV:

(R1)MF(R2)K (SEQ ID NO:41)

wherein R1 is selected from the group consisting of E, R, and D; and

R2 is selected from the group consisting of K, R, and S.

This general formula IV is derived from a consensus sequences of type IV collagen NC1 α1, α3, and α5 domains at the specificity region partner ("SRP") located between the β8' and β9' strands, as discussed in more detail below. This region is involved in specific recognition between monomers, by recognizing the specificity region ("SR") in the monomer with which the SRP of a given α chain interacts As such, peptides of general formula IV are useful for inhibiting both heterotrimer and hexamer interactions of type IV collagen.

In a preferred embodiment, the SRP polypeptides according to general formula IV are selected from the group consisting of EMFKK (α1) (SEQ ID NO:42), RMFRK (α3) (SEQ ID NO:43), and DMFSK (α5) (SEQ ID NO:44).

In a further preferred embodiment, the SRP polypeptides are selected from the group consisting of SFQ (SRP of α2) (SEQ ID NO:45); LQF (SRP of α4) (SEQ ID NO:46), and QQF (SRP of α6) (SEQ ID NO:47). These sequences represent the SRP of the type IV collagen α chain NC1 domains as indicated. This region in the α2 NC1 domain adopts an extended conformation and pairs with the extended structure (Phe57-Thr59) in the adjacent α1 chain to form a short parallel β sheet, which is the only parallel β-sheet in the entire structure, as further discussed below.

In a further embodiment, the SRP polypeptides (e.g.: SEQ ID NOS:42–47) may optionally further include 0–5 amino acids at either or both the amino and carboxyl terminus that are derived from the same α chain, in order to provide appropriate secondary structural characteristics to the polypeptide for optimal inhibitory activity. The SRP-containing polypeptides of this embodiment of the invention can thus be selected from the group consisting of:

α1 X1-EMFKK-Z1, wherein X1 is 0, 1, 2, 3, 4, or 5 amino acids of the sequence TIERS (SEQ ID NO: 48), and wherein Z1 is 0, 1, 2, 3, 4, or 5 amino acids of the sequence PTPST (SEQ ID NO: 49) (the full length sequence would thus be TIERSEMFKKPTPST) (SEQ ID NO: 50);

α3: X3-RMFRK-Z3, wherein X3 is 0, 1, 2, 3, 4, or 5 amino acids of the sequence SLNPE (SEQ ID NO: 51), and wherein Z3 is 0, 1, 2, 3, 4, or 5 amino acids of the sequence PIPST (SEQ ID NO: 52) (the full length sequence would thus be SLNPERMFRKPIPST) (SEQ ID NO:53);

α5: X5-DMFSK-Z5, wherein X5 is 0, 1, 2, 3, 4, or 5 amino acids of the sequence TVDVS (SEQ ID NO: 54), and wherein Z5 is 0, 1, 2, 3, 4, or 5 amino acids of the sequence PQSET (SEQ ID NO: 55) (the full length sequence would thus be TVDVSDMFSKPQSET) (SEQ ID NO: 56);

α2: X2-SFQ-Z2, wherein X2 is 0, 1, 2, 3, 4, or 5 amino acids of the sequence TIPEQ (SEQ ID NO: 57), and wherein Z2 is 0, 1, 2, 3, 4, or 5 amino acids of the sequence GSPSA (SEQ ID NO: 58) (the full length sequence would thus be TIPEQSFQGSPSA) (SEQ ID NO: 59);

α4: X4-LQF-Z4, wherein X4 is 0, 1, 2, 3, 4, or 5 amino acids of the sequence TVKAD (SEQ ID NO: 60), and wherein Z4 is 0, 1, 2, 3, 4, or 5 amino acids of the sequence SSAPA (SEQ ID NO: 61) (the full length sequence would thus be TVKADLQFSSAPA) (SEQ ID NO: 62); and α6: X6-QQF-Z6, wherein X6 is 0, 1, 2, 3, 4, or 5 amino acids of the sequence TVEER (SEQ ID NO: 63), and wherein Z6 is 0, 1, 2, 3, 4, or 5 amino acids of the sequence GELPV (SEQ ID NO: 64) (the full length sequence would thus be TVEERQQFGELPV) (SEQ ID NO: 65).

In another embodiment, the polypeptides of the invention consist of an amino acid sequence of general formula V:

(R1)AH(R2)QD (SEQ ID NO:66)

wherein R1 is selected from the group consisting of R and K; and

R2 is selected from the group consisting of G and N.

This general formula V is derived from a consensus sequences of type IV collagen NC1 domain β-barrel-like core at the β4 strand, as discussed in more detail below. This region is involved in generic monomer-monomer interactions. As such, peptides of general formula V are useful for inhibiting both heterotrimer and hexamer interactions of type IV collagen.

In a preferred embodiment, the polypeptides according to general formula V are selected from the group consisting of RAHGQD (α1, α3, α5) (SEQ ID NO:67) and KAHNQD (α2,α4, α6) (SEQ ID NO:68).

In a further preferred embodiment, the β-barrel polypeptides according to general formula V (e.g.: SEQ ID NOS: 67–68) may optionally further include 0–5 amino acids at either or both the amino and carboxyl terminus that are derived from the same α chain, in order to provide appropriate secondary structural characteristics to the polypeptide for optimal inhibitory activity. The β-barrel-containing polypeptides of this embodiment of the invention can thus be selected from the group consisting of:

α1 X1-RAHGQD-Z1, wherein X1 is 0, 1, 2, 3, 4, or 5 amino acids of the sequence VQGNE (SEQ ID NO: 69), and wherein Z1 is 0, 1, 2, 3, 4, or 5 amino acids of the sequence LGTAG (SEQ ID NO: 70) (the full length sequence would thus be VQGNERAHGQDDLGTA) (SEQ ID NO: 71);

3: X3-RAHGQD-Z3, wherein X3 is 0, 1, 2, 3, 4, or 5 amino acids of the sequence VQGNQ (SEQ ID NO: 72), and wherein Z3 is 0, 1, 2, 3, 4, or 5 amino acids of the sequence LGTLG (SEQ ID NO: 73) (the full length sequence would thus be VQGNQRAHGQDLGTLG) (SEQ ID NO: 74);

α5: X5-RAHGQD-Z5, wherein X5 is 0, 1, 2, 3, 4, or 5 amino acids of the sequence VQGNK (SEQ ID NO: 75), and wherein Z5 is 0, 1, 2, 3, 4, or 5 amino acids of the sequence LGTAG (SEQ ID NO: 70) (the full length sequence would thus be VQGNKRAHGQDLGTAG (SEQ ID NO: 76);

α2: X2-KAHNQD-Z2, wherein X2 is 0, 1, 2, 3, 4, or 5 amino acids of the sequence FEGQE (SEQ ID NO: 77), and wherein Z2 is 0, 1, 2, 3, 4, or 5 amino acids of the sequence LGLAG (SEQ ID NO: 78) (the full length sequence would thus be FEGQEKAHNQDLGLAG) (SEQ ID NO: 79);

α4: X4-KAHNQD-Z4, wherein X4 is 0, 1, 2, 3, 4, or 5 amino acids of the sequence LEGQE (SEQ ID NO: 80), and wherein Z4 is 0, 1, 2, 3, 4, or 5 amino acids of the sequence LGLAG (SEQ ID NO: 78) (the full length sequence would thus be LEGQEKAHNQDLGLAG) (SEQ ID NO: 81); and α6: X6-KAHNQD-Z6, wherein X6 is 0, 1, 2, 3, 4, or 5 amino acids of the sequence VEGQE (SEQ ID NO: 82), and wherein Z6 is 0, 1, 2, 3, 4, or 5 amino acids of the sequence LGFAG (SEQ ID NO: 83) (the full length sequence would thus be VEGQEKAHNQDLGFAG) (SEQ ID NO: 84).

In another embodiment, the polypeptides of the invention consist of an amino acid sequence of general formula VI:

(R1)G(R2)GQ (SEQ ID NO:85)

wherein R1 is selected from the group consisting of E and Q; and

R2 is selected from the group consisting of S, T, and G.

This general formula VI is derived from a consensus sequences of type IV collagen NC1 domain β-barrel-like core at the β4' strand, as discussed in more detail below. This region is involved in generic monomer-monomer interactions. As such, peptides of general formula VI are useful for inhibiting both heterotrimer and hexamer interactions of type IV collagen.

In a preferred embodiment, the polypeptides according to general formula VI are selected from the group consisting of EGSGQ (α1, α5) (SEQ ID NO:86), EGTGQ (α3) (SEQ ID NO:87), EGGGQ (α2, α6) (SEQ ID NO:88) and QGGGQ (α4) (SEQ ID NO:89).

In a further embodiment, the β-barrel polypeptides according to general formula VI (e.g.: SEQ ID NOS:86–89) may optionally further include 0–5 amino acids at either or both the amino and carboxyl terminus that are derived from the same α chain, in order to provide appropriate secondary structural characteristics to the polypeptide for optimal inhibitory activity. The β-barrel-containing polypeptides of this embodiment of the invention can thus be selected from the group consisting of:

α1 and α5 X1-EGSGQ-Z1, wherein X1 is 0, 1, 2, 3, 4, or 5 amino acids of the sequence TSAGA (SEQ ID NO: 90), and wherein Z1 is 0, 1, 2, 3, 4, or 5 amino acids of the sequence ALASP (SEQ ID NO: 91) (the full length sequence would thus be TSAGAEGSGQALASP) (SEQ ID NO: 92);

α3: X3-EGTGQ-Z3, wherein X3 is 0, 1, 2, 3, 4, or 5 amino acids of the sequence TSAGS (SEQ ID NO: 93), and wherein Z3 is 0, 1, 2, 3, 4, or 5 amino acids of the sequence ALASP (SEQ ID NO: 91) (the full length sequence would thus be TSAGSEGTGQALASP) (SEQ ID NO:94);

α2: X2-EGGGQ-Z2, wherein X2 is 0, 1, 2, 3, 4, or 5 amino acids of the sequence TAAGD (SEQ ID NO: 95), and wherein Z2 is 0, 1, 2, 3, 4, or 5 amino acids of the sequence SLVSP (SEQ ID NO: 96) (the full length sequence would thus be TAAGDEGGGQSLVSP) (SEQ ID NO: 97);

α4: X4-QGGGQ-Z4, wherein X4 is 0, 1, 2, 3, 4, or 5 amino acids of the sequence TGAGD (SEQ ID NO: 98), and wherein Z4 is 0, 1, 2, 3, 4, or 5 amino acids of the sequence ALMSP (SEQ ID NO: 99) (the full length sequence would thus be TGAGDQGGGQALMSP) (SEQ ID NO: 100); and α6: X6-EGGGQ-Z6, wherein X6 is 0, 1, 2, 3, 4, or 5 amino acids of the sequence TAAGA (SEQ ID NO: 101), and wherein Z6 is 0, 1, 2, 3, 4, or 5 amino acids of the sequence SLVSP (SEQ ID NO: 96) (the full length sequence would thus be TAAGAEGGGQSLVSP) (SEQ ID NO: 102).

In another embodiment, the polypeptides comprise sequences present at the hexamer interface, as determined from the deduced crystal structure. Type IV collagens are synthesized and assembled as trimers inside the cells, which are then secreted extracellularly where hexamer assembly, and subsequent basement membrane assembly, occurs. Therapeutics, such as those disclosed herein, can work intra-cellularly to prevent trimer assembly, thus inhibiting hexamer assembly, thus providing the desired therapeutic result. Alternatively (or additionally), therapeutics can work extracellularly, which leaves trimer assembly uninhibited, but targets hexamer assembly.

As such, polypeptides from regions at the hexamer interface can be used to inhibit hexamer formation or disrupt hexamer formation. In this embodiment, the polypeptides of the invention consist of an amino acid sequence of general formula VII:

(R1)G(R2)(R3) (SEQ ID NO:103)

wherein R1 is selected from the group consisting of Q and E;

R2 is selected from the group consisting of N and Q; and

R3 is selected from the group consisting of E, Q, and K.

This general formula VII is derived from a consensus sequences of type IV collagen NC1 α1–α6 domains at the hexamer interface at the end of the β3 strand up to the beginning of the β4 strand, as discussed in more detail below. This region is present at the hexamer interface, and is involved in hexamer assembly and stabilization. As such, peptides of general formula VII are useful for inhibiting hexamer interactions of type IV collagen.

In a preferred embodiment, the polypeptides consist of general formula VII, with the further limitation that R1 is Q and R2 is N. In this embodiment, the formula is a consensus of the sequences present in the α1/α3/α5 NC1 domains for general formula VII. In a further preferred embodiment, the polypeptides according to general formula VII are selected from the group consisting of QGNE (α1) (SEQ ID NO:104), QGNQ (α3) (SEQ ID NO:105), and QGNK(α5) (SEQ ID NO:106)

In a further preferred embodiment, the polypeptides according to general formula VII consist of EGQE (SEQ ID NO:107), which is the sequence of the sequences present in the α2/α4/α6 NC1 domains in general formula VII.

In a further embodiment, the hexamer polypeptides selected from the group consisting of SEQ ID NOS:104–107 may optionally further include 0–5 amino acids at either or both the amino and carboxyl terminus that are derived from the same α chain, in order to provide appropriate secondary structural characteristics to the polypeptide for optimal inhibitory activity. Such polypeptides can thus be selected from the group consisting of:

α1: X1-QGNE-Z1, wherein X1 is 0, 1, 2, 3, 4, or 5 amino acids of the sequence SLLYV (SEQ ID NO: 108), and wherein Z1 is 0, 1, 2, 3, 4, or 5 amino acids of the sequence RAHGQ (SEQ ID NO: 109) (the full length sequence would thus be SLLYVQGNERAHGQ) (SEQ ID NO: 110);

α3: X3-QGNQ-Z3, wherein X3 is 0, 1, 2, 3, 4, or 5 amino acids of the sequence SFLFV (SEQ ID NO: 111), and wherein Z3 is 0, 1, 2, 3, 4, or 5 amino acids of the sequence RAHGQ (SEQ ID NO: 109) (the full length sequence would thus be SFLFVQGNQRAHGQ) (SEQ ID NO:112);

α5: X5-QGNK-Z5, wherein X5 is 0, 1, 2, 3, 4, or 5 amino acids of the sequence SLLYV (SEQ ID NO: 108), and wherein Z5 is 0, 1, 2, 3, 4, or 5 amino acids of the sequence RAHGQ (SEQ ID NO: 109) (the full length sequence would thus be SLLYVQGNKRAHGQ) (SEQ ID NO: 113);

α2: X2-EGQE-Z2, wherein X2 is 0, 1, 2, 3, 4, or 5 amino acids of the sequence SLLYF (SEQ ID NO:114), and wherein Z2 is 0, 1, 2, 3, 4, or 5 amino acids of the sequence KAHNQ (SEQ ID NO:115) (the full length sequence would thus be SLLYFEGQEKAHNQ) (SEQ ID NO: 116);

α4: X4-EGQE-Z4, wherein X4 is 0, 1, 2, 3, 4, or 5 amino acids of the sequence SLLYL (SEQ ID NO:117), and wherein Z4 is 0, 1, 2, 3, 4, or 5 amino acids of the sequence KAHNQ (SEQ ID NO:115) (the full length sequence would thus be SLLYLEGQEKAHNQ) (SEQ ID NO: 118); and α6: X6-EGQE-Z6, wherein X6 is 0, 1, 2, 3, 4, or 5 amino acids of the sequence SLLFV (SEQ ID NO:119), and wherein Z6 is 0, 1, 2, 3, 4, or 5 amino acids of the sequence KAHNQ (SEQ ID NO:115) (the full length sequence would thus be SLLFVEGQEKAHNQ) (SEQ ID NO: 120).

An especially preferred embodiment of these hexamer interface polypeptides according to general formula VII consists of 1 additional amino acid at both the amino and carboxy terminus of the α1–α6 hexamer peptides, as follows:

α4 VQGNER (SEQ ID NO: 121)
α3: VQGNQR (SEQ ID NO: 122)
α6: VQGNKR (SEQ ID NO: 123)
α2: FEGQEK (SEQ ID NO: 124)
α4: LEGQEK (SEQ ID NO: 125)
α6: VEGQEK (SEQ ID NO: 126)

In a further embodiment wherein the polypeptides comprise sequences present at the hexamer interface, as determined from the deduced crystal structure, the polypeptides of the invention consist of an amino acid sequence of general formula VIII:

M(R1)M(R2)P (SEQ ID NO:127)

wherein R1 is selected from the group consisting of S, N, or is absent; and

R2 is selected from the group consisting of A, Q, or is absent.

This general formula VIII is derived from a consensus sequences of type IV collagen NC1 α1–α6 domains at the hexamer interface between the β8 and β9 strands, as discussed in more detail below. This region is present at the hexamer interface, and is involved in hexamer assembly and stabilization. As such, peptides of general formula VIII are useful for inhibiting hexamer interactions of type IV collagen.

In a preferred embodiment, the polypeptides of general formula VIII are selected from the group consisting of MSMAP (α1) (SEQ ID NO:128), MNMAP (α3) (SEQ ID NO:129), MSMQP (α5) (SEQ ID NO:130), and MMP (α2, α4, and α6) (SEQ ID NO: 131).

In a further preferred embodiment, the hexamer polypeptides selected from the group consisting of SEQ ID NOS: 128–131 may optionally further include 0–5 amino acids at either or both the amino and carboxyl terminus that are derived from the same α chain, in order to provide appropriate secondary structural characteristics to the polypeptide for optimal inhibitory activity. Such polypeptides can thus be selected from the group consisting of:

α1: X1-MSMAP-Z1, wherein X1 is 0, 1, 2, 3, 4, or 5 amino acids of the sequence PEPMP (SEQ ID NO: 132), and wherein Z1 is 0, 1, 2, 3, 4, or 5 amino acids of the sequence ITGEN (SEQ ID NO: 133) (the full length sequence would thus be PEPMPMSMAPITGEN) (SEQ ID NO: 134);

α3: X3-MNMAP-Z3, wherein X3 is 0, 1, 2, 3, 4, or 5 amino acids of the sequence PALMP (SEQ ID NO: 135), and wherein Z3 is 0, 1, 2, 3, 4, or 5 amino acids of the sequence ITGRA (SEQ ID NO: 136) (the full length sequence would thus be PALMPMNMAPITGRA) (SEQ ID NO:137);

α5: X5-MSMQP-Z5, wherein X5 is 0, 1, 2, 3, 4, or 5 amino acids of the sequence PEPMP (SEQ ID NO:132), and wherein Z5 is 0, 1, 2, 3, 4, or 5 amino acids of the sequence LKGQS (SEQ ID NO: 138) (the full length sequence would thus be PEPMPMSMQPLKGQS) (SEQ ID NO: 139);

α2: X2-MMP-Z2, wherein X2 is 0, 1, 2, 3, 4, or 5 amino acids of the sequence TAPLP (SEQ ID NO:140), and wherein Z2 is 0, 1, 2, 3, 4, or 5 amino acids of the sequence VAEDE (SEQ ID NO:141) (the full length sequence would thus be TAPLPMMPVAEDE) (SEQ ID NO: 142);

α4: X4-MMP-Z4, wherein X4 is 0, 1, 2, 3, 4, or 5 amino acids of the sequence AAPLP (SEQ ID NO:143), and wherein Z4 is 0, 1, 2, 3, 4, or 5 amino acids of the sequence LSEEA (SEQ ID NO:144) (the full length sequence would thus be AAPLPMMPLSEEA) (SEQ ID NO: 145); and α6: X6-MMP-Z6, wherein X6 is 0, 1, 2, 3, 4, or 5 amino acids of the sequence TAPIP (SEQ ID NO:146), and wherein Z6 is 0, 1, 2, 3, 4, or 5 amino acids of the sequence VSQTQ (SEQ ID NO:147) (the full length sequence would thus be TAPIPMMPVSQTQ) (SEQ ID NO: 148).

An especially preferred embodiment of these hexamer interface peptides according to general formula VIII consists of 3 additional amino acids at both the amino and carboxy terminus of the α1–α6 hexamer peptides, as follows:

α1 PMPMSMAPITG (SEQ ID NO: 149);
α3: LMPMNMAPITG (SEQ ID NO:150);
α5: PMPMSMQPLKG (SEQ ID NO: 151);
α2: PLPMMPVAE (SEQ ID NO: 152);
α4: PLPMMPLSE (SEQ ID NO: 153); and
α6: PTPMMPVSQ (SEQ ID NO: 154).

In a further embodiment wherein the polypeptides comprise sequences present at the hexamer interface, as determined from the deduced crystal structure, the polypeptides of the invention consist of an amino acid sequence of general formula IX:

AG(R1)(R2) (SEQ ID NO:155)

wherein R1 is selected from the group consisting of A, S and D; and

R2 is selected from the group consisting of E and Q.

This general formula IX is derived from a consensus sequences of type IV collagen NC1 α1–α6 domains between the β3' and β4' strands, as discussed in more detail below. This region is present at the hexamer interface, and is involved in hexamer assembly and stabilization. As such, peptides of general formula IX are useful for inhibiting hexamer interactions of type IV collagen.

In a preferred embodiment, the polypeptides of general formula IX are selected from the group consisting of AGAE (α1, α6, and α6) (SEQ ID NO:156), AGSE (α3) (SEQ ID NO:157), AGDE (α2) (SEQ ID NO:158), and AGDQ (α4) (SEQ ID NO:159).

In a further embodiment, the hexamer polypeptides selected from the group consisting of SEQ ID NOS:156–159 may optionally further include 0–5 amino acids at either or both the amino and carboxyl terminus that are derived from the same α chain, in order to provide appropriate secondary structural characteristics to the polypeptide for optimal inhibitory activity. Such polypeptides can thus be selected from the group consisting of:

α1: X1-AGAE-Z1, wherein X1 is 0, 1, 2, 3, 4, or 5 amino acids of the sequence VMHTS (SEQ ID NO: 160), and wherein Z1 is 0, 1, 2, 3, 4, or 5 amino acids of the sequence GSGQA (SEQ ID NO: 161) (the full length sequence would thus be VMHTSAGAEGSGQA) (SEQ ID NO: 162);

α3: X3-AGSE-Z3, wherein X3 is 0, 1, 2, 3, 4, or 5 amino acids of the sequence IMFTS (SEQ ID NO: 163), and wherein Z3 is 0, 1, 2, 3, 4, or 5 amino acids of the sequence GTGQA (SEQ ID NO: 164) (the full length sequence would thus be IMFTSAGSEGTGQA) (SEQ ID NO:165);

α5: X5-AGAE-Z5, wherein X5 is 0, 1, 2, 3, 4, or 5 amino acids of the sequence MMHTS (SEQ ID NO:166), and wherein Z5 is 0, 1, 2, 3, 4, or 5 amino acids of the sequence GSGQA (SEQ ID NO: 161) (the full length sequence would thus be MMHTSAGAEGSGQA) (SEQ ID NO: 167);

α2: X2-AGDE-Z2, wherein X2 is 0, 1, 2, 3, 4, or 5 amino acids of the sequence LMHTA (SEQ ID NO:168), and wherein Z2 is 0, 1, 2, 3, 4, or 5 amino acids of the sequence GGGQS (SEQ ID NO:169) (the full length sequence would thus be LMHTAAGDEGGGQS) (SEQ ID NO: 170);

α4: X4-AGDQ-Z4, wherein X4 is 0, 1, 2, 3, 4, or 5 amino acids of the sequence LMHTG (SEQ ID NO:171), and wherein Z4 is 0, 1, 2, 3, 4, or 5 amino acids of the sequence GGGQA (SEQ ID NO:172) (the full length sequence would thus be LMHTGAGDQGGGQA) (SEQ ID NO: 173); and α6: X6-AGAE-Z6, wherein X6 is 0, 1, 2, 3, 4, or 5 amino acids of the sequence LMHTA (SEQ ID NO:168), and wherein Z6 is 0, 1, 2, 3, 4, or 5 amino acids of the sequence GGGQS (SEQ ID NO:169) (the full length sequence would thus be LMHTAAGAEGGGQS) (SEQ ID NO: 174).

In a further embodiment wherein the polypeptides comprise sequences present at the hexamer interface, as determined from the deduced crystal structure, the polypeptides of the invention consist of at least 5 amino acids of the sequence of general formula X:

EC(R1)G(R2)(R3)GTC(R4)(R5)(R6) (SEQ ID NO:175)

wherein R1 is selected from the group consisting of H, N, Q, and S;

R2 is selected from the group consisting of G, R, A, or is absent;

R3 is selected from the group consisting of R and Q

R4 is selected from the group consisting of N and H;

R5 is selected from the group consisting of F and Y; and

R6 is selected from the group consisting of F and Y.

In various preferred embodiments, the polypeptide consists of at least 6, 7, 8, 9, 10, 11, or 12 amino acids of general formula X. In a preferred embodiment, the polypeptide consists of 12 amino acids of general formula X. This general formula X extensively overlaps with the Intra-CDSR, discussed above, and is present within the β6'–β7' strands, as discussed in more detail below. This region is present at the hexamer interface, and is involved in hexamer assembly and stabilization. As such, peptides of general formula X are useful for inhibiting hexamer interactions of type IV collagen.

In a further embodiment, the polypeptides are as described above for general formula X, with the exception that R2 is selected from the group consisting of G, R, A; and R4 is H. Polypeptides of this embodiment are derived from the consensus sequence of the α2/4/6 of general formula X.

In a further preferred embodiment, the polypeptides of general formula X are selected from the group consisting of ECHGRGTCNYY (α1/3/5) (SEQ ID NO:176), ECNGGRGTCHYY (α2) (SEQ ID NO:177), ECQGRQGTCHFF (α4) (SEQ ID NO:178), and ECSGARGTCHYF (α6) (SEQ ID NO:179).

In a further preferred embodiment, the polypeptides of the invention consist of an amino acid sequence of general formula XI:

(R1)(R2)T(R3)K (SEQ ID NO:180)

wherein R1 is selected from the group consisting of P, S, and A;

R2 is selected from the group consisting of S, E, and D; and

R3 is selected from the group consisting of L and V.

This general formula XI is present overlapping with the β9' strand in the crystal structure, as discussed in more detail below. This region is present at the hexamer interface, and is involved in hexamer assembly and stabilization. As such, peptides of general formula XI are useful for inhibiting hexamer interactions of type IV collagen.

In a preferred embodiment of general formula XI, R3 is L (as in α2/4/6/1/5). In a further preferred embodiment of general formula XI, R2 is selected from D and E (α2/4/5/6). In further preferred embodiments, the polypeptide according to general formula XI is selected from the group consisting of PSTLK (α1) (SEQ ID NO:181), PSTVK (α3) (SEQ ID NO:182), SETLK (α5 and α6) (SEQ ID NO:183), ADTLK (α2) (SEQ ID NO:184), and PDTLK (α4) (SEQ ID NO:185).

In a further embodiment, the hexamer polypeptides selected from the group consisting of SEQ ID NOS:181–185 may optionally further include 0–5 amino acids at either or both the amino and carboxyl terminus that are derived from the same α chain, in order to provide appropriate secondary structural characteristics to the polypeptide for optimal inhibitory activity. Such polypeptides can thus be selected from the group consisting of:

α1: X1-PSTLK-Z1, wherein X1 is 0, 1, 2, 3, 4, or 5 amino acids of the sequence FKKPT (SEQ ID NO: 186), and wherein Z1 is 0, 1, 2, 3, 4, or 5 amino acids of the sequence AGELR (SEQ ID NO: 187) (the full length sequence would thus be FKKPTPSTLKAGELR) (SEQ ID NO: 188);

α3: X3-PSTVK-Z3, wherein X3 is 0, 1, 2, 3, 4, or 5 amino acids of the sequence FRKPI (SEQ ID NO: 189), and wherein Z3 is 0, 1, 2, 3, 4, or 5 amino acids of the sequence AGELE (SEQ ID NO: 190) (the full length sequence would thus be FRKPEPSTVKAGELE) (SEQ ID NO:191);

α5: X5-SETLK-Z5, wherein X5 is 0, 1, 2, 3, 4, or 5 amino acids of the sequence FSKPQ (SEQ ID NO:192), and wherein Z5 is 0, 1, 2, 3, 4, or 5 amino acids of the sequence AGDLR (SEQ ID NO: 193) (the full length sequence would thus be FSKPQSETLKAGDLR) (SEQ ID NO: 194);

α2: X2-ADTLK-Z2, wherein X2 is 0, 1, 2, 3, 4, or 5 amino acids of the sequence QGSPS (SEQ ID NO:195), and wherein Z2 is 0, 1, 2, 3, 4, or 5 amino acids of the sequence AGLIR (SEQ ID NO:196) (the full length sequence would thus be QGSPSADTLKAGLIR) (SEQ ID NO: 197);

α4: X4-PDTLK-Z4, wherein X4 is 0, 1, 2, 3, 4, or 5 amino acids of the sequence SSAPA (SEQ ID NO:198), and wherein Z4 is 0, 1, 2, 3, 4, or 5 amino acids of the sequence ESQAQ (SEQ ID NO:199) (the full length sequence would thus be SSAPAPDTLKESQAQ) (SEQ ID NO: 200); and α6: X6-SETLK-Z6, wherein X6 is 0, 1, 2, 3, 4, or 5 amino acids of the sequence GELPV (SEQ ID NO: 201), and wherein Z6 is 0, 1, 2, 3, 4, or 5 amino acids of the sequence AGQLH (SEQ ID NO:202) (the full length sequence would thus be GELPVSETLKAGQLH) (SEQ ID NO: 203).

In a further preferred embodiment, the polypeptides of the invention consist of an amino acid sequence of general formula XII:

A(R1)RND (SEQ ID NO:204)

wherein R1 is selected from the group consisting of S, Q, and R.

This general formula XII is present in the highly conserved loop connecting the β7 and β8 strands in the crystal structure. This region is present at the hexamer interface, and is involved in hexamer assembly and stabilization. As such, peptides of general formula XII are useful for inhibiting hexamer interactions of type IV collagen.

In further preferred embodiments, the polypeptide according to general formula XII is selected from the group consisting of ASRND (α1, α3, α5, α2) (SEQ ID NO:205), AQRND (α4) (SEQ ID NO:206), and ARRND (α6) (SEQ ID NO:207).

In a further embodiment, the hexamer polypeptides selected from the group consisting of SEQ ID NOS:205, 206, and 207 may optionally further include 0–5 amino acids at either or both the amino and carboxyl terminus that are derived from the same α chain, in order to provide appropriate secondary structural characteristics to the polypeptide for optimal inhibitory activity. Such polypeptides can thus be selected from the group consisting of:

α1 and α5: X1-ASRND-Z1, wherein X1 is 0, 1, 2, 3, 4, or 5 amino acids of the sequence NVCNF (SEQ ID NO: 208), and wherein Z1 is 0, 1, 2, 3, 4, or 5 amino acids of the sequence YSYWL (SEQ ID NO: 209) (the full length sequence would thus be NVCNFASRNDYSYWL) (SEQ ID NO: 210);

α3: X3-ASRND-Z3, wherein X3 is 0, 1, 2, 3, 4, or 5 amino acids of the sequence DVCNF (SEQ ID NO: 211), and wherein Z3 is 0, 1, 2, 3, 4, or 5 amino acids of the sequence YSYWL (SEQ ID NO: 209) (the full length sequence would thus be DVCNFASRNDYSYWL) (SEQ ID NO:212);

α2: X2-ASRND-Z2, wherein X2 is 0, 1, 2, 3, 4, or 5 amino acids of the sequence DVCYY (SEQ ID NO:213), and wherein Z2 is 0, 1, 2, 3, 4, or 5 amino acids of the sequence KSYWL (SEQ ID NO:214) (the full length sequence would thus be DVCYYASRNDKSYWL) (SEQ ID NO: 215);

α4: X4-AQRND-Z4, wherein X4 is 0, 1, 2, 3, 4, or 5 amino acids of the sequence QVCHY (SEQ ID NO:216), and wherein Z4 is 0, 1, 2, 3, 4, or 5 amino acids of the sequence RSYWL (SEQ ID NO:217) (the full length sequence would thus be QVCHYAQRNDRSYWL) (SEQ ID NO: 218); and α6: X6-ARRND-Z6, wherein X6 is 0, 1, 2, 3, 4, or 5 amino acids of the sequence EVCHY (SEQ ID NO:219), and wherein Z6 is 0, 1, 2, 3, 4, or 5 amino acids of the sequence KSYWL (SEQ ID NO:214) (the full length sequence would thus be EVCHYARRNDKSYWL) (SEQ ID NO: 220).

In a further preferred embodiment, the polypeptides of the invention consist of an amino acid sequence of general formula XIII:

(R1)(R2)(R3)N(R4) (SEQ ID NO:221)

wherein R1 is selected from the group consisting of Y and F;

R2 is selected from the group consisting of Y and F;
R3 is selected from the group consisting of A and S; and
R4 is selected from the group consisting of A, S, and K.

This general formula XIII is present in the highly conserved loop connecting the β7' and β8' strands in the crystal structure. This region is present at the hexamer interface, and is involved in hexamer assembly and stabilization. As such, peptides of general formula XIII are useful for inhibiting hexamer interactions of type IV collagen.

In further preferred embodiments, the polypeptide according to general formula XIII is selected from the group consisting of YYANA (α1) (SEQ ID NO:222) YYSNS (α3) (SEQ ID NO:223) YYANS (α5) (SEQ ID NO:224) YYANK (α2) (SEQ ID NO:225) FFANK (α4) (SEQ ID NO:226) and YFANK(α6) (SEQ ID NO:227).

In a further embodiment, the hexamer polypeptides selected from the group consisting of SEQ ID NOS:222–227 may optionally further include 0–5 amino acids at either or both the amino and carboxyl terminus that are derived from the same α chain, in order to provide appropriate secondary structural characteristics to the polypeptide for optimal inhibitory activity. Such polypeptides can thus be selected from the group consisting of:

α1: X1-YYANA-Z1, wherein X1 is 0, 1, 2, 3, 4, or 5 amino acids of the sequence RGTCN (SEQ ID NO: 228), and wherein Z1 is 0, 1, 2, 3, 4, or 5 amino acids of the sequence YSFWL (SEQ ID NO: 229) (the full length sequence would thus be RGTCNYYANAYSFWL) (SEQ ID NO: 230);

α3: X3-YYSNS-Z3, wherein X3 is 0, 1, 2, 3, 4, or 5 amino acids of the sequence RGTCN (SEQ ID NO: 228), and wherein Z3 is 0, 1, 2, 3, 4, or 5 amino acids of the sequence YSFWL (SEQ ID NO: 229) (the full length sequence would thus be RGTCNYYSNSYSFWL) (SEQ ID NO:231);

α5: X1-YYANS-Z2, wherein X1 is 0, 1, 2, 3, 4, or 5 amino acids of the sequence RGTCN (SEQ ID NO: 228), and wherein Z5 is 0, 1, 2, 3, 4, or 5 amino acids of the sequence YSFWL (SEQ ID NO: 229) (the full length sequence would thus be RGTCNYYANSYSFWL) (SEQ ID NO: 232);

α2: X2-YYANK-Z2, wherein X2 is 0, 1, 2, 3, 4, or 5 amino acids of the sequence RGTCH (SEQ ID NO:233), and wherein Z2 is 0, 1, 2, 3, 4, or 5 amino acids of the sequence YSFWL (SEQ ID NO:229) (the full length sequence would thus be RGTCHYYANKYSFWL) (SEQ ID NO: 234);

α4: X4-FFANK-Z4, wherein X4 is 0, 1, 2, 3, 4, or 5 amino acids of the sequence QGTCH (SEQ ID NO:235), and wherein Z4 is 0, 1, 2, 3, 4, or 5 amino acids of the sequence YSFWL (SEQ ID NO:229) (the full length sequence would thus be QGTCHFFANKYSFWL) (SEQ ID NO: 236); and α6: X6-YFANK-Z6, wherein X6 is 0, 1, 2, 3, 4, or 5 amino acids of the sequence RGTCH (SEQ ID NO:233), and wherein Z6 is 0, 1, 2, 3, 4, or 5 amino acids of the sequence YSFWL (SEQ ID NO:229) (the full length sequence would thus be RGTCHYFANKYSFWL) (SEQ ID NO: 237).

In a further embodiment, the present invention provides novel polypeptides derived from the hypervariable region of the type IV collagen α chain NC1 domain sequences located between the β8' and the β9' strands, which are identified from the crystal structure as being present at the monomer-monomer interface, and which include the SRP and are involved in providing appropriate secondary structure for optimal interactions between the SR and the SRP. In this embodiment, the polypeptides consist of at least 7 amino acids of a sequence selected from the group consisting of IERSEMFKKPT (α1) (SEQ ID NO:238), LNPERMFRKPI (α3) (SEQ ID NO:239), VDVSDMFSKPQ (α5) (SEQ ID NO:240), IPEQSFQGSPS (α2) (SEQ ID NO:241), VKADLQFSSAPA (α4) (SEQ ID NO:242), and VEERQQFGELPV (α6) (SEQ ID NO:243). In various embodiments, the polypeptides consist of at least 8, 9, 10, 11, or 12 amino acids of a sequence selected from the group consisting of SEQ ID NO:235–240.

In a further embodiment, the polypeptides selected from the group consisting of SEQ ID NOS:238–243 may optionally further include 0–5 amino acids at either or both the amino and carboxyl terminus that are derived from the same α chain, in order to provide appropriate secondary structural characteristics to the polypeptide for optimal inhibitory activity. Such polypeptides can thus be selected from the group consisting of:

α1: X1-IERSEMFKKPT-Z1, wherein X1 is 0, 1, 2, 3, 4, or 5 amino acids of the sequence FWLAT (SEQ ID NO: 244), and wherein Z1 is 0, 1, 2, 3, 4, or 5 amino acids of the sequence PSTLK (SEQ ID NO: 181) (the full length sequence would thus be FWLATIERSEMFKKPTPSTLK) (SEQ ID NO: 245);

α3: X3-LNPERMFRKPI-Z3, wherein X3 is 0, 1, 2, 3, 4, or 5 amino acids of the sequence FWLAS (SEQ ID NO: 246), and wherein Z3 is 0, 1, 2, 3, 4, or 5 amino acids of the sequence PSTVK (SEQ ID NO: 182) (the full length sequence would thus be FWLASLNPERMFRKPIPSTVK) (SEQ ID NO:247);

α5: X1-VDVSDMFSKPQ-Z2, wherein X1 is 0, 1, 2, 3, 4, or 5 amino acids of the sequence FWLAT (SEQ ID NO: 244), and wherein Z5 is 0, 1, 2, 3, 4, or 5 amino acids of the sequence SETLK (SEQ ID NO: 183) (the full length sequence would thus be FWLATVDVSDMFSKPQSETLK) (SEQ ID NO: 248);

α2: X2-IPEQSFQGSPS-Z2, wherein X2 is 0, 1, 2, 3, 4, or 5 amino acids of the sequence FWLTT (SEQ ID NO:249), and wherein Z2 is 0, 1, 2, 3, 4, or 5 amino acids of the sequence ADTLK (SEQ ID NO:184) (the full length sequence would thus be FWLTTIPEQSFQGSPSADTLK) (SEQ ID NO: 250);

α4: X4-VKADLQFSSAPA-Z4, wherein X4 is 0, 1, 2, 3, 4, or 5 amino acids of the sequence FWLTT (SEQ ID NO:249), and wherein Z4 is 0, 1, 2, 3, 4, or 5 amino acids of the sequence PDTLK (SEQ ID NO:185) (the full length sequence would thus be FWLTTVKADLQFSSAPAPDTLK) (SEQ ID NO: 251); and α6: X6-VEERQQFGELPV-Z6, wherein X6 is 0, 1, 2, 3, 4, or 5 amino acids of the sequence FWLTT (SEQ ID NO:249), and wherein Z6 is 0, 1, 2, 3, 4, or 5 amino acids of the sequence SETLK (SEQ ID NO:183) (the full length sequence would thus be FWLTTVEERQQFGELPVSETLK) (SEQ ID NO: 252).

In further embodiments, the present invention provides other polypeptides that include multiple regions identified as being important for inhibiting monomer-monomer interactions (and thus heterotrimer assembly), and/or trimer-trimer interactions (and thus hexamer assembly). Polypeptides according to this aspect of the invention include the following:

SR plus the Inter-CDSR:
α1: FSTMPFLFCNINNVCNFA (SEQ ID NO: 253)
α3: FTTMPFLFCNVNDVCNFA (SEQ ID NO: 254)
α5: FSTMPFMFCNINNVCNFA (SEQ ID NO: 255)
α2: FSTMPFLYCNPGDVCYYA (SEQ ID NO: 256)
α4: FSTLPFAYCNIHQVCHYA (SEQ ID NO: 257)
α6: FSTMPFIYCNINEVCHYA (SEQ ID NO: 258)

Inter-CDSR plus contiguous hexamer interface region:
α1: PFLFCNINNVCNFASRND (SEQ ID NO: 259)
α3: PFLFCNVNDVCNFASRND (SEQ ID NO: 260)
α5: PFMFCNINNVCNFASRND (SEQ ID NO: 261)
α2: PFLYCNPGDVCYYASRND (SEQ ID NO: 262)
α4: PFAYCNIHQVCHYAQRND (SEQ ID NO: 263)
α6: PFIYCNINEVCHYARRND (SEQ ID NO: 264)

SR plus the Inter-CDSR plus contiguous hexamer interface region:

α1: FSTMPFLFCNINNVCNFASRND (SEQ ID NO: 265)
α3: FTTMPFLFCNVNDVCNFASRND (SEQ ID NO: 266)
α5: FSTMPFMFCNINNVCNFASRND (SEQ ID NO: 267)
α2: FSTMPFLYCNPGDVCYYASRND (SEQ ID NO: 268)
α4: FSTLPFAYCNIHQVCHYAQRND (SEQ ID NO: 269)
α6: FSTMPFIYCNINEVCHYARRND (SEQ ID NO: 270)

Intra-CDSR plus contiguous hexamer interface region:

α1 and α5: PFIECHGRGTCNYY (SEQ ID NO:271)
α3: PFLECHGRGTCNYY (SEQ ID NO: 272)
α2: PFIECNGGRGTCHYY (SEQ ID NO: 273)
α4: PFLECQGRQGTCHFF(SEQ ID NO: 274)
α6: PFIECSGARGTCHYF (SEQ ID NO: 275)

SRP/variable region plus contiguous hexamer interface:

α1: IERSEMFKKPTPSTLKAG (SEQ ID NO: 276)
α3: LNPERMFRKPIPSTVKAG (SEQ ID NO:277)
α5: VDVSDMFSKPQSETLKAG (SEQ ID NO: 278)
α2: IPEQSFQGSPSADTLKAG (SEQ ID NO: 279)
α4: VKADLQFSSAPAPDTLKES (SEQ ID NO: 280)
α6: VEERQQFGELPVSETLKAG (SEQ ID NO: 281)

Specific monomer-monomer inhibitor plus SR:

α1: GSCLRKFSTM (SEQ ID NO: 282)
α3: GSCLQRFTTM (SEQ ID NO:283)
α5: GSCLRRFSTM (SEQ ID NO: 284)
α2: GSCLARFSTM (SEQ ID NO: 285)
α4: GSCLPVFSTL (SEQ ID NO: 286)
α6: GSCLPRFSTM (SEQ ID NO: 287)

Monomer-monomer inhibitor plus SR plus Inter-CDSR plus hexamer interface

α1 LRKFSTMPFLFCNINNVCNF (SEQ ID NO: 288)
α3: LQRFTTMPFLFCNVNDVCNF (SEQ ID NO:289)
α5: LRRFSTMPFMFCNINNWCNF (SEQ ID NO: 290)
α2: LARFSTMPFLYCNPGDVCYY (SEQ ID NO: 291)
α4: LPVFSTLPFAYCNIHQVCHY (SEQ ID NO: 292)
α6: LPRFSTMPFIYCNINEVCHY (SEQ ID NO: 293)

In another aspect, the present invention provides methods for inhibiting angiogenesis, angiogenesis-mediated disorders, tumor growth, tumor metastasis, endothelial cell adhesion and/or proliferation, and basal lamina assembly, comprising administering to a subject in need thereof an amount effective to inhibit angiogenesis, angiogenesis-mediated disorders, tumor growth, tumor metastasis, endothelial cell adhesion and/or proliferation, and basal lamina assembly of one or more polypeptides of the invention, antibodies against such polypeptides, or pharmaceutical compositions thereof.

"Angiogenesis-mediated disorders" refers to diseases and conditions with accompanying undesired angiogenesis, including but not limited to solid and blood-borne tumors, diabetic retinopathy, rheumatoid arthritis, retinal neovascularization, choroidal neovascularization, macular degeneration, comeal neovascularization, retinopathy of prematurity, comeal graft rejection, neovascular glaucoma, retrolental fibroplasia, epidemic keratoconjunctivitis, Vitamin A deficiency, contact lens overwear, atopic keratitis, superior limbic keratitis, pterygium keratitis sicca, sogrens, acne rosacea, phylectenulosis, syphilis, Mycobacteria infections, lipid degeneration, chemical bums, bacterial ulcers, fungal ulcers, Herpes simplex infections, Herpes zoster infections, protozoan infections, Kaposi's sarcoma, Mooren ulcer, Terrien's marginal degeneration, marginal keratolysis, trauma, systemic lupus, polyarteritis, Wegeners sarcoidosis, scleritis, Steven's Johnson disease, radial keratotomy, sickle cell anemia, sarcoid, pseudoxanthoma elasticum, Pagets disease, vein occlusion, artery occlusion, carotid obstructive disease, chronic uveitis, chronic vitritis, Lyme's disease, Eales disease, Bechets disease, myopia, optic pits, Stargarts disease, pars planitis, chronic retinal detachment, hyperviscosity syndromes, toxoplasmosis, post-laser complications, abnormal proliferation of fibrovascular tissue, hemangiomas, Osler-Weber-Rendu, acquired immune deficiency syndrome, ocular neovascular disease, osteoarthritis, chronic inflammation, Crohn's disease, ulceritive colitis, psoriasis, atherosclerosis, and pemphigoid. (See U.S. Pat. No. 5,712,291)

The polypeptides, or antibodies against such polypeptides, may be subjected to conventional pharmaceutical operations such as sterilization and/or may contain conventional adjuvants, such as preservatives, stabilizers, wetting agents, emulsifiers, buffers etc.

For administration, the polypeptides, or antibodies against such polypeptides, are ordinarily combined with one or more adjuvants appropriate for the indicated route of administration. The polypeptides, or antibodies against such polypeptides, may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the polypeptides, or antibodies against such polypeptides of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

In practicing this aspect of the invention, the amount or dosage range of the polypeptides, antibodies against such polypeptides, or pharmaceutical compositions employed is one that effectively inhibits angiogenesis, angiogenesis-mediated disorders, tumor growth, tumor metastasis, and/or endothelial cell-extracellular matrix interactions. An inhibiting amount of the polypeptides that can be employed ranges generally between about 0.01 µg/kg body weight and about 10 mg/kg body weight, preferably ranging between about 0.05 µg/kg and about 5 mg/kg body weight.

The polypeptides, antibodies against such polypeptides, or pharmaceutical compositions thereof may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. In preferred embodiments, the polypeptides are administered intravenously or subcutaneously.

The polypeptides, antibodies against such polypeptides, or pharmaceutical compositions thereof may be made up in a solid form (including granules, powders or suppositories) or in a liquid form (e.g., solutions, suspensions, or emulsions). The polypeptides and antibodies against such polypeptides of the invention may be applied in a variety of solutions. Suitable solutions for use in accordance with the invention are sterile, dissolve sufficient amounts of the polypeptides, and are not harmful for the proposed application.

In a preferred embodiment, one or more of the disclosed polypeptides, antibodies against such polypeptides, or pharmaceutical compositions thereof, are used so as to target more than one region of type IV collagen for inhibition of assembly. For example, peptides that target different hexamer regions can be used in combination to increase their inhibitory effect. Alternatively, or additionally, combining a peptide targeting monomer-monomer interactions with a peptide that targets hexamer assembly can provide an additive inhibitory effect. Other combinations are well within the knowledge of one of skill in the art, based on the teachings herein.

EXAMPLES

Protein Purification and Crystallization. The $[(\alpha 1)_2.\alpha 2]_2$ NC1 hexamer was isolated from bovine eye lenses purchased from Pel-Freeze Biologicals (Rogers, Ark.) (37). Briefly, LBM was prepared by sonication of the lenses in the presence of 1 M NaCl and protease inhibitors (38). To cleave the NC1 domain from the full-length type IV collagen, the LBM preparation was digested with bacterial collagenase at 37° C. The NC1 hexamer was purified by using DE-52 and S-300 column chromatography.

Initial crystallization screening with commercial sparse matrix kits (Hampton Research, Laguna Niguel, Calif.) was carried out using concentrated protein (10 mg/ml) and hanging drop vapor diffusion method. LBM NC1 crystals grow as small clusters overnight in 10% (w/v) PEG 20K, 0.1 M Bicine buffer (pH 9.0) at room temperature. Diffraction quality crystals were grown using microseeding procedures under similar conditions with lower protein concentration. The crystals belong to monoclinic $P2_1$ space group with unit cell dimensions a=129.41 Å, b=143.87 Å, c=162.92 Å, and $\beta=91.30°$ at room temperature and four hexamers in the asymmetric unit. Cryocooling of the crystals in 25% 2,4-methyl pentanediol (MPD) or glycerol results in the shrinkage of the unit cell (a=127.16 Å, b=139.57 Å; c=160.20 Å; $\beta=91.30°$).

Structure Determination and Refinement. Initial heavy atom soaks were carried out at the crystallization pH and later switched to neutral pH with phosphate buffer. NC1 crystals soaked in synthetic mother liquor containing 2 mM $LuCl_3$ or $K_2PtCl_6$ transform the lattice to a smaller unit cell of dimensions a=79.79 Å, b=137.20 Å, c=126.69 Å, $\beta=90.3°$ and two hexamers in the asymmetric unit. The crystals were routinely transformed into new form by soaking in 2 mM $LuCl_3$ overnight and used for further heavy atom soakings. Multiwavelength anomalous diffraction (MAD) data sets were collected at peak, inflection and two remote wavelengths using a single crystal soaked in 0.5 M KBr for 1 min and flash-frozen in cold $N_2$ stream (Table 1). The heavy atom soak screens were carried out at beamlines 1–5 and 9–2 of Stanford Syncrhortron Radiation Laboratory (SSRL) and beamline X8C of National Synchrotron Light Source (NSLS) at Brookhaven National Laboratory. The Br-MAD data sets used in this study were collected at SSRL and processed using DENZO and SCALEPACK programs of HKL2000 suite (39). The $Br^-$ sites were located using SOLVE program (40) and 37 highest peaks (>6σ) were used for phasing the reflections at 2.2 Å resolution. The resulting phases were improved by solvent flattening using RESOLVE (41) and the electron density map was calculated using FFT program of CCP4 suite (42). Polypeptides of two α1 chains and one α2 chain (chains A–C) were traced using the TOM FRODO graphics program (43). The complete asymmetric unit was generated using non-crystallographic symmetry ("NCS") relations obtained from Br⁻ sites—first the second trimer (chains D–F) was generated to complete one hexamer and then the second hexamer (chains G–L) was generated from the first hexamer. The 2.0 Å data set collected at 0.8856 Å ($\lambda_4$) was used for model refinement using CNS program (44) and 5% of the data were set aside for monitoring $R_{free}$. The initial model was subjected to rigid body refinement using reflections in the 30.0–3.0 Å resolution range (R=0.361 and $R_{free}$=0.364) followed by simulated annealing refinement in the 10.0–2.5 Å resolution range (R=0.326 and $R_{free}$=0287). Resolution was slowly extended to 2.0 Å in several iterative cycles of model building and refinement of positional and thermal parameters. During the final rounds of refinement, solvent molecules (water and glycerol) and Br⁻ ions were added in steps using $2F_o–F_c$ and $F_o–F_c$ maps and hydrogen bonding criteria. Multiple conformers of a few sidechains were modeled in the final round. The structure was analyzed using SETOR(45), GRASP(46), and SURFNET(47) graphics software packages and various utility programs in CCP4 suite. The hexamer interface was analyzed using HBPLUS(48) and protein-protein interaction web server (http:/www.biochem.ucl.ac.uk/bsm/PP/server/).

TABLE 1

Summary of Crystallographic Analysis

Data Collection

| Dataset | Peak | Inflection | Remote 1 | Remote 2 |
|---|---|---|---|---|
| Wavelength (Å) | 0.9195 | 0.9197 | 0.9537 | 0.8856 |
| Resolution (Å) | 2.1 | 2.1 | 2.15 | 2.0 |
| Measured reflections | 602,172 | 603,309 | 568,640 | 686,286 |
| Unique reflections | 159,617 | 159,667 | 149,817 | 184,445 |
| Completeness (%)* | 98.3 (90.9) | 98.2 (90.5) | 98.7 (95.1) | 97.9 (87.8) |
| $R_{sym}$(%)† | 4.0 (7.7) | 3.0 (6.7) | 2.4 (4.9) | 3.4 (8.6) |
| I/σ(I) | 29.2 (15.0) | 33.0 (18.2) | 37.6 (26) | 30.5 (13.1) |

Phasing Statistics

| | |
|---|---|
| Resolution range (Å) | 50.0–2.2 |
| Number of Br sites | 33 |
| Overall Z-score | 127 |
| Figure of Merit SOLVE/RESOLVE | 0.67/0.76 |

Refinement Statistics

| | |
|---|---|
| Resolution range (Å) | 8.0–2.0 |
| Number of reflections (σ > 2) working/test | 166,448/8,789 |
| $R_{cryst}$/$R_{free}$ (%)‡ | 17.0/19.6 |
| RMS deviation Bond lengths (Å) | 0.0051 |
| Bond angles (°) | 1.29 |

*The overall completeness is given, with the completeness in the highest resolution shell shown in the parentheses. Similar convention in is followed for $R_{sym}$ and I/σ(I) also.
†$R_{sym} = \Sigma_h\Sigma_i |<I(h)> - I(h)_i| / \Sigma_h\Sigma_i I(h)_i|$.
‡5% of the data were excluded from refinement and were used to determine the $R_{free}$. The $R_{cryst}$ does not include these reflections. In both cases $R = \Sigma(|F_o| - k| F_c|)/\Sigma|F_o|$, with an appropriate choice of reflections for the summation.

Results and Discussion

Structure Determination and Overview. The bovine LBM NC1 hexamer, composed of α1 and α2 chains, crystallizes in monoclinic space group $P2_1$ (A-form) with four hexamers per asymmetric unit. This is different from the crystal forms reported for mouse EHS tumor NC1 (49) and human placenta NC1 hexamers (50), which crystallized with two hexamers and one hexamer in the asymmetric unit respectively. The intensity statistics of the preliminary diffraction data suggested the presence of pseudo-translation symmetry along the c axis in LBM NC1 crystals. An extensive search for heavy atom derivatives using soaking experiments was not successful. However, crystals soaked in $LuCl_3$ at pH 7.0 transformed the lattice to a smaller unit cell as a result of pseudo-translation symmetry becoming crystallographic translation in the same space group with only two hexamers in the asymmetric unit (B-form). MAD data of the crystals soaked in $LuCl_3$ did not provide useful phase information, probably due to a single weak binding site that was responsible for lattice transformation. However, we took advantage of the smaller unit cell for further heavy atom screening, including the newly suggested short-soaking strategy with halides (51,52). The $LuCl_3$-soaked B-form crystal structure was determined at 2.0 Å resolution by the MAD method using Br⁻ as the anomalous scatterer combined with solvent flattening. The data collection, phasing and refinement statistics are shown in Table 1.

The map was fitted with human NC1 α1 and α2 sequences (FIG. 2) since neither of the bovine sequences is available. Four each of the α1 and α2 sequences of other mammalian species are known, which share more than 95% sequence identity among them. More than 95% of the residues of the human sequences fit experimental electron density map. Differences between the human sequences and the map were found for residues Ile15Thr, Ser22Pro, Pro129Gln in α1 chain and Asp96Glu, Glu97Asp, and Gly176Ala in α2 chain. The sequences are numbered so that the residue after the last Gly-Xaa-Yaa repeat of the collagenous region is counted as the first residue in both α chains. The 12 chains in two hexamers have been assigned chain IDs A–L in the order of α1, α1 and α2 in each trimer. The map shows disorder for 5–6 residues at N- and two residues at C-termini of all the chains. The final model includes two hexamers, 36 Br⁻ ions, 48 glycerol molecules and 1139 water molecules. The final R-factor and $R_{free}$ of the refinement are 0.168 and 0.197 respectively. More than 90% of the residues are within the most favorable regions in Ramachandran map and Arg76 and Ser148 of the first α1 chain, Ser148 of the second α1 chain and Arg75, Glu95 and Ala145 of α2 chain in each trimer lie in the disallowed region. Only a handful of residues are in multiple conformations. The two hexamers in the asymmetric unit are similar with no apparent differences due to crystal contacts. The hexamer comprising chains A–F is used to describe the model.

Figure 3:
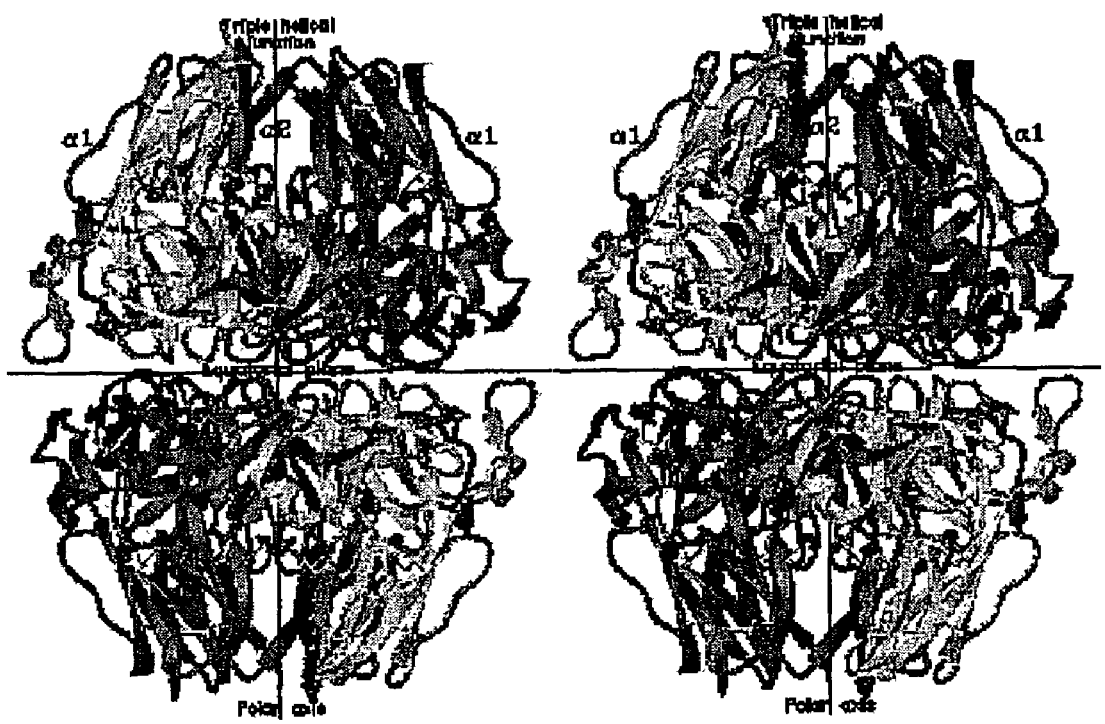
FIG. 3. Stereo diagram of deduced NC1 hexamer structure. The trimer-trimer interface ("Equatorial Plane"), collagen triple helical junction, and pseudo 3-fold axis or triple helix axis ("Polar Axis") are identified. The two trimers are related by a 2-fold NCS axis perpendicular to the polar axis and plane of the paper. This figure and FIGS. 5, 8, 9 and 10b were made using SETOR (45).

The overall structure of the hexamer is illustrated in FIG. 3. The two trimers in the hexamer are related by a 2-fold NCS axis at the interface ("equatorial plane") and the monomers within a trimer are related by a pseudo 3-fold symmetry coinciding with the triple helix axis ("polar axis").

Figure 1:
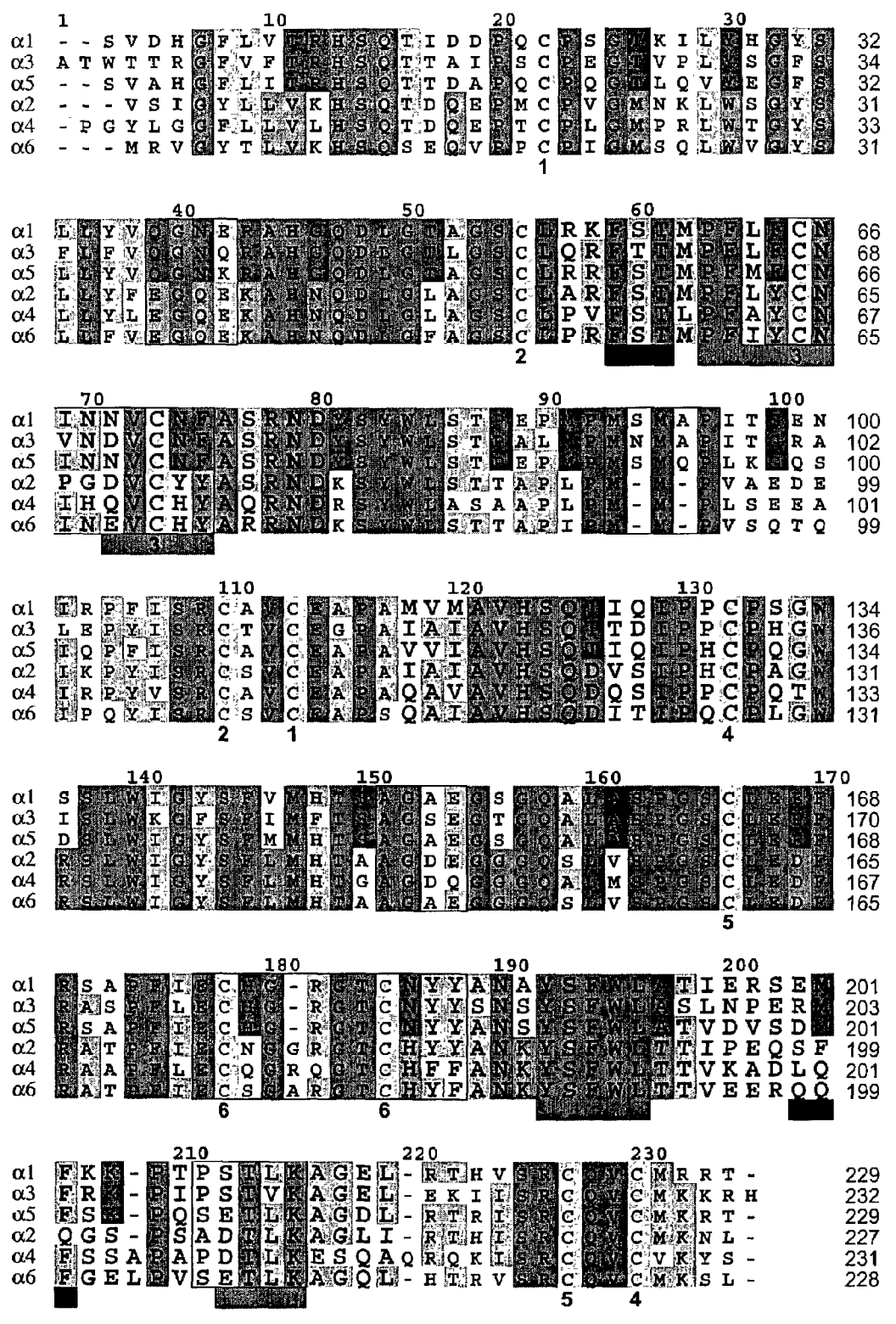
Figure 2B:
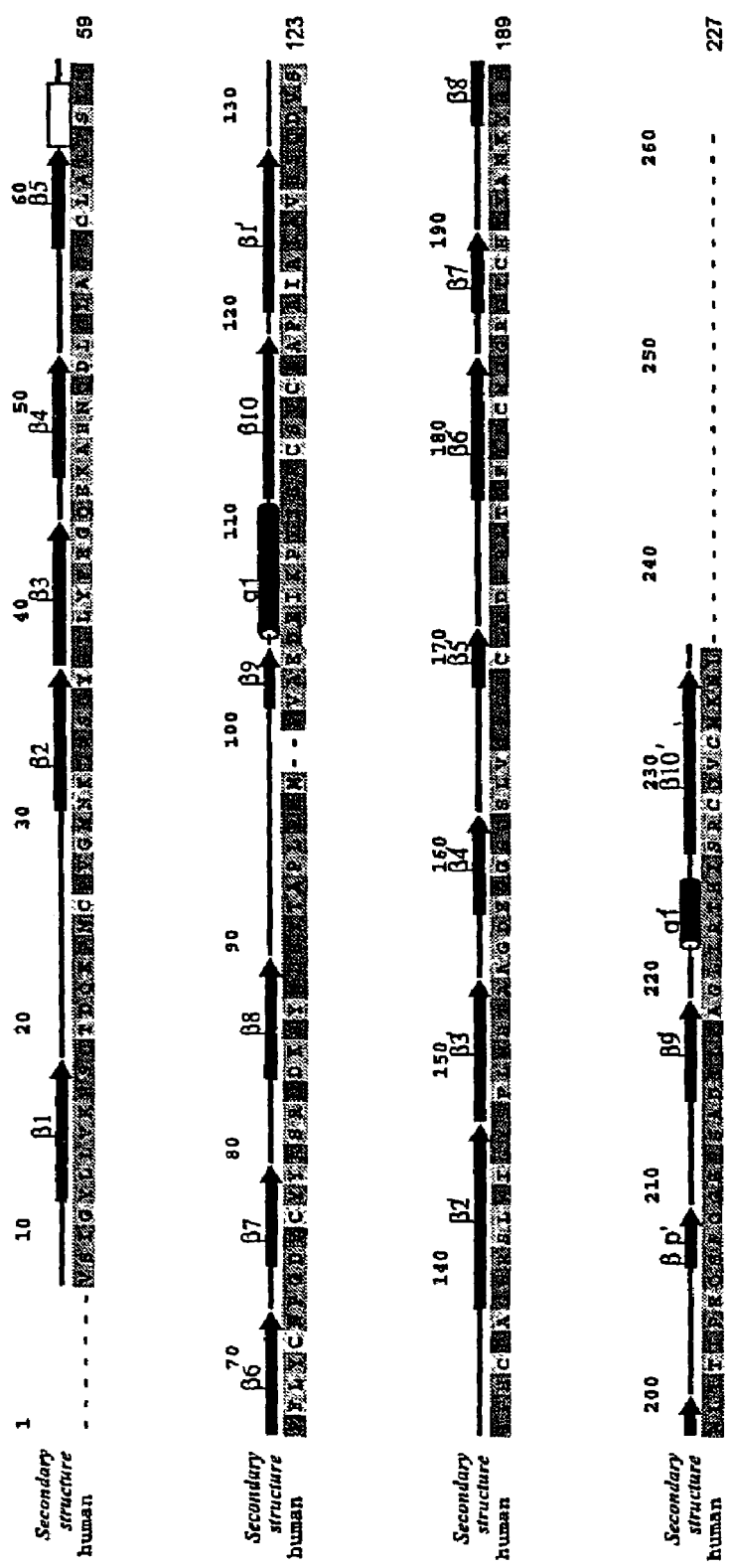
Figure 4:
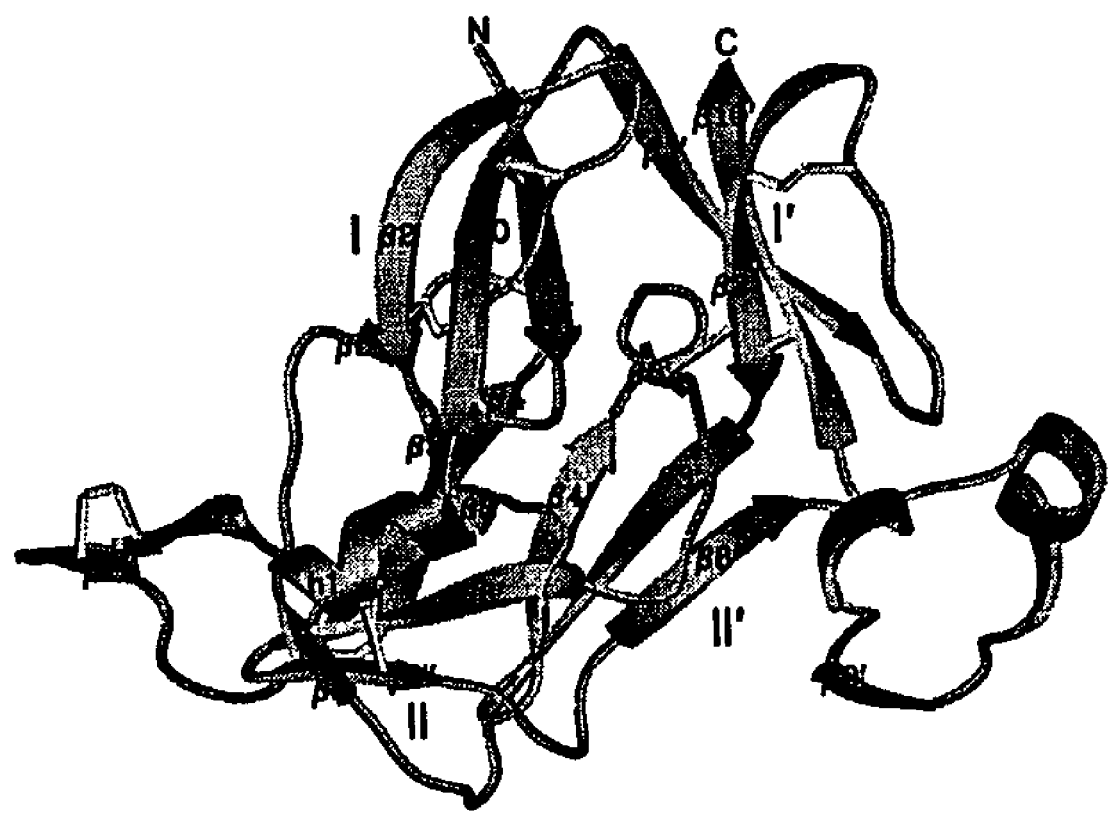
FIG. 4. (a) Illustration of α1 monomer structure in the hexamer. Four β-sheet regions are identified as I, II, II' and II and three short $3_{10}$ helices are also shown.
Figure 5:
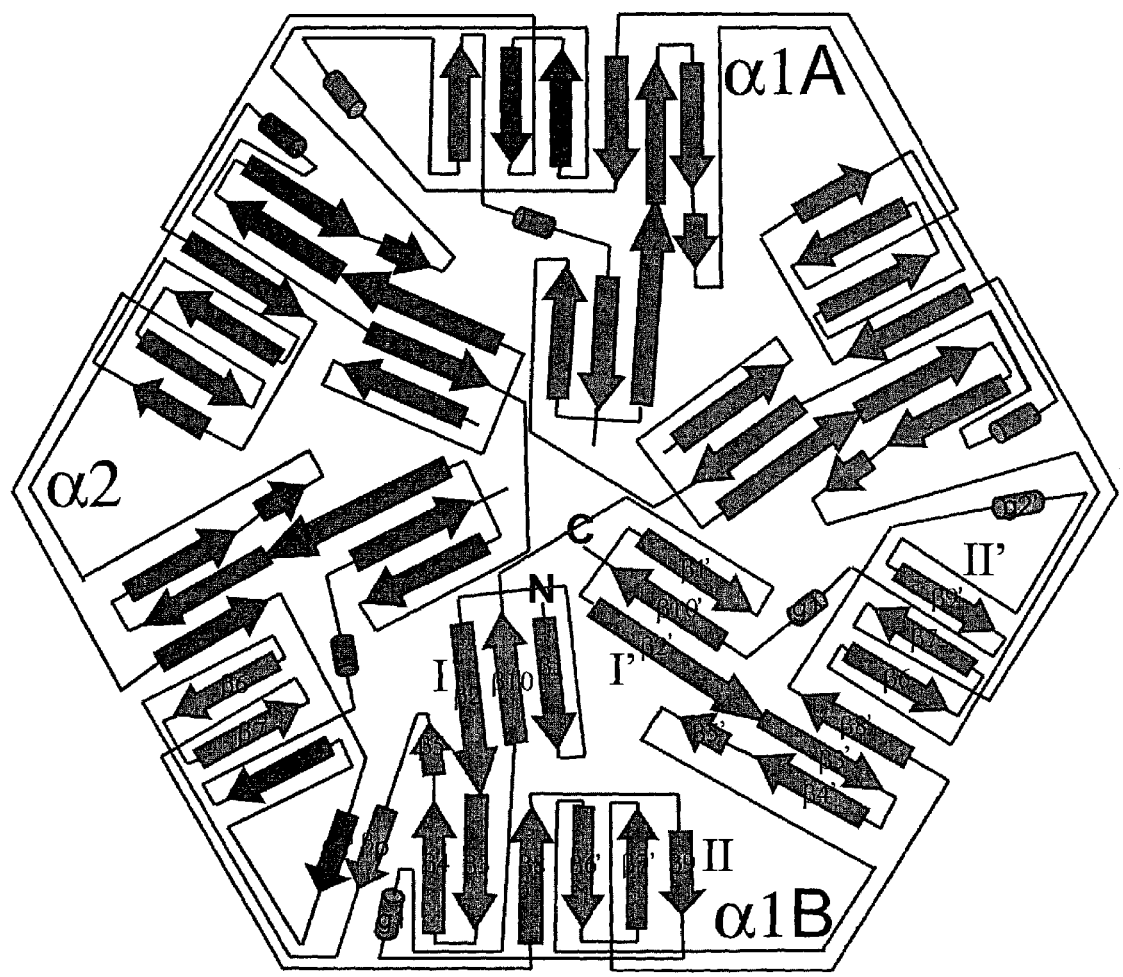
FIG. 5. Topology diagram of NC1 trimer depicting interchain and intrachain 3D domain swapping interactions (generic assembly) and chain interfaces with different secondary structural elements (specific assembly). The secondary structural elements are labeled only for α1A chain. The β-sheets, I & II in the N-subdomain and I' & II' in the C-subdomain are identified. Each subdomain has 10 β-strands (β1–β10 and β1'–β10') and two short $3_{10}$ (g1 and g2') helices. Additionally there are distinct secondary structures at the three interfaces—a parallel β-sheet (βp–βp') at α1B–α2 interface and a $3_{10}$ helix (g1') and extended structure at α1A–α1B and α2–α1A interfaces.

Monomer Topology: The NC1 monomer folds into a novel tertiary structure with predominantly β-strands as predicted by our earlier study using multiple sequence alignment (22)(FIG. 4). The two α1 chains in the trimer are identical and the α2 chain has a similar overall structure. The $C_α$ atoms of 214 matching residues in one of the α1 chains and the α2 chain superimpose with an RMS deviation of 0.9 Å. Each chain can be divided into two homologous subdomains, N- and C-subdomains. The two subdomains fold in a similar topology and $C_\alpha$ atoms of 96 matching residues of two subdomains of α1 chain superimpose with an RMS deviation of 1.0 Å. The 12 invariant cysteine residues form six disulfides, three in each subdomain, at conserved positions (FIGS. 2 and 5). The major difference between the two subdomains occurs at the regions encompassing Pro86-Pro95 in the N-subdomain and Ile196-Thr209 in the C-subdomain, which are least conserved in the six human sequences (FIG. 1). Each subdomain has two β-sheets—a three-strand anti-parallel sheet (I & I') close to the triple helical junction and a six-strand anti-parallel sheet (II & II') close to the hexamer interface, which consists of the regions of interactions between the two trimers that make up the hexamer (FIGS. 4 and 5). The β-sheet I is formed by the three non-contiguous strands (β1, β10 and β2) of the sequence belonging to the first half of the polypeptide. However, in the β-sheet II, only four strands (β4, β3, β8, and β9) belong to the first half of the sequence and the remaining two strands (β6' and β7') form a part of the second half of the sequence. Thus, a β-hairpin structure from the second half of the sequence (the "intra-chain domain swapping region", or "Intra-CDSR") swaps into the N-subdomain to form a six-strand β-sheet. The two halves of the polypeptide being topologically similar, the region in the C-subdomain corresponding to the six-strand β-sheet in the N-subdomain lacks two strands to form a similar β-sheet in the isolated monomer structure. Similarly, β6–β7 hairpin in the N-terminal half, which corresponds to the β6'–β7' hairpin in the C-terminal involved in the domain swapping interaction, extends out in the monomer structure. These two features form the basis for the trimer organization described in the next section.

Trimer Organization: Two chains of the α1 NC1 domain and one chain of the α2 NC1 domain form the trimer structure with a pseudo 3-fold molecular symmetry. Since each chain is made up of topologically similar subdomains, there is even a pseudo 6-fold symmetry. The topology diagram of the trimer is shown in FIG. 5. The trimer structure is approximately cone-shaped with a base diameter of about 65 Å and a hollow core of about 12–14.0 Å inner diameter. This is about the same of as the diameter of the collagen triple helix, with N-termini of all three chains coming together at the vertex of the cone where the triple helical collagenous domain links with the NC1 domain. The trimer is tightly packed through several interchain hydrophobic and hydrogen bonding interactions (Table 2). Residues of five segments in the N-subdomain of one chain make contact with those of seven segments in the C-subdomain of the second chain, and constitute the "monomer-monomer interface", which consists of the regions of monomer-monomer interaction within the trimer. The most important interactions are confined to one N-subdomain segment and two C-subdomain segments (FIG. 1). There are two levels of monomer-monomer interactions, one essential for the "generic trimer" assembly and the other dictating the αNC1 chain specificity of the monomer-monomer interactions within the trimer.

TABLE 2

Comparison of monomer—monomer interfaces in the trimer.

| Interface Parameter | α1A–α1B | | α1b–α2 | | α2–α1A | |
| --- | --- | --- | --- | --- | --- | --- |
|  | α1A | α1B | α1B | α2 | α2 | α1A |
| Number of segments | 5 | 7 | 5 | 7 | 5 | 8 |
| Number of residues | 49 | 60 | 51 | 65 | 49 | 59 |
| Δ ASA(Å²) | 2137 | 2182 | 2087 | 2066 | 1985 | 2044 |
| Polar/non-polar atoms (%) | 40.1/59.9 | 24.5/75.5 | 44.3/55.7 | 32.5/67.5 | 39.9/60.1 | 24.8/75.3 |
| Hydrogen bonds M—M/M–S/S—S | 9/8/5 | | 11/8/12 | | 9/9/3 | |

Δ ASA, interface solvent accessible area; M, main chain; S, side chain

Within the trimer, the following monomer-monomer interfaces exist: α1A–α2C; α1B–α2C; and α1A–α1B. The hexamer contains two such trimers; the monomer-monomer interfaces in the second trimer are α1D–α2F; α1E–α2F; and α1D–α1E.

Figure 6A:
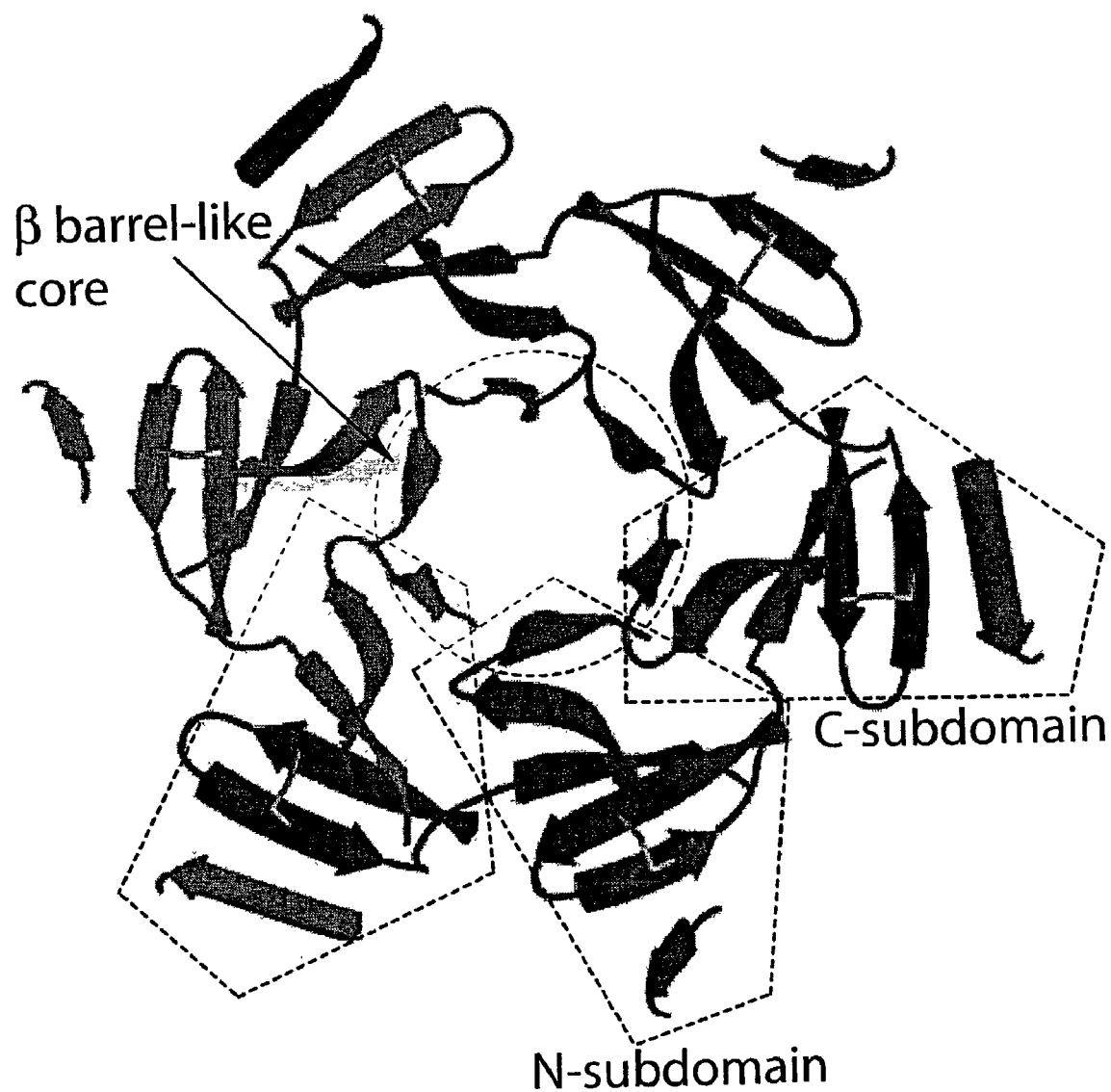
FIG. 6. a) Generic interactions in the trimer. Six-strand β-sheets formed by interchain and intrachain 3D domain swapping interactions form the major force in the trimer organization. The sheets belonging to subdomains are shown in boxes to highlight such interactions. Central β barrel-like core, shown inside the circle, also plays a role in packing and stabilizing this scaffold. (b) Unique secondary structures and prominent side chain interactions at the three interfaces are shown. The α1b–α2 interface has more number of hydrogen bonds than the other interfaces.

Generic Trimer: At the first level, the monomers intertwine with each other to form the trimer through 3D domain swapping interactions (FIGS. 5 and 6a) (53). A six-strand β-sheet (II') is formed in the C-subdomain from strands of two different α chains similar to the β-sheet II in the N-subdomain formed from the strands in two halves of the same chain. These β-sheets are indistinguishable in α1 and α2 chains. Thus, there are six β-sheets (II/II'), one in each of the six subdomains, forming the close-ended 3D domain swapping interactions in the NC1 trimer structure. Each of these six-strand β-sheets is formed by four strands (β4/4', β3/3', β8/8', β9/9') in one half of the sequence and the remaining two strands (β6'/6, β7'/7) are contributed by the other half of the same chain (β6/β7; the Inter-CDSR) or adjacent chain (β6'/β7/; the "Intra-chain domain swapping region", or "Intra-CDSR"). The amino acid sequences of all the strands with the exception of β9, are highly conserved in α chains within and across the species. The six topologically similar β-sheets formed in cyclical fashion give the pseudo 6-fold symmetry appearance for the trimer (FIG. 6a). In each of the β-sheets, the outermost strand (β9/β9') lies on the surface parallel to the equatorial plane of the hexamer interface forming a part of the outer ring and the innermost strand (β4/β4') runs nearly parallel to the polar axis or pseudo 3-fold axis in the core. The angle between these two strands within each sheet is about 75° giving it a right-handed twist. The β4/β4' strands from all the six β-sheets form a parallel β barrel-like core of about 14 Å diameter even though there are no backbone hydrogen bonds between them (FIG. 6a). However, these core strands are stabilized by backbone-side chain hydrogen bonds either directly or mediated through solvent molecules. The β4/4' strands have a mixture of hydrophobic and hydrophilic residues, with the former pointing to the core and the latter pointing towards the adjacent strand. Interestingly, the β4 strands contain long chain hydrophilic amino acids so that they form more direct hydrogen bonds with the backbone atoms of the β4' strand of the neighboring chain indicating stronger interchain interactions. The interactions between β4' and β4 within a chain are mainly mediated through solvent molecules. Thus, the six-strand β-sheets are essential structural components in the organization of the generic trimer structure through 3D domain swapping interactions and the compact β barrel-like core structure. However, they may play only a limited role in the chain specific assembly of the trimer. Therefore, compounds that target the Intra-CDSR, the Inter-CDSR, and the β4/β4' based β barrel-like core, such as peptides derived from these regions, can be used to inhibit generic monomer-monomer interactions, and thus to inhibit trimer assembly.

Figure 6B:
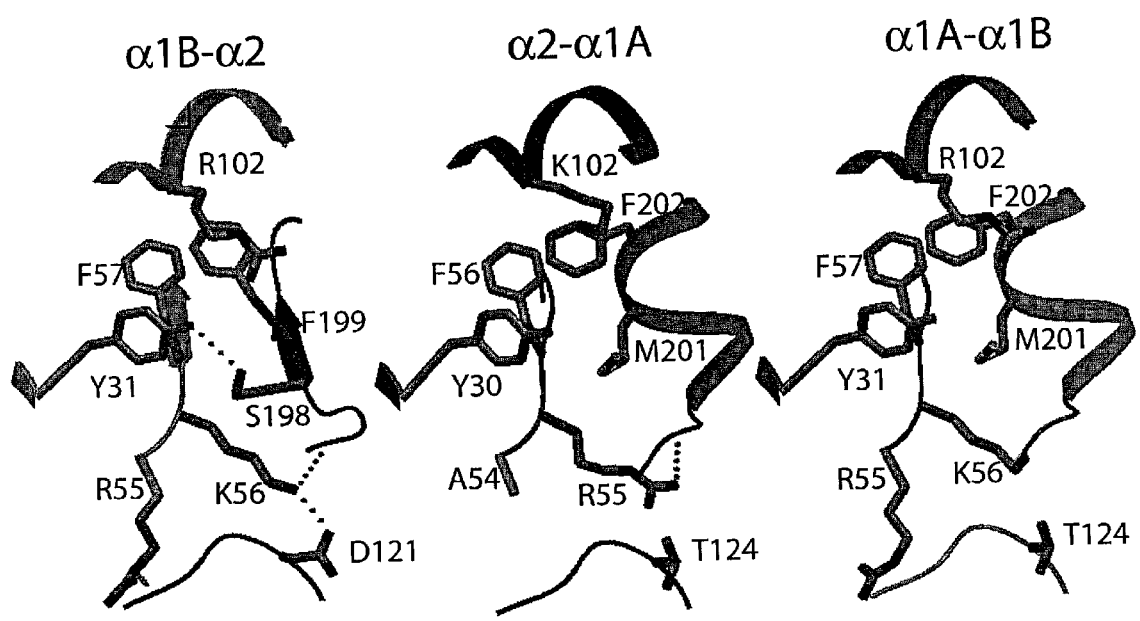

Chain Specificity in the Trimer Structure: The sequence of the loop connecting the β8' and β9' strands is the most variable region in all the six human α chains (referred to as the "hypervariable region"). This hypervariability in the primary sequences manifests itself as different secondary structures in the α1 and α2 chains in the crystal structure. Whereas it forms a short $3_{10}$ helix (g2') in all the α1-like chains (the "specificity region partner" or "SRP"; Glu200-Lys204 (EMFKK)), the corresponding region in α2 chain (Ser198-Gln200; SFQ) adopts an extended conformation (βp') and pairs with the extended structure (the "specificity region", or "SR"; βp, Phe57-Met60; FSTM) in the adjacent α1B chain to form a short parallel β-sheet (FIG. 8b). It should be noted that the sequence of the SR from α1 and α2 is identical (FSTM). This is the only parallel β-sheet in the entire structure, which is predominantly made up of β-strands. The sequence of the βp is highly conserved in all the six α chains and forms the same extended structure in α2 chain also, even though it doesn't have a partner in α1A chain to form the parallel β-sheet. Thus, these additional main chain hydrogen bond interactions between the two chains are found only at the α1B–α2 interface (i.e.: which includes the interaction of the SR of α1 and the SRP of α2), but not in α2–α1A (i.e.: which includes the interaction of the SRP of α1 and the SR of α2) or α1A–α1B (i.e.: which includes the interaction of the SR of α1 and the SRP of α1) interfaces, due to the presence of the $3_{10}$ helical structure in α1 chains rather than the extended structure present in α2 chain. Besides this difference in the secondary structural elements in the three interfaces, there are also differences in the main chain-side chain and side chain side chain interactions at the monomer-monomer interface (FIG. 6b). This is also reflected in different ratios of polar to non-polar atoms at the three interfaces (Table 2). Therefore, compounds that target the SR, the SRP, or the hyper-variability region, such as peptides derived from these regions, can be used to inhibit specific monomer-monomer interactions, and thus inhibit trimer assembly.

Furthermore, given the composition of the individual interfaces within the monomer-monomer interface, a preferred inhibitor of specific trimer assembly would target the SR, which is identical in α1 and α2, and thus such an inhibitor would be expected to interfere with interactions at each interface within the monomer-monomer interface, and thus to inhibit trimer assembly. Also preferred would be an inhibitor that targets the α2 SRP, which is required for the additional H-bonding interactions seen at the α1B–α2 interface.

The side chain of Lys56(α1B) is sandwiched between the backbone of the loop preceding the parallel β-sheet in α2 chain and the contiguous bonds of backbone and side chain of Gln120(α2). In this tightly locked position, Lys56(α1B) assumes a linear conformation to form two strong hydrogen bonds with the carbonyl of Ile194(α2) and the carboxyl of Asp121(α2), and two more weak interactions with the carbonyls of Gln120(α2) and Glu196(α2). The α1-like (ie: α1/3/5 family) region corresponding to the parallel β-sheet of α2 chain is the $3_{10}$ helix, which spans a longer sequence. Hence, in the α1A–α1B interface, Lys56(α1A) is not quite parallel to the backbone bonds, which provides more room for this lysine to adopt a different rotamer conformation to form only weak hydrogen bond with the carbonyl oxygen of Ile196(α1B). This may also be influenced by the presence of hydrophobic Thr124 in α1 chains in place of hydrophilic Asp121 in α2. At the α2–α1A interface Arg55(α2) is docked in similar position as Lys56 of α1 chains in other two interfaces with one strong hydrogen bond interaction with carbonyl of Ile196(α1A). Other differences in amino acid sequences including Arg55/Ala54 and Gly98/Glu95 make differences in hydrogen bonding patterns at the interfaces. Thus, the Arg55(α2)/Lys56(α1) is an important residue for optimal α1–α2monomer-monomer interactions, and compounds targeting this region, such as peptides including LRKF (SEQ ID NO:294) (α1) or LARF (SEQ ID NO:295) (α2), can be used to inhibit the assembly of specific monomer-monomer interactions. Since this region precedes the SR, this region can be combined with the SR to form a longer peptide that will interfere with multiple aspects of specific monomer-monomer interactions, and thus be even more effective at inhibiting trimer assembly.

Furthermore, the regions Ile194-Glu196 (α2), Ile196 (α1) and Gln120-Asp121(α2) also are involved in optimal α1–α2monomer-monomer interactions, and compounds targeting these region, such as peptides including IPE (SEQ ID NO:294) (α2 184–196), IER (SEQ ID NO:295) (α1 196–198) or QD (SEQ ID NO:296) (α2 120–121), can be used to inhibit the assembly of specific monomer-monomer interactions, and thus to inhibit trimer assembly.

The α1B–α2 interface (i.e.: which includes the interaction of the SR of α1 and the SRP of α1) has the maximum number of contact residues, the highest proportion of hydrophilic atoms, and contains more hydrogen bonds than the other monomer-monomer interfaces (Table 2). On the other hand, the buried surface area is largest for α1A–α1B interface (i.e.: which includes the interaction of the SR of α1 and the SRP of α1). From these observations, it is evident that the α1B–α2 interface is formed predominantly through hydrogen bonding interactions and the α1A–α1B interface is stabilized by more hydrophobic forces.

In addition to the specific interactions at the interfaces, packing considerations may also play an important role in determining chain stochiometry in the trimer. Even though the α1 and α2 NC1 chains fold in a similar tertiary structure with a low RMS deviation, the relative orientation of the two subdomains in each NC1 chain is different near the triple helical junction. The region encompassing Thr13-Tyr30 of the N-subdomain in the α2 chain is farther from its equivalent region Asp121-Tyr138 of the C-subdomain in the α2 chain compared to the relative orientations of similar regions in the α1 structure. The larger width of the α2 structure near the triple helical junction results in serious steric clashes when packed into a hypothetical α2-homotrimer. However, it is possible to accommodate three α1 chains in a hypothetical homotrimer, albeit with weaker interactions.

It is preferred that peptides designed to interfere with monomer-monomer interactions are preferably delivered into the cell, where such monomer-monomer assembly occurs. Alternatively, the peptides can be used to disrupt assembled trimers that have been secreted by the cell.

Hexamer Assembly: The type IV collagen trimer, once formed in the endoplasmic lumen, is secreted into the extracellular space where it assembles into the hexamer, and then into a supramolecular network through N- and C-terminal associations. The NC1 domains play the dominant role in this assembly, by determining the C-terminal dimeric association, leading to hexamer assembly. In this section we describe the forces that influence such hexamer assembly as observed in the crystal structure, and provide a rationale for the specificity in the type IV collagen network assembly.

The foot-ball shaped hexamer is made up of two identical trimers, each containing two α1 chains and one α2 chain as described in the previous section. Each protomer (ie: the complete type IV collagen trimer, including NC1 domains) formed by the tightly intertwined trimer is considered as a single entity so that the hexamer can be analyzed relative to other homodimeric protein complexes (43). We have determined several parameters defining the hexamer interface to evaluate the strength of interactions between the two trimers and analyze hexamer assembly in the type IV collagen network (Table 3).

TABLE 3

Comparison of interface parameters defining the trimer—trimer interaction in the NC1 hexamer and observed mean for 32 homodimer complexes.

| Interface Parameter | NC1 Hexamer | Observed Mean (43) (32 Homodimers) |
| --- | --- | --- |
| ΔASA (Å$^2$) | 4173.1 | 1685.03 |
| Planarity | 1.91 | 3.46 |
| Circularity | 0.87 | 0.71 |
| Segmentation | 18 | 5.22 |
| Hydrogen bonds per 100 Å$^2$ | 1.2 | 0.70 |
| Gap Index | 1.24 | 2.2 |

Percentage of polar and non-polar atoms are 45.5 and 54.5 respectively.

Like most homodimers, the two NC1 trimers are related by a 2-fold NCS axis in lying the equatorial plane and perpendicular to the pseduo 3-fold axis of symmetry within an individual trimer (FIG. 4). This symmetry constraint may be partly influenced by a few differences in the interface residues of α1 like and α2 like sequences in addition to more efficient packing. The hexamer interface is formed by the nearly flat surfaces of the two trimers, with an RMS deviation of 1.9 Å for all the hexamer interface atoms from the mean plane (FIG. 9a). This is significantly lower than the average planarity value of 3.5 Å for 32 homodimers discussed in a recent review (43). The hexamer interface formed by six segments each of the three monomers, with a total of 109 residues per trimer, is nearly circular, with the major and minor axial lengths of the mean plane measuring approximately 69 and 61 Å respectively. This flat circular hexamer interface covers about 4400 Å$^2$ of solvent accessible area per trimer, which correlates with the observation of larger molecules having larger interfaces (54). Such a large interface facilitates strong interaction between the trimers, involving both hydrophobic and hydrophilic residues. The polar (45.5%) and non-polar atoms (54.5%) in the hexamer interface are nearly in equal proportions, underscoring the importance of both types of interactions in hexamer stabilization.

Figure 7A:
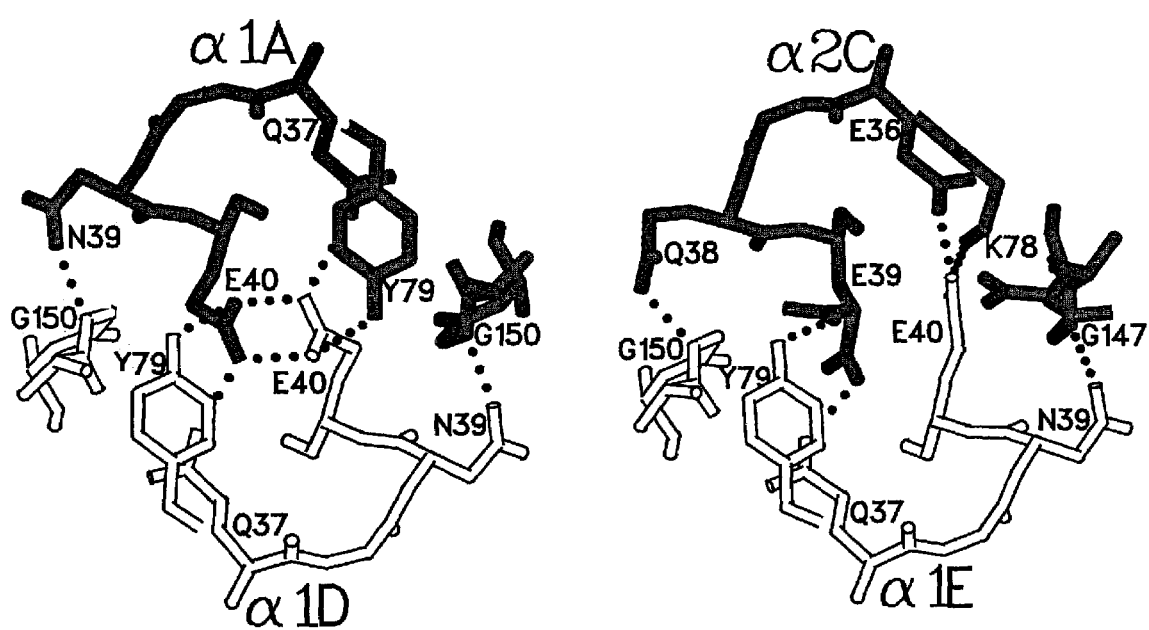
FIG. 7. Trimer-trimer interface. Comparison of essential hydrogen bonding interactions in the interface at "core" (FIG. 7A), "outer" (FIG. 7B) and major-minor junction (FIG. 7C) for α1—α1 and α1–α2 dimers (see text for details).
Figure 7B:
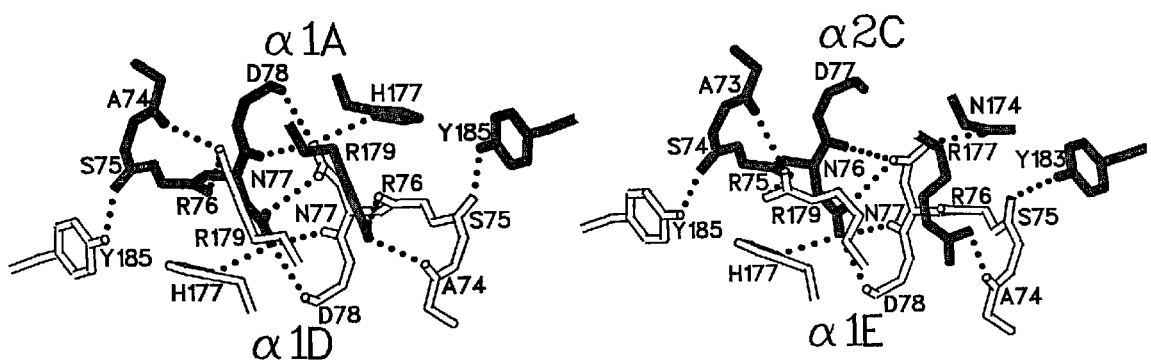

The discussion thus far focused on the overall nature of the hexamer interface. Next, the interactions between the individual chains at the hexamer interface are analyzed in more detail. Each monomer of one trimer makes contact with two monomers of the other trimer, designated as the "major" and "minor" contacts based on the extent of the contact area and number of hydrogen bonds. The two monomers making major contact is referred to as "dimer" in a similar sense as the term used in the denaturation experiments of hexamers (55). The 2-fold NCS between the two trimers results in only one "homodimer" formed by two α1 chains (FIG. 7A), with the remaining two "heterodimers" formed by α1 and α2 chains (FIGS. 7A–B).

A 120° rotation of one trimer with respect to the other about the pseudo 3-fold axis will result in an "all homodimers" structure. Why such an arrangement is not possible can be explained mainly on symmetry consideration: breaking the symmetry results in less efficient packing with possibly fewer interactions and some unfavorable contacts. In order to understand the complex hydrogen bonding interactions at the interface, it is essential to look into the interactions of each monomer with its "major" and "minor" interacting partners. The complexity presented even at this level may be simplified further by breaking down the interactions to three regions in the structure: "core" and "outer" regions of "major" contact and the "major-minor junction".

Core regions of major contact: The two 6-strand β-sheets, II and II', formed by the 3D domain swapping interactions play as crucial role in the formation of hexamer assembly as in the case of trimer organization. The hexamer interface is populated with β-turns connecting β3–β4 and β3'–β4' in the core. These turns along with the remaining strands of the β-sheets II/II' position a large number of conserved residues for extensive hydrogen bonding interactions at the hexamer interface. The core β-turns (two per monomer contributed by the two equivalent subdomains) in the two trimers pack in staggered configuration such that each turn in one trimer contacts with two turns in the other trimer. The turns in the N-subdomains are of type I'/III' containing hydrophilic amino acids in the second (Asn39/Gln38) and third positions (Glu40/39). The C-subdomain turns are of type II in α1 chains and type II' in α2 chains with small hydrophobic amino acids, Ala149/146-Gly150/147-Ala151/Asp148, with Ala149 α1 or Asp148 of α2 introducing a β-bulge. Thus, the hydrophilic side chains of turns in the N-subdomain participate in hydrogen bonds and hydrophobic residues of turns in C-subdomain pack through hydrophobic interaction as well as stacking interaction of peptide planes (FIG. 7A). Whereas the Asn39(Gln38) side chain in the N-subdomain forms a hydrogen bond with the backbone amide in C-subdomain turn, the conserved Glu40(39) penetrates between the N- and C-subdomains of a monomer chain in the other trimer to form a hydrogen bond with the side chain of the conserved Gln37(36). The Glu40 residues in the α1–α1 dimer form a strong hydrogen bond with each other that is missing in α1–α2 dimers. The packing of the turns and side chains appear to be tight at the core interface in CPK models indicating strong van der Waals interactions in additions to the obvious hydrogen bonding interactions. Therefore, compounds that target the core regions of major contact at the hexamer interface, such as peptides derived from these regions, can be used to inhibit hexamer assembly. For example, peptides including the β3–β4 connecting region or the β3'–β4' connecting region, can be used to inhibit hexamer assembly at the core region of major contact.

Outer regions of major contact: The sequence variability preceding Arg179(177), influences the number of potential H bonds at the α1–α2 (hexamer) interface. The interactions in the outer region involve the highly conserved loop connecting the β7 and β8, and β7'–β8' sheets. In the α1–α1 major interface of the hexamer, five contiguous carbonyl oxygens of highly conserved Ala174-Asp78 in one chain form hydrogen bonds with side chains Asn77, Arg179, and Tyr185 of the other chain in symmetrical sets (FIG. 9c). These side chains are also conserved in both α1 and α2 chains. However, insertion of Gly176 and substitution of Asn174 in α2 sequence alters the orientation conserved Asn78 and Arg177 residues, which results in the few hydrogen bonds in the α1–α2 interface. Therefore, compounds that target the outer regions of major contact at the hexamer interface, such as peptides derived from these regions, can be used to inhibit hexamer assembly. For example, peptides including the sequence ASRND (SEQ ID NO:201) (α1) or YYANA (SEQ ID NO:218) (α1), or the corresponding sequences in the other alpha chains, can be used to inhibit hexamer assembly at the outer region of major contact.

Figure 7C:
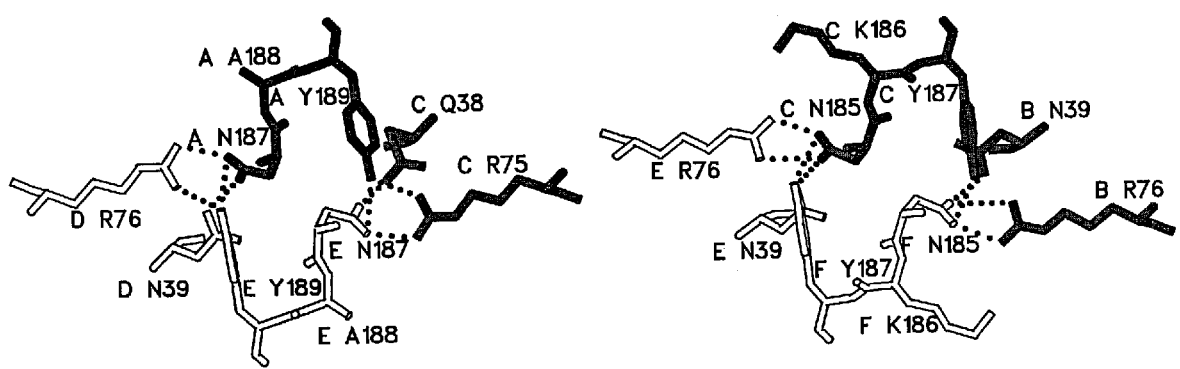

Major-minor junction: The major-minor junction is the area of the hexamer interface where two chains from one trimer contact two chains of the other trimer. There are two types of junctions, one involving three α1 and one α2 chains, and the other involving two each of α1 and α2 chains. The hydrogen bonding pattern in the two junctions is highly conserved (FIG. 7C). Both α1–α1 and α2–α2 form a Asn187(185)-Tyr189(188) (NYY) (SEQ ID NO:297) hydrogen bond pairs in the interface. In addition to this, Asn187(185) forms a pair of hydrogen bonds with Arg76 (75) of another chain (within the outer region of major contact discussed above) from the opposite trimer. The multiple hydrogen bonds formed by Asn187(185) involving residues from two different chains is probably one of the major factors stabilizing the trimer-trimer interface. Therefore, compounds that target major-minor junction at the hexamer interface, such as peptides derived from these regions, can be used to inhibit hexamer assembly. For example, peptides including the sequence NYY (SEQ ID NO:288) (α1) (such as ECHGRGTCNYY (SEQ ID NO:172)), or corresponding sequences in the other α chains, all of which is present at the hexamer interface (and which includes a large portion of the Intra-CDSR), or ASRND (SEQ ID NO:201) (α1(which includes the ARG76(75) residue), or corresponding sequences in the other α chains, can be used to inhibit hexamer assembly at the major-minor junction. Thus, peptides containing the sequence ASRND (SEQ ID NO:201) can interfere with hexamer assembly by interfering with interactions at both the outer region of major contact and the major-minor junction. Similarly, peptides that target the Intra-CDSR and extend to contain the 2 additional Y residues from the sequence "NYY" (SEQ ID NO:288) can be used to inhibit trimer assembly, as well as hexamer assembly.

Other residues that are located at the hexamer interface, and that are believed to be important for hexamer assembly, include (1) MSMAP (SEQ ID NO:129) (residues 91–95 α1)/MMP (SEQ ID NO:132) (α2), and corresponding sequences in the other α chains; (2) PSTLK (SEQ ID NO:177) (residues 208–212 in α1; β9' strand; ADTLK in α2 (SEQ ID NO:180)), and corresponding sequences in the other α chains; (3) FCNINNVCNFA (SEQ ID NO:289) (α1 AND (α5—co-extensive with the Inter-CDSR), and corresponding sequences in the other α chains:

| | | |
|---|---|---|
| α3: | FCNVNDVCNF | (SEQ ID NO:298) |
| α2: | YCNPGDVCYY | (SEQ ID NO:299) |
| α4: | YCNIHQVCHY | (SEQ ID NO:300) |
| α6: | YCNINEVCHY | (SEQ ID NO:301) |

Thus, peptides containing these sequences, or portions thereof, can be used to inhibit hexamer assembly.

Disulfide Bonds: Interchain or Intrachain?

Disulfide cross-linking is a recurring theme in collagen assembly and is believed to play an important role in the stabilization of the trimeric structure (11). Fibrillar procollagens are believed to form interchain disulfide bonds catalyzed by protein disulfide isomerase in either the C-telopeptide or C-propeptide (56, Kiovu, 1987 #343). Interchain disulfides have been proposed to form both in the collagenous and NC1 domains of type IV collagen. Whereas the interchain disulfides in the collagenous domains are formed within a protomer to stabilize the collagen triple helix, those in the NC1 domains are believed to occur between the protomers to stabilize the network at the C-terminus. Disulfide exchange between NC1 domains of similar α chains from two different protomers was proposed as one of the major stabilizing forces in the hexamer assembly (57). Under denaturing conditions, the human placenta derived NC1 hexamer dissociated as dimers and monomers. The dimers were shown to be crosslinked predominantly by disulfide bridges. However, a later study by Langeveld et al (55) comparing the NC1 hexmers isolated from several BMs revealed rather complex results. Whereas the results of placenta BM and kidney glomerular BM NC1 hexamers agreed with the previous observations, dissociating as dimers upon denaturation, the LBM NC1 hexamer dissociated predominantly as monomers implying the absence of disulfide cross-linking. The crystal structure of LBM NC1 hexamer reveals just that—all the cysteines are involved in intrachain disulfides.

Siebold et al (57) proposed disulfide exchanges involving Cys20(20')-Cys111'(111) and Cys53(53')-Cys108'(108) pairs in N-subdomain (and those in similar positions in C-subdomain) in α1 chain resulting in a total of four disulfide crosslinkings in each subdomain based on the cynogen bromide. The topological arrangement of disulfides observed in the crystal structure suggests the possibility for such a rearrangement is extremely remote (FIG. 7A). The disulfides in the NC1 monomer are arranged in three tiers with Cys20-Cys111 and Cys130-Cys225 are close to the triple helical junction, Cys65-Cys71 and Cys176-Cys182 are close to the interface and Cys53-Cys108 and Cys164-Cys222 lies in between. The disulfide pairs Cys20-Cys111 and Cys53-Cys108 in the monomers of α1A–α1D dimer are about 70 Å and 50 Å apart respectively. Thus the possibility for disulfide exchange, if any, exists only for the Cys65-Cys71 and Cys176-Cys182 pairs. However, the staggered arrangement of the two trimers brings Cys65–Cys71 pair of α1A closer to its C-subdomain equivalent Cys176'–Cys182' pair of α1D chain rather than its counterpart Cys65'–Cys71' in the N-subdomain. These two closest disulfide pairs in α1A–α1D dimer are about 16 Å from each other. Even more importantly, these intrachain disulfides are located in the 3D domain-swapped β-hairpin regions. If the disulfide exchanges were indeed possible between these pairs it would involve major conformational alterations. Such a movement of the β-hairpins containing the "exchangeable" cysteine residues would break both the interchain and intrachain 3D domain swapping interactions, thus destabilizing the trimer structure. From these arguments, it is difficult to envisage disulfide cross-linking between the monomers belonging to two protomers in the present structure. We also examined the possibility of intra-protomer disulfides, which would also require major conformational changes and potentially move the N-terminii of the three chains severely affecting collagen-NC1 linkage. An alternative conformation must exist for the NC1 domains from all other BMs to account for the interprotomer disulfide cross-linkings.

Biological Significance. There is very little crystallographic data available on non-collagenous domains. The only available structures of non-collagenous domains are those of endostatins (58,59), which are homologous fragments of single chains from types XVIII and XV collagens.

The present work provides the first unambiguous structural basis for the chain stochiometry of the type IV collagen α1.α2 network, as well as the structural basis for chain specific assembly of type IV collagen. The NC1 monomer folds into a novel tertiary structure and the close ended-trimer of $(\alpha 1)_2.\alpha 2$ is organized through unique 3D domain swapping interactions. These features must be conserved in all type IV collagen networks, from all species, due to overall sequence similarity and very high sequence identity of the regions participating in domain swapping. The chain specificity is determined by the differences in the primary sequences of the hypervariable regions of the NC1 domains of the constituent chains, which manifest as different secondary structures at the monomer-monomer interfaces. The hexamer structure is stabilized by the extensive hydrophobic and hydrophilic interactions at the trimer-trimer interface without a need for disulfide cross-linking. The crystal structure of LBM NC1 hexamer and the denaturation studies of NC1 hexamers from several BMs suggest an alternative conformation must exist in hexamers that are cross-linked by interchain disulfides. Some hitherto unknown enzymatic process might be responsible for folding the same amino acid sequences into different conformations in different tissues.

REFERENCES

1. Timpl, R., and Brown, J. C. (1996) *Bioessays* 18(2), 123–131
2. Weber, M. (1992) *Kidney International* 41, 620–628
3. Pihlajaniemi, T. (1996) in *Molecular Pathology and Genetics of Alport Syndrome* (Trygvasson, K., ed) Vol. 117, pp. 46–79, Karger, Basel
4. Miner, J. (1999) *Kidney International* 56, 2016–2024
5. Prockop, D. J., and Kivirikko, K. I. (1995) *Ann. Rev. Biochem.* 64, 403–34
6. Myllyharju, J., and Kivirikko, K. I. (2001) *Ann Med* 33, 7–21
7. Kadler, K. (1994)
8. Bachinger, H.-P., Bruckner, P., Timpl, R., Prockop, D. J., and Engel, J. (1980) *Eur. J. Biochem.* 106, 619–632
9. Bachinger, H.-P., Fessler, L. I., Timpl, R., and Fessler, J. H. (1981) *J. Biol. Chem.* 256, 13193–13199
10. Dolz, R., Engel, J., and Kuhn, K. (1988) *Eur J Biochem* 178(2), 357–66
11. McLaughlin, S. H., and Bulleid, N. J. (1998) *Matrix Biology* 16, 369–377
12. Lees, J. F., Tasab, M., and Bulleid, N. J. (1997) *EMBO J.* 16(5), 908–916
13. Dion, A. S., and Myers, J. C. (1987) *J Mol Biol* 193(1), 127–43
14. Rosenbloom, J., Endo, R., and Harsch, M. (1976) *J. Biol. Chem.* 251, 2070–2076
15. Schofield, D. J., Uitto, J., and Prockop, D. J. (1974) *Biochemistry* 13, 1801–1806
16. Uitto, V., Uitto, J., and Prockop, D. J. (1981) *Arch. Biochem. Biophys.* 210, 445–454
17. Boutaud, A., Borza, D.-B., Bondar, O., Gunwar, S., Netzer, K.-O., Singh, N., Ninomiya, Y., Sado, Y., Noelken, M. E., and Hudson, B. G. (2000) *J. Biol. Chem.* 275, 30716–30724
18. Borza, D. B., Bondar, O., Ninomiya, Y., Sado, Y., Naito, I., Todd, P., and Hudson, B. G. (2001) *J Biol Chem* 276(30), 28532–40.
19. Hudson, B. G., Reeders, S. T., and Tryggvason, K. (1993) *J Biol Chem* 268(35), 26033–6
20. Timpl, R., Wiedemann, H., van Delden, V., Furthmayr, H., and Kuhn, K. (1981) *Eur J Biochem* 120(2), 203–11
21. Zhou, J., Ding, M., Zhao, Z., and Reeders, S. T. (1994) *J. Biol. Chem.* 269, 13193–13199
22. Netzer, K. O., Suzuki, K., Itoh, Y., Hudson, B. G., and Khalifah, R. G. (1998) *Protein Sci* 7(6), 1340–51
23. Fowler, S. J., Jose, S., Zhang, X., Deutzmann, R., Sarras, M. P., Jr., and Boot-Handford, R. P. (2000) *J Biol Chem* 275(50), 39589–99.
24. Boute, N., Exposito, J. Y., Boury-Esnault, N., Vacelet, J., Noro, N., Miyazaki, K., Yoshizato, K., and Garrone, R. (1996) *Biol Cell* 88(1–2), 37–44
25. Guo, X. D., and Kramer, J. M. (1989) *J Biol Chem* 264(29), 17574–82.
26. Sibley, M. H., Johnson, J. J., Mello, C. C., and Kramer, J. M. (1993) *J Cell Biol* 123(1), 255–64.
27. Blumberg, B., MacKrell, A. J., and Fessler, J. H. (1988) *J Biol Chem* 263(34), 18328–37.
28. Exposito, J. Y., D'Alessio, M., Di Liberto, M., and Ramirez, F. (1993) *J Biol Chem* 268(7), 5249–54.
29. Gunwar, S., Ballester, F., Noelken, M. E., Sado, Y., Ninomiya, Y., and Hudson, B. G. (1998) *J Biol Chem* 273(15), 8767–75
30. Zhang, X., Hudson, B. G., and Sarras, M. P., Jr. (1994) *Dev Biol* 164(1), 10–23
31. Guo, X., Johnson, J. J., and Kramer, J. M. (1991) *Nature* 349, 707–709
32. Sibley, M. H., Graham, P. L., von Mende, N., and Kramer, J. M. (1994) *EMBO J.* 13, 3278–3285
33. Kashtan, C. E., and Michael, A. F. (1993) *Am. J. Kid. Dis.* 22, 627–640
34. Kashtan, C. E., and Michael, A. F. (1996) *Kidney Int* 50, 1445–1463
35. Cosgrove, D., Meehan, D. T., Grunkemeyer, J. A., Komak, J. M., Sayers, R., Hunter, W. J., and Samuelson, G. C. (1996) *Genes Dev* 10(23), 2981–92.
36. Miner, J. H., and Sanes, J. R. (1996) *J Cell Biol* 135(5), 1403–13.
37. Gunwar, S., Noelken, M. E., and Hudson, B. G. (1991) *J Biol Chem* 266(21), 14088–94
38. Peczon, B. D., McCarthy, C. A., and Merrit, R. B. (1982) *Exp. Eye. Res.* 35, 643–651
39. Otwinowski, Z., and Minor, W. (1997) *Methods in Enzymology* 276, 307–326
40. Terwilliger, T. C., and Berendzen, J. (1997) *Acta Crystallogr.* D55, 849–861
41. Terwilliger, T. C. (2000) *Acta Crystallogr D* 56(Pt 8), 965–72.
42. Dodson, E. J., Winn, M., and Ralph, A. (1997) *Methods in Enzymology* 277, 620–633
43. Jones, S., and Thornton, J. M. (1996) *Proceedings of The National Academy of Science (U.S.A)* 93, 13–20
44. Brunger, A. T., Adams, P. D., Clore, G. M., DeLano, W. L., Gros, P., Grosse-Kunstleve, R. W., Jiang, J. S., Kuszewski, J., Pannu, N. S., and al., e. (1998) *Acta Crystallogr.* D54, 905–921
45. Evans, S. V. (1993) *J. Mol. Graphics* 11, 134–138

46. Nicholls, A., Sharp, K. A., and Honig, B. (1991) *Proteins* 11, 281–296
47. Laskowski, R. A. (1995) *J. Mol. Graph.* 13., ,323–330
48. McDonald, I. K., and Thornton, J. M. (1994) *J. Mol. Biol.* 238, 777–793.
49. Timpl, R., Oberbaumer, I., von der Mark, H., Bode, W., Wick, G., Weber, S., and Engel, J. (1985) *Ann NY Acad Sci* 460, 58–72
50. Stubbs, M., Summers, L., Mayr, I., Schneider, M., Bode, W., Huber, R., Ries, A., and Kuhn, K. (1990) *J Mol Biol* 211, 683–684
51. Dauter, Z., and Dauter, M. (1999) *J. Mol. Biol.* 289, 93–101
52. Dauter, Z., Dauter, M., and Rajashankar, K. R. (2000) *Acta Crystallogr.* D56, 232–237
53. Schlunegger, M. P., Bennett, M. J., and Eisenberg, D. (1997) *Advances in Protein Science* 50, 61–132
54. Jones, T. A. (1978) *J. Appl. Crystallogr.* 11, 268–272
55. Langeveld, J. P., Wieslander, J., Timoneda, J., McKinney, P., Butkowski, R. J., Wisdom, B. J., Jr., and Hudson, B. G. (1988) *J Biol Chem* 263(21), 10481–8
56. Uitto, J., and Prockop, D. J. (1973) *Biochem. Biophys. Res. Commun.* 55, 904–911
57. Siebold, B., Deutzmann, R., and Kuhn, K. (1988) *Eur J Biochem* 176(3), 617–24
58. Hohenester, E., Sasaki, T., Olsen, B. R., and Timpl, R. (1998) *Embo J.* 17, 1656–1664
59. Sasaki, T., Larsson, H., Tisi, D., Claesson-Welsh, L., Hohenester, E., and Timpl, R. (2000) *J. Mol. Biol.* 301, 1179–1190
60. Petitclerc, E., Boutaud, A., Prestayko, A., Xu, J., Sado, Y., Ninomiya, Y., Sarras, M. P., Jr., Hudson, B. G., and Brooks, P. C. (2000) *J Biol Chem* 275(11), 8051–61
61. Laskowski, R. A., MacArthur, M. W., Moss, D. S., and Thornton, J. M. (1993) *J. Appl. Cryst.* 26, 283–291
62. Barton, G. J. (1993) *Prot. Eng.* 6, 37–40

We claim:

1. A polypeptide consisting of a sequence of a general formula selected from the group consisting of:

(a) General formula I:

PF(R1)(R2)CN(R3)(R4)(R5)VC(R6)(R7)A (SEQ ID NO: 1)

R1 is selected from the group consisting of L, M, A, V, norL, and I;

R2 is selected from the group consisting of F and Y;

R3 is selected from the group consisting of I, V, L, norL, A, and P;

R4 is selected from the group consisting of N, G, and H;

R5 is selected from the group consisting of N, D, Q, and E;

R6 is selected from the group consisting of N, Y, and H; and

R7 is selected from the group consisting of F and Y.

2. A polypeptide consisting of an amino acid sequence selected from the group consisting of:

PFLFCNINNVCNFASRND (SEQ ID NO: 259);
PFLFCNVNDVCNFASRND (SEQ ID NO: 260);
PFMFCNINNVCNFASRND (SEQ ID NO: 261);
PFLYCNPGDVCYYASRND (SEQ ID NO: 262);
PFAYCNIHQVCHYAQRND (SEQ ID NO: 263);
PFIYCNINEVCHYARRND (SEQ ID NO: 264);
LRKFSTMPFLFCNINNVCNF (SEQ ID NO: 288);
LQRFTTMPFLFCNVNDVCNF (SEQ ID NO:289);
LRRFSTMPFMFCNINVCNF (SEQ ID NO: 290);
LARFSTMPFLYCNPGDVCYY (SEQ ID NO: 291);
LPVFSTLPFAYCNIHQVCHY (SEQ ID NO: 292);
LPRFSTMPFIYCNINEVCHY (SEQ ID NO: 293);
FCNVNDVCNF (SEQ ID NO:298);
YCNPGDVCYY (SEQ ID NO:299);
YCNIHQVCHY (SEQ ID NO:300); and
YCNINEVCHY (SEQ ID NO:301).

3. A pharmaceutical composition comprising:

(a) the polypeptide of claim 1; and (b) a pharmaceutically acceptable carrier.

4. A pharmaceutical composition comprising:

(a) the polypeptide of claim 2; and (b) a pharmaceutically acceptable carrier.

5. A polypeptide of claim 1 selected from the group consisting of

PFLFCNINNVCNFA (SEQ ID NO:2);
PFLFCNVNDVCNFA (SEQ ID NO:3);
PFMFCNINNVCNFA (SEQ ID NO:4);
PFLYCNPGDVCYYA (SEQ ID NO:5);
PFAYCNIHQVCHYA (SEQ ID NO:6); and
PFIYCNINEVCHYA (SEQ ID NO:7).

6. A method for inhibiting angiogenesis in tissue comprising contacting said tissue with an effective inhibiting amount of the polypeptide of claim 1.

7. A method for inhibiting angiogenesis in tissue comprising contacting said tissue with an effective inhibiting amount of the polypeptide of claim 2.

8. A method for inhibiting tumor growth in a tissue in vivo comprising contacting the tissue with an amount effective to inhibit tumor growth of the polypeptide of claim 1.

9. A method for inhibiting tumor growth in a tissue in vivo comprising contacting the tissue with an amount effective to inhibit tumor growth of the polypeptide of claim 2.

* * * * *

SEQUENCE LISTING

```
<160> NUMBER OF SEQ ID NOS: 307

<210> SEQ ID NO 1
<211> LENGTH: 14
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X stands for leucine, methionine, alanine,
                        valine, norleucine, or isoleucine.
<220> FEATURE:
<221> NAME/KEY: MISC_FEATURE
<222> LOCATION: (4)..(4)
<223> OTHER INFORMATION: X stands for phenylalanine or tyrosine.
<220> FEATURE:
<221> NAME/KEY: MISC_FEATURE
<222> LOCATION: (7)..(7)
<223> OTHER INFORMATION: X stands for isoleucine, valine, leucine,
                        norleucine, alanine, or proline.
<220> FEATURE:
<221> NAME/KEY: MISC_FEATURE
<222> LOCATION: (8)..(8)
<223> OTHER INFORMATION: X stands for asparagine, glycine, or histidine.
<220> FEATURE:
<221> NAME/KEY: MISC_FEATURE
<222> LOCATION: (9)..(9)
<223> OTHER INFORMATION: X stands for glutamine, aspartate, asparagine,
                        and glutamate.
<220> FEATURE:
<221> NAME/KEY: MISC_FEATURE
<222> LOCATION: (12)..(12)
<223> OTHER INFORMATION: X stands for asparagine, tyrosine, or
                        histidine.
<220> FEATURE:
<221> NAME/KEY: MISC_FEATURE
<222> LOCATION: (13)..(13)
<223> OTHER INFORMATION: X stands for phenylalanine or tyrosine.

<400> SEQUENCE: 1

Pro Phe Xaa Xaa Cys Asn Xaa Xaa Xaa Val Cys Xaa Xaa Ala
1               5                   10

<210> SEQ ID NO 2
<211> LENGTH: 14
<212> TYPE: PRT
<213> ORGANISM: Homo sapiens

<400> SEQUENCE: 2
```

```
Pro Phe Leu Phe Cys Asn Ile Asn Asn Val Cys Asn Phe Ala
1               5                   10
```

<210> SEQ ID NO 3
<211> LENGTH: 14
<212> TYPE: PRT
<213> ORGANISM: Homo sapiens

<400> SEQUENCE: 3

```
Pro Phe Leu Phe Cys Asn Val Asn Asp Val Cys Asn Phe Ala
1               5                   10
```

<210> SEQ ID NO 4
<211> LENGTH: 14
<212> TYPE: PRT
<213> ORGANISM: Homo sapiens

<400> SEQUENCE: 4

```
Pro Phe Met Phe Cys Asn Ile Asn Asn Val Cys Asn Phe Ala
1               5                   10
```

<210> SEQ ID NO 5
<211> LENGTH: 14
<212> TYPE: PRT
<213> ORGANISM: Homo sapiens

<400> SEQUENCE: 5

```
Pro Phe Leu Tyr Cys Asn Pro Gly Asp Val Cys Tyr Tyr Ala
1               5                   10
```

<210> SEQ ID NO 6
<211> LENGTH: 14
<212> TYPE: PRT
<213> ORGANISM: Homo sapiens

<400> SEQUENCE: 6

```
Pro Phe Ala Tyr Cys Asn Ile His Gln Val Cys His Tyr Ala
1               5                   10
```

<210> SEQ ID NO 7
<211> LENGTH: 14
<212> TYPE: PRT
<213> ORGANISM: Homo sapiens

<400> SEQUENCE: 7

```
Pro Phe Ile Tyr Cys Asn Ile Asn Glu Val Cys His Tyr Ala
1               5                   10
```

<210> SEQ ID NO 8
<211> LENGTH: 13
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X stands for leucine, alanine, valine,
      norleucine, or isoleucine.
<220> FEATURE:
<221> NAME/KEY: MISC_FEATURE
<222> LOCATION: (6)..(6)
<223> OTHER INFORMATION: X stands for histidine, asparagine, glutamine,
      or serine.
<220> FEATURE:
<221> NAME/KEY: MISC_FEATURE
<222> LOCATION: (8)..(8)
<223> OTHER INFORMATION: X stands for glycine, arginine, alanine, or is
      absent.
<220> FEATURE:

-continued

```
<221> NAME/KEY: MISC_FEATURE
<222> LOCATION: (9)..(9)
<223> OTHER INFORMATION: X stands for arginine or glutamine.
<220> FEATURE:
<221> NAME/KEY: MISC_FEATURE
<222> LOCATION: (13)..(13)
<223> OTHER INFORMATION: X stands for asparagine or histidine.

<400> SEQUENCE: 8

Pro Phe Xaa Glu Cys Xaa Gly Xaa Xaa Gly Thr Cys Xaa
1               5                   10

<210> SEQ ID NO 9
<211> LENGTH: 12
<212> TYPE: PRT
<213> ORGANISM: Homo sapiens

<400> SEQUENCE: 9

Pro Phe Ile Glu Cys His Gly Arg Gly Thr Cys Asn
1               5                   10

<210> SEQ ID NO 10
<211> LENGTH: 12
<212> TYPE: PRT
<213> ORGANISM: Homo sapiens

<400> SEQUENCE: 10

Pro Phe Leu Glu Cys His Gly Arg Gly Thr Cys Asn
1               5                   10

<210> SEQ ID NO 11
<211> LENGTH: 13
<212> TYPE: PRT
<213> ORGANISM: Homo sapiens

<400> SEQUENCE: 11

Pro Phe Ile Glu Cys Asn Gly Gly Arg Gly Thr Cys His
1               5                   10

<210> SEQ ID NO 12
<211> LENGTH: 13
<212> TYPE: PRT
<213> ORGANISM: Homo sapiens

<400> SEQUENCE: 12

Pro Phe Leu Glu Cys Gln Gly Arg Gln Gly Thr Cys His
1               5                   10

<210> SEQ ID NO 13
<211> LENGTH: 13
<212> TYPE: PRT
<213> ORGANISM: Homo sapiens

<400> SEQUENCE: 13

Pro Phe Ile Glu Cys Ser Gly Ala Arg Gly Thr Cys His
1               5                   10

<210> SEQ ID NO 14
<211> LENGTH: 22
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Amino acids at positions 1-5 are optionally
                         absent, such that if 5 is absent, 1-4 are
                         absent, if 4 is absent, 1-3 are absent, etc.
```

```
<220> FEATURE:
<221> NAME/KEY: MISC_FEATURE
<222> LOCATION: (18)..(22)
<223> OTHER INFORMATION: Amino acids at positions 18-22 are optionally
                         absent, such that if 18 is absent, 19-22 are
                         absent, if 19 is absent, 20-22 are absent, etc.

<400> SEQUENCE: 14

Glu Phe Arg Ser Ala Pro Phe Ile Glu Cys His Gly Arg Gly Thr Cys
1               5                   10                  15

Asn Tyr Tyr Ala Asn Ala
            20

<210> SEQ ID NO 15
<211> LENGTH: 22
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Amino acids at positions 1-5 are optionally
                         absent, such that if 5 is absent, 1-4 are
                         absent, if 4 is absent, 1-3 are absent, etc.
<220> FEATURE:
<221> NAME/KEY: MISC_FEATURE
<222> LOCATION: (18)..(22)
<223> OTHER INFORMATION: Amino acids at positions 18-22 are optionally
                         absent, such that if 18 is absent, 19-22 are
                         absent, if 19 is absent, 20-22 are absent, etc.

<400> SEQUENCE: 15

Glu Phe Arg Ala Ser Pro Phe Leu Glu Cys His Gly Arg Gly Thr Cys
1               5                   10                  15

Asn Tyr Tyr Ser Asn Ser
            20

<210> SEQ ID NO 16
<211> LENGTH: 22
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Amino acids at positions 1-5 are optionally
                         absent, such that if 5 is absent, 1-4 are
                         absent, if 4 is absent, 1-3 are absent, etc.
<220> FEATURE:
<221> NAME/KEY: MISC_FEATURE
<222> LOCATION: (18)..(22)
<223> OTHER INFORMATION: Amino acids at positions 18-22 are optionally
                         absent, such that if 18 is absent, 19-22 are
                         absent, if 19 is absent, 20-22 are absent, etc.

<400> SEQUENCE: 16

Glu Phe Arg Ser Ala Pro Phe Ile Glu Cys His Gly Arg Gly Thr Cys
1               5                   10                  15

Asn Tyr Tyr Ala Asn Ser
            20

<210> SEQ ID NO 17
<211> LENGTH: 23
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Amino acids at positions 1-5 are optionally
                         absent, such that if 5 is absent, 1-4 are
                         absent, if 4 is absent, 1-3 are absent, etc.
<220> FEATURE:
```

```
<221> NAME/KEY: MISC_FEATURE
<222> LOCATION: (19)..(23)
<223> OTHER INFORMATION: Amino acids at positions 19-23 are optionally
                        absent, such that if 19 is absent, 20-23 are
                        absent, if 20 is absent, 21-23 are absent, etc.

<400> SEQUENCE: 17

Asp Phe Arg Ala Thr Pro Phe Ile Glu Cys Asn Gly Gly Arg Gly Thr
1               5                   10                  15

Cys His Tyr Tyr Ala Asn Lys
            20

<210> SEQ ID NO 18
<211> LENGTH: 23
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Amino acids at positions 1-5 are optionally
                        absent, such that if 5 is absent, 1-4 are
                        absent, if 4 is absent, 1-3 are absent, etc.
<220> FEATURE:
<221> NAME/KEY: MISC_FEATURE
<222> LOCATION: (19)..(23)
<223> OTHER INFORMATION: Amino acids at positions 19-23 are optionally
                        absent, such that if 19 is absent, 20-23 are
                        absent, if 20 is absent, 21-23 are absent, etc.

<400> SEQUENCE: 18

Asp Phe Arg Ala Ala Pro Phe Leu Glu Cys Gln Gly Arg Gln Gly Thr
1               5                   10                  15

Cys His Phe Phe Ala Asn Lys
            20

<210> SEQ ID NO 19
<211> LENGTH: 23
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: Amino acids at positions 1-5 are optionally
                        absent, such that if 5 is absent, 1-4 are
                        absent, if 4 is absent, 1-3 are absent, etc.
<220> FEATURE:
<221> NAME/KEY: MISC_FEATURE
<222> LOCATION: (19)..(23)
<223> OTHER INFORMATION: Amino acids at positions 19-23 are optionally
                        absent, such that if 19 is absent, 20-23 are
                        absent, if 20 is absent, 21-23 are absent, etc.

<400> SEQUENCE: 19

Asp Phe Arg Ala Thr Pro Phe Ile Glu Cys Ser Gly Ala Arg Gly Thr
1               5                   10                  15

Cys His Tyr Phe Ala Asn Lys
            20

<210> SEQ ID NO 20
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X stands for serine or threonine.
<220> FEATURE:
<221> NAME/KEY: MISC_FEATURE
<222> LOCATION: (4)..(4)
<223> OTHER INFORMATION: X stands for methionine and leucine.
```

-continued

<400> SEQUENCE: 20

Phe Xaa Thr Xaa
1

<210> SEQ ID NO 21
<211> LENGTH: 4
<212> TYPE: PRT
<213> ORGANISM: Homo sapiens

<400> SEQUENCE: 21

Phe Ser Thr Met
1

<210> SEQ ID NO 22
<211> LENGTH: 4
<212> TYPE: PRT
<213> ORGANISM: Homo sapiens

<400> SEQUENCE: 22

Phe Thr Thr Met
1

<210> SEQ ID NO 23
<211> LENGTH: 4
<212> TYPE: PRT
<213> ORGANISM: Homo sapiens

<400> SEQUENCE: 23

Phe Thr Ser Leu
1

<210> SEQ ID NO 24
<211> LENGTH: 5
<212> TYPE: PRT
<213> ORGANISM: Homo sapiens

<400> SEQUENCE: 24

Ser Cys Leu Arg Lys
1               5

<210> SEQ ID NO 25
<211> LENGTH: 5
<212> TYPE: PRT
<213> ORGANISM: Homo sapiens

<400> SEQUENCE: 25

Pro Phe Leu Phe Cys
1               5

<210> SEQ ID NO 26
<211> LENGTH: 14
<212> TYPE: PRT
<213> ORGANISM: Homo sapiens

<400> SEQUENCE: 26

Ser Cys Leu Arg Lys Phe Ser Thr Met Pro Phe Leu Phe Cys
1               5                   10

<210> SEQ ID NO 27
<211> LENGTH: 5
<212> TYPE: PRT
<213> ORGANISM: Homo sapiens

<400> SEQUENCE: 27

```
Ser Cys Leu Gln Arg
1               5

<210> SEQ ID NO 28
<211> LENGTH: 14
<212> TYPE: PRT
<213> ORGANISM: Homo sapiens

<400> SEQUENCE: 28

Ser Cys Leu Gln Arg Phe Thr Thr Met Pro Phe Leu Phe Cys
1               5                   10

<210> SEQ ID NO 29
<211> LENGTH: 5
<212> TYPE: PRT
<213> ORGANISM: Homo sapiens

<400> SEQUENCE: 29

Ser Cys Leu Arg Arg
1               5

<210> SEQ ID NO 30
<211> LENGTH: 5
<212> TYPE: PRT
<213> ORGANISM: Homo sapiens

<400> SEQUENCE: 30

Pro Phe Met Phe Cys
1               5

<210> SEQ ID NO 31
<211> LENGTH: 14
<212> TYPE: PRT
<213> ORGANISM: Homo sapiens

<400> SEQUENCE: 31

Ser Cys Leu Arg Arg Phe Ser Thr Met Pro Phe Met Phe Cys
1               5                   10

<210> SEQ ID NO 32
<211> LENGTH: 5
<212> TYPE: PRT
<213> ORGANISM: Homo sapiens

<400> SEQUENCE: 32

Ser Cys Leu Ala Arg
1               5

<210> SEQ ID NO 33
<211> LENGTH: 5
<212> TYPE: PRT
<213> ORGANISM: Homo sapiens

<400> SEQUENCE: 33

Pro Phe Leu Tyr Cys
1               5

<210> SEQ ID NO 34
<211> LENGTH: 14
<212> TYPE: PRT
<213> ORGANISM: Homo sapiens

<400> SEQUENCE: 34

Ser Cys Leu Ala Arg Phe Ser Thr Met Pro Phe Leu Tyr Cys
```

<210> SEQ ID NO 35
<211> LENGTH: 5
<212> TYPE: PRT
<213> ORGANISM: Homo sapiens

<400> SEQUENCE: 35

Ser Cys Leu Pro Val
1               5

<210> SEQ ID NO 36
<211> LENGTH: 5
<212> TYPE: PRT
<213> ORGANISM: Homo sapiens

<400> SEQUENCE: 36

Pro Phe Ala Tyr Cys
1               5

<210> SEQ ID NO 37
<211> LENGTH: 14
<212> TYPE: PRT
<213> ORGANISM: Homo sapiens

<400> SEQUENCE: 37

Ser Cys Leu Pro Val Phe Ser Thr Leu Pro Phe Ala Tyr Cys
1               5                  10

<210> SEQ ID NO 38
<211> LENGTH: 5
<212> TYPE: PRT
<213> ORGANISM: Homo sapiens

<400> SEQUENCE: 38

Ser Cys Leu Pro Arg
1               5

<210> SEQ ID NO 39
<211> LENGTH: 5
<212> TYPE: PRT
<213> ORGANISM: Homo sapiens

<400> SEQUENCE: 39

Pro Phe Ile Tyr Cys
1               5

<210> SEQ ID NO 40
<211> LENGTH: 14
<212> TYPE: PRT
<213> ORGANISM: Homo sapiens

<400> SEQUENCE: 40

Ser Cys Leu Pro Arg Phe Ser Thr Met Pro Phe Ile Tyr Cys
1               5                  10

<210> SEQ ID NO 41
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X stands for glutamate, arginine, or aspartate.
<220> FEATURE:
<221> NAME/KEY: MISC_FEATURE

```
<222> LOCATION: (4)..(4)
<223> OTHER INFORMATION: X stands for lysine, arginine, or serine.

<400> SEQUENCE: 41

Xaa Met Phe Xaa Lys
1               5

<210> SEQ ID NO 42
<211> LENGTH: 5
<212> TYPE: PRT
<213> ORGANISM: Homo sapiens

<400> SEQUENCE: 42

Glu Met Phe Lys Lys
1               5

<210> SEQ ID NO 43
<211> LENGTH: 5
<212> TYPE: PRT
<213> ORGANISM: Homo sapiens

<400> SEQUENCE: 43

Arg Met Phe Arg Lys
1               5

<210> SEQ ID NO 44
<211> LENGTH: 5
<212> TYPE: PRT
<213> ORGANISM: Homo sapiens

<400> SEQUENCE: 44

Asp Met Phe Ser Lys
1               5

<210> SEQ ID NO 45
<211> LENGTH: 3
<212> TYPE: PRT
<213> ORGANISM: Homo sapiens

<400> SEQUENCE: 45

Ser Phe Gln
1

<210> SEQ ID NO 46
<211> LENGTH: 3
<212> TYPE: PRT
<213> ORGANISM: Homo sapiens

<400> SEQUENCE: 46

Leu Gln Phe
1

<210> SEQ ID NO 47
<211> LENGTH: 3
<212> TYPE: PRT
<213> ORGANISM: Homo sapiens

<400> SEQUENCE: 47

Gln Gln Phe
1

<210> SEQ ID NO 48
<211> LENGTH: 5
<212> TYPE: PRT
<213> ORGANISM: Homo sapiens
```

```
<400> SEQUENCE: 48

Thr Ile Glu Arg Ser
1               5

<210> SEQ ID NO 49
<211> LENGTH: 5
<212> TYPE: PRT
<213> ORGANISM: Homo sapiens

<400> SEQUENCE: 49

Pro Thr Pro Ser Thr
1               5

<210> SEQ ID NO 50
<211> LENGTH: 15
<212> TYPE: PRT
<213> ORGANISM: Homo sapiens

<400> SEQUENCE: 50

Thr Ile Glu Arg Ser Glu Met Phe Lys Lys Pro Thr Pro Ser Thr
1               5                  10                  15

<210> SEQ ID NO 51
<211> LENGTH: 5
<212> TYPE: PRT
<213> ORGANISM: Homo sapiens

<400> SEQUENCE: 51

Ser Leu Asn Pro Glu
1               5

<210> SEQ ID NO 52
<211> LENGTH: 5
<212> TYPE: PRT
<213> ORGANISM: Homo sapiens

<400> SEQUENCE: 52

Pro Ile Pro Ser Thr
1               5

<210> SEQ ID NO 53
<211> LENGTH: 15
<212> TYPE: PRT
<213> ORGANISM: Homo sapiens

<400> SEQUENCE: 53

Ser Leu Asn Pro Glu Arg Met Phe Arg Lys Pro Ile Pro Ser Thr
1               5                  10                  15

<210> SEQ ID NO 54
<211> LENGTH: 5
<212> TYPE: PRT
<213> ORGANISM: Homo sapiens

<400> SEQUENCE: 54

Thr Val Asp Val Ser
1               5

<210> SEQ ID NO 55
<211> LENGTH: 5
<212> TYPE: PRT
<213> ORGANISM: Homo sapiens

<400> SEQUENCE: 55
```

Pro Gln Ser Glu Thr
1               5

<210> SEQ ID NO 56
<211> LENGTH: 15
<212> TYPE: PRT
<213> ORGANISM: Homo sapiens

<400> SEQUENCE: 56

Thr Val Asp Val Ser Asp Met Phe Ser Lys Pro Gln Ser Glu Thr
1               5                   10                  15

<210> SEQ ID NO 57
<211> LENGTH: 5
<212> TYPE: PRT
<213> ORGANISM: Homo sapiens

<400> SEQUENCE: 57

Thr Ile Pro Glu Gln
1               5

<210> SEQ ID NO 58
<211> LENGTH: 5
<212> TYPE: PRT
<213> ORGANISM: Homo sapiens

<400> SEQUENCE: 58

Gly Ser Pro Ser Ala
1               5

<210> SEQ ID NO 59
<211> LENGTH: 13
<212> TYPE: PRT
<213> ORGANISM: Homo sapiens

<400> SEQUENCE: 59

Thr Ile Pro Glu Gln Ser Phe Gln Gly Ser Pro Ser Ala
1               5                   10

<210> SEQ ID NO 60
<211> LENGTH: 5
<212> TYPE: PRT
<213> ORGANISM: Homo sapiens

<400> SEQUENCE: 60

Thr Val Lys Ala Asp
1               5

<210> SEQ ID NO 61
<211> LENGTH: 5
<212> TYPE: PRT
<213> ORGANISM: Homo sapiens

<400> SEQUENCE: 61

Ser Ser Ala Pro Ala
1               5

<210> SEQ ID NO 62
<211> LENGTH: 13
<212> TYPE: PRT
<213> ORGANISM: Homo sapiens

<400> SEQUENCE: 62

Thr Val Lys Ala Asp Leu Gln Phe Ser Ser Ala Pro Ala 1               5                    10

<210> SEQ ID NO 63
<211> LENGTH: 5
<212> TYPE: PRT
<213> ORGANISM: Homo sapiens

<400> SEQUENCE: 63

Thr Val Glu Glu Arg
1               5

<210> SEQ ID NO 64
<211> LENGTH: 5
<212> TYPE: PRT
<213> ORGANISM: Homo sapiens

<400> SEQUENCE: 64

Gly Glu Leu Pro Val
1               5

<210> SEQ ID NO 65
<211> LENGTH: 13
<212> TYPE: PRT
<213> ORGANISM: Homo sapiens

<400> SEQUENCE: 65

Thr Val Glu Glu Arg Gln Gln Phe Gly Glu Leu Pro Val
1               5                   10

<210> SEQ ID NO 66
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X stands for arginine or lysine.
<220> FEATURE:
<221> NAME/KEY: MISC_FEATURE
<222> LOCATION: (4)..(4)
<223> OTHER INFORMATION: X stands for glycine or asparagine.

<400> SEQUENCE: 66

Xaa Ala His Xaa Gln Asp
1               5

<210> SEQ ID NO 67
<211> LENGTH: 5
<212> TYPE: PRT
<213> ORGANISM: Homo sapiens

<400> SEQUENCE: 67

Arg Ala His Gly Gln
1               5

<210> SEQ ID NO 68
<211> LENGTH: 6
<212> TYPE: PRT
<213> ORGANISM: Homo sapiens

<400> SEQUENCE: 68

Lys Ala His Asn Gln Asp
1               5

<210> SEQ ID NO 69
<211> LENGTH: 5

<212> TYPE: PRT
<213> ORGANISM: Homo sapiens

<400> SEQUENCE: 69

Val Gln Gly Asn Glu
1               5

<210> SEQ ID NO 70
<211> LENGTH: 5
<212> TYPE: PRT
<213> ORGANISM: Homo sapiens

<400> SEQUENCE: 70

Leu Gly Thr Ala Gly
1               5

<210> SEQ ID NO 71
<211> LENGTH: 16
<212> TYPE: PRT
<213> ORGANISM: Homo sapiens

<400> SEQUENCE: 71

Val Gln Gly Asn Glu Arg Ala His Gly Gln Asp Asp Leu Gly Thr Ala
1               5                   10                  15

<210> SEQ ID NO 72
<211> LENGTH: 5
<212> TYPE: PRT
<213> ORGANISM: Homo sapiens

<400> SEQUENCE: 72

Val Gln Gly Asn Gln
1               5

<210> SEQ ID NO 73
<211> LENGTH: 5
<212> TYPE: PRT
<213> ORGANISM: Homo sapiens

<400> SEQUENCE: 73

Leu Gly Thr Leu Gly
1               5

<210> SEQ ID NO 74
<211> LENGTH: 16
<212> TYPE: PRT
<213> ORGANISM: Homo sapiens

<400> SEQUENCE: 74

Val Gln Gly Asn Gln Arg Ala His Gly Gln Asp Leu Gly Thr Leu Gly
1               5                   10                  15

<210> SEQ ID NO 75
<211> LENGTH: 5
<212> TYPE: PRT
<213> ORGANISM: Homo sapiens

<400> SEQUENCE: 75

Val Gln Gly Asn Lys
1               5

<210> SEQ ID NO 76
<211> LENGTH: 16
<212> TYPE: PRT
<213> ORGANISM: Homo sapiens

```
<400> SEQUENCE: 76

Val Gln Gly Asn Lys Arg Ala His Gly Gln Asp Leu Gly Thr Ala Gly
 1               5                  10                  15

<210> SEQ ID NO 77
<211> LENGTH: 5
<212> TYPE: PRT
<213> ORGANISM: Homo sapiens

<400> SEQUENCE: 77

Phe Glu Gly Gln Glu
 1               5

<210> SEQ ID NO 78
<211> LENGTH: 5
<212> TYPE: PRT
<213> ORGANISM: Homo sapiens

<400> SEQUENCE: 78

Leu Gly Leu Ala Gly
 1               5

<210> SEQ ID NO 79
<211> LENGTH: 16
<212> TYPE: PRT
<213> ORGANISM: Homo sapiens

<400> SEQUENCE: 79

Phe Glu Gly Gln Glu Lys Ala His Asn Gln Asp Leu Gly Leu Ala Gly
 1               5                  10                  15

<210> SEQ ID NO 80
<211> LENGTH: 5
<212> TYPE: PRT
<213> ORGANISM: Homo sapiens

<400> SEQUENCE: 80

Leu Glu Gly Gln Glu
 1               5

<210> SEQ ID NO 81
<211> LENGTH: 16
<212> TYPE: PRT
<213> ORGANISM: Homo sapiens

<400> SEQUENCE: 81

Leu Glu Gly Gln Glu Lys Ala His Asn Gln Asp Leu Gly Leu Ala Gly
 1               5                  10                  15

<210> SEQ ID NO 82
<211> LENGTH: 5
<212> TYPE: PRT
<213> ORGANISM: Homo sapiens

<400> SEQUENCE: 82

Val Glu Gly Gln Glu
 1               5

<210> SEQ ID NO 83
<211> LENGTH: 5
<212> TYPE: PRT
<213> ORGANISM: Homo sapiens

<400> SEQUENCE: 83
```

```
Leu Gly Phe Ala Gly
 1               5

<210> SEQ ID NO 84
<211> LENGTH: 16
<212> TYPE: PRT
<213> ORGANISM: Homo sapiens

<400> SEQUENCE: 84

Val Glu Gly Gln Glu Lys Ala His Asn Gln Asp Leu Gly Phe Ala Gly
 1               5                  10                  15

<210> SEQ ID NO 85
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X stands for glutamate or glutamine.
<220> FEATURE:
<221> NAME/KEY: MISC_FEATURE
<222> LOCATION: (3)..(3)
<223> OTHER INFORMATION: X stands for serine, threonine, or glycine.

<400> SEQUENCE: 85

Xaa Gly Xaa Gly Gln
 1               5

<210> SEQ ID NO 86
<211> LENGTH: 5
<212> TYPE: PRT
<213> ORGANISM: Homo sapiens

<400> SEQUENCE: 86

Glu Gly Ser Gly Gln
 1               5

<210> SEQ ID NO 87
<211> LENGTH: 5
<212> TYPE: PRT
<213> ORGANISM: Homo sapiens

<400> SEQUENCE: 87

Glu Gly Thr Gly Gln
 1               5

<210> SEQ ID NO 88
<211> LENGTH: 5
<212> TYPE: PRT
<213> ORGANISM: Homo sapiens

<400> SEQUENCE: 88

Glu Gly Gly Gly Gln
 1               5

<210> SEQ ID NO 89
<211> LENGTH: 5
<212> TYPE: PRT
<213> ORGANISM: Homo sapiens

<400> SEQUENCE: 89

Gln Gly Gly Gly Gln
 1               5
```

```
<210> SEQ ID NO 90
<211> LENGTH: 5
<212> TYPE: PRT
<213> ORGANISM: Homo sapiens

<400> SEQUENCE: 90

Thr Ser Ala Gly Ala
1               5

<210> SEQ ID NO 91
<211> LENGTH: 5
<212> TYPE: PRT
<213> ORGANISM: Homo sapiens

<400> SEQUENCE: 91

Ala Leu Ala Ser Pro
1               5

<210> SEQ ID NO 92
<211> LENGTH: 15
<212> TYPE: PRT
<213> ORGANISM: Homo sapiens

<400> SEQUENCE: 92

Thr Ser Ala Gly Ala Glu Gly Ser Gly Gln Ala Leu Ala Ser Pro
1               5                   10                  15

<210> SEQ ID NO 93
<211> LENGTH: 5
<212> TYPE: PRT
<213> ORGANISM: Homo sapiens

<400> SEQUENCE: 93

Thr Ser Ala Gly Ser
1               5

<210> SEQ ID NO 94
<211> LENGTH: 15
<212> TYPE: PRT
<213> ORGANISM: Homo sapiens

<400> SEQUENCE: 94

Thr Ser Ala Gly Ser Glu Gly Thr Gly Gln Ala Leu Ala Ser Pro
1               5                   10                  15

<210> SEQ ID NO 95
<211> LENGTH: 5
<212> TYPE: PRT
<213> ORGANISM: Homo sapiens

<400> SEQUENCE: 95

Thr Ala Ala Gly Asp
1               5

<210> SEQ ID NO 96
<211> LENGTH: 5
<212> TYPE: PRT
<213> ORGANISM: Homo sapiens

<400> SEQUENCE: 96

Ser Leu Val Ser Pro
1               5

<210> SEQ ID NO 97
<211> LENGTH: 15
```

<212> TYPE: PRT
<213> ORGANISM: Homo sapiens

<400> SEQUENCE: 97

Thr Ala Ala Gly Asp Glu Gly Gly Gly Gln Ser Leu Val Ser Pro
1               5                   10                  15

<210> SEQ ID NO 98
<211> LENGTH: 5
<212> TYPE: PRT
<213> ORGANISM: Homo sapiens

<400> SEQUENCE: 98

Thr Gly Ala Gly Asp
1               5

<210> SEQ ID NO 99
<211> LENGTH: 5
<212> TYPE: PRT
<213> ORGANISM: Homo sapiens

<400> SEQUENCE: 99

Ala Leu Met Ser Pro
1               5

<210> SEQ ID NO 100
<211> LENGTH: 15
<212> TYPE: PRT
<213> ORGANISM: Homo sapiens

<400> SEQUENCE: 100

Thr Gly Ala Gly Asp Gln Gly Gly Gly Gln Ala Leu Met Ser Pro
1               5                   10                  15

<210> SEQ ID NO 101
<211> LENGTH: 5
<212> TYPE: PRT
<213> ORGANISM: Homo sapiens

<400> SEQUENCE: 101

Thr Ala Ala Gly Ala
1               5

<210> SEQ ID NO 102
<211> LENGTH: 15
<212> TYPE: PRT
<213> ORGANISM: Homo sapiens

<400> SEQUENCE: 102

Thr Ala Ala Gly Ala Glu Gly Gly Gly Gln Ser Leu Val Ser Pro
1               5                   10                  15

<210> SEQ ID NO 103
<211> LENGTH: 4
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X stands for glutamine or glutamate.
<220> FEATURE:
<221> NAME/KEY: MISC_FEATURE
<222> LOCATION: (3)..(3)
<223> OTHER INFORMATION: X stands for asparagine or glutamine.
<220> FEATURE:
<221> NAME/KEY: MISC_FEATURE
<222> LOCATION: (4)..(4)

```
<223> OTHER INFORMATION: X stands for gluatamate, glutamine, or lysine.

<400> SEQUENCE: 103

Xaa Gly Xaa Xaa
1

<210> SEQ ID NO 104
<211> LENGTH: 4
<212> TYPE: PRT
<213> ORGANISM: Homo sapiens

<400> SEQUENCE: 104

Gln Gly Asn Glu
1

<210> SEQ ID NO 105
<211> LENGTH: 4
<212> TYPE: PRT
<213> ORGANISM: Homo sapiens

<400> SEQUENCE: 105

Gln Gly Asn Gln
1

<210> SEQ ID NO 106
<211> LENGTH: 4
<212> TYPE: PRT
<213> ORGANISM: Homo sapiens

<400> SEQUENCE: 106

Gln Gly Asn Lys
1

<210> SEQ ID NO 107
<211> LENGTH: 4
<212> TYPE: PRT
<213> ORGANISM: Homo sapiens

<400> SEQUENCE: 107

Glu Gly Gln Glu
1

<210> SEQ ID NO 108
<211> LENGTH: 5
<212> TYPE: PRT
<213> ORGANISM: Homo sapiens

<400> SEQUENCE: 108

Ser Leu Leu Tyr Val
1               5

<210> SEQ ID NO 109
<211> LENGTH: 5
<212> TYPE: PRT
<213> ORGANISM: Homo sapiens

<400> SEQUENCE: 109

Arg Ala His Gly Gln
1               5

<210> SEQ ID NO 110
<211> LENGTH: 14
<212> TYPE: PRT
<213> ORGANISM: Homo sapiens
```

```
<400> SEQUENCE: 110

Ser Leu Leu Tyr Val Gln Gly Asn Glu Arg Ala His Gly Gln
1               5                   10

<210> SEQ ID NO 111
<211> LENGTH: 5
<212> TYPE: PRT
<213> ORGANISM: Homo sapiens

<400> SEQUENCE: 111

Ser Phe Leu Phe Val
1               5

<210> SEQ ID NO 112
<211> LENGTH: 14
<212> TYPE: PRT
<213> ORGANISM: Homo sapiens

<400> SEQUENCE: 112

Ser Phe Leu Phe Val Gln Gly Asn Gln Arg Ala His Gly Gln
1               5                   10

<210> SEQ ID NO 113
<211> LENGTH: 14
<212> TYPE: PRT
<213> ORGANISM: Homo sapiens

<400> SEQUENCE: 113

Ser Leu Leu Tyr Val Gln Gly Asn Lys Arg Ala His Gly Gln
1               5                   10

<210> SEQ ID NO 114
<211> LENGTH: 5
<212> TYPE: PRT
<213> ORGANISM: Homo sapiens

<400> SEQUENCE: 114

Ser Leu Leu Tyr Phe
1               5

<210> SEQ ID NO 115
<211> LENGTH: 5
<212> TYPE: PRT
<213> ORGANISM: Homo sapiens

<400> SEQUENCE: 115

Lys Ala His Asn Gln
1               5

<210> SEQ ID NO 116
<211> LENGTH: 14
<212> TYPE: PRT
<213> ORGANISM: Homo sapiens

<400> SEQUENCE: 116

Ser Leu Leu Tyr Phe Glu Gly Gln Glu Lys Ala His Asn Gln
1               5                   10

<210> SEQ ID NO 117
<211> LENGTH: 5
<212> TYPE: PRT
<213> ORGANISM: Homo sapiens

<400> SEQUENCE: 117
```

```
Ser Leu Leu Tyr Leu
1               5

<210> SEQ ID NO 118
<211> LENGTH: 14
<212> TYPE: PRT
<213> ORGANISM: Homo sapiens

<400> SEQUENCE: 118

Ser Leu Leu Tyr Leu Glu Gly Gln Glu Lys Ala His Asn Gln
1               5                   10

<210> SEQ ID NO 119
<211> LENGTH: 5
<212> TYPE: PRT
<213> ORGANISM: Homo sapiens

<400> SEQUENCE: 119

Ser Leu Leu Phe Val
1               5

<210> SEQ ID NO 120
<211> LENGTH: 14
<212> TYPE: PRT
<213> ORGANISM: Homo sapiens

<400> SEQUENCE: 120

Ser Leu Leu Phe Val Glu Gly Gln Glu Lys Ala His Asn Gln
1               5                   10

<210> SEQ ID NO 121
<211> LENGTH: 6
<212> TYPE: PRT
<213> ORGANISM: Homo sapiens

<400> SEQUENCE: 121

Val Gln Gly Asn Glu Arg
1               5

<210> SEQ ID NO 122
<211> LENGTH: 6
<212> TYPE: PRT
<213> ORGANISM: Homo sapiens

<400> SEQUENCE: 122

Val Gln Gly Asn Gln Arg
1               5

<210> SEQ ID NO 123
<211> LENGTH: 6
<212> TYPE: PRT
<213> ORGANISM: Homo sapiens

<400> SEQUENCE: 123

Val Gln Gly Asn Lys Arg
1               5

<210> SEQ ID NO 124
<211> LENGTH: 6
<212> TYPE: PRT
<213> ORGANISM: Homo sapiens

<400> SEQUENCE: 124

Phe Glu Gly Gln Glu Lys
1               5
```

```
<210> SEQ ID NO 125
<211> LENGTH: 6
<212> TYPE: PRT
<213> ORGANISM: Homo sapiens

<400> SEQUENCE: 125

Leu Glu Gly Gln Glu Lys
1               5

<210> SEQ ID NO 126
<211> LENGTH: 6
<212> TYPE: PRT
<213> ORGANISM: Homo sapiens

<400> SEQUENCE: 126

Val Glu Gly Gln Glu Lys
1               5

<210> SEQ ID NO 127
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X stands for serine, asparagine, or is absent.
<220> FEATURE:
<221> NAME/KEY: MISC_FEATURE
<222> LOCATION: (4)..(4)
<223> OTHER INFORMATION: X stands for alanine, glutamine, or is absent.

<400> SEQUENCE: 127

Met Xaa Met Xaa Pro
1               5

<210> SEQ ID NO 128
<211> LENGTH: 5
<212> TYPE: PRT
<213> ORGANISM: Homo sapiens

<400> SEQUENCE: 128

Met Ser Met Ala Pro
1               5

<210> SEQ ID NO 129
<211> LENGTH: 5
<212> TYPE: PRT
<213> ORGANISM: Homo sapiens

<400> SEQUENCE: 129

Met Asn Met Ala Pro
1               5

<210> SEQ ID NO 130
<211> LENGTH: 5
<212> TYPE: PRT
<213> ORGANISM: Homo sapiens

<400> SEQUENCE: 130

Met Ser Met Gln Pro
1               5

<210> SEQ ID NO 131
<211> LENGTH: 3
<212> TYPE: PRT
```

<213> ORGANISM: Homo sapiens

<400> SEQUENCE: 131

Met Met Pro
1

<210> SEQ ID NO 132
<211> LENGTH: 5
<212> TYPE: PRT
<213> ORGANISM: Homo sapiens

<400> SEQUENCE: 132

Pro Glu Pro Met Pro
1               5

<210> SEQ ID NO 133
<211> LENGTH: 5
<212> TYPE: PRT
<213> ORGANISM: Homo sapiens

<400> SEQUENCE: 133

Ile Thr Gly Glu Asn
1               5

<210> SEQ ID NO 134
<211> LENGTH: 15
<212> TYPE: PRT
<213> ORGANISM: Homo sapiens

<400> SEQUENCE: 134

Pro Glu Pro Met Pro Met Ser Met Ala Pro Ile Thr Gly Glu Asn
1               5                   10                  15

<210> SEQ ID NO 135
<211> LENGTH: 5
<212> TYPE: PRT
<213> ORGANISM: Homo sapiens

<400> SEQUENCE: 135

Pro Ala Leu Met Pro
1               5

<210> SEQ ID NO 136
<211> LENGTH: 5
<212> TYPE: PRT
<213> ORGANISM: Homo sapiens

<400> SEQUENCE: 136

Ile Thr Gly Arg Ala
1               5

<210> SEQ ID NO 137
<211> LENGTH: 15
<212> TYPE: PRT
<213> ORGANISM: Homo sapiens

<400> SEQUENCE: 137

Pro Ala Leu Met Pro Met Asn Met Ala Pro Ile Thr Gly Arg Ala
1               5                   10                  15

<210> SEQ ID NO 138
<211> LENGTH: 5
<212> TYPE: PRT
<213> ORGANISM: Homo sapiens

```
<400> SEQUENCE: 138

Leu Lys Gly Gln Ser
1               5

<210> SEQ ID NO 139
<211> LENGTH: 15
<212> TYPE: PRT
<213> ORGANISM: Homo sapiens

<400> SEQUENCE: 139

Pro Glu Pro Met Pro Met Ser Met Gln Pro Leu Lys Gly Gln Ser
1               5                   10                  15

<210> SEQ ID NO 140
<211> LENGTH: 5
<212> TYPE: PRT
<213> ORGANISM: Homo sapiens

<400> SEQUENCE: 140

Thr Ala Pro Leu Pro
1               5

<210> SEQ ID NO 141
<211> LENGTH: 5
<212> TYPE: PRT
<213> ORGANISM: Homo sapiens

<400> SEQUENCE: 141

Val Ala Glu Asp Glu
1               5

<210> SEQ ID NO 142
<211> LENGTH: 13
<212> TYPE: PRT
<213> ORGANISM: Homo sapiens

<400> SEQUENCE: 142

Thr Ala Pro Leu Pro Met Met Pro Val Ala Glu Asp Glu
1               5                   10

<210> SEQ ID NO 143
<211> LENGTH: 5
<212> TYPE: PRT
<213> ORGANISM: Homo sapiens

<400> SEQUENCE: 143

Ala Ala Pro Leu Pro
1               5

<210> SEQ ID NO 144
<211> LENGTH: 5
<212> TYPE: PRT
<213> ORGANISM: Homo sapiens

<400> SEQUENCE: 144

Leu Ser Glu Glu Ala
1               5

<210> SEQ ID NO 145
<211> LENGTH: 13
<212> TYPE: PRT
<213> ORGANISM: Homo sapiens

<400> SEQUENCE: 145
```

Ala Ala Pro Leu Pro Met Met Pro Leu Ser Glu Glu Ala
1               5                   10

<210> SEQ ID NO 146
<211> LENGTH: 5
<212> TYPE: PRT
<213> ORGANISM: Homo sapiens

<400> SEQUENCE: 146

Thr Ala Pro Ile Pro
1               5

<210> SEQ ID NO 147
<211> LENGTH: 5
<212> TYPE: PRT
<213> ORGANISM: Homo sapiens

<400> SEQUENCE: 147

Val Ser Gln Thr Gln
1               5

<210> SEQ ID NO 148
<211> LENGTH: 13
<212> TYPE: PRT
<213> ORGANISM: Homo sapiens

<400> SEQUENCE: 148

Thr Ala Pro Ile Pro Met Met Pro Val Ser Gln Thr Gln
1               5                   10

<210> SEQ ID NO 149
<211> LENGTH: 11
<212> TYPE: PRT
<213> ORGANISM: Homo sapiens

<400> SEQUENCE: 149

Pro Met Pro Met Ser Met Ala Pro Ile Thr Gly
1               5                   10

<210> SEQ ID NO 150
<211> LENGTH: 11
<212> TYPE: PRT
<213> ORGANISM: Homo sapiens

<400> SEQUENCE: 150

Leu Met Pro Met Asn Met Ala Pro Ile Thr Gly
1               5                   10

<210> SEQ ID NO 151
<211> LENGTH: 11
<212> TYPE: PRT
<213> ORGANISM: Homo sapiens

<400> SEQUENCE: 151

Pro Met Pro Met Ser Met Gln Pro Leu Lys Gly
1               5                   10

<210> SEQ ID NO 152
<211> LENGTH: 9
<212> TYPE: PRT
<213> ORGANISM: Homo sapiens

<400> SEQUENCE: 152

Pro Leu Pro Met Met Pro Val Ala Glu
1               5

```
<210> SEQ ID NO 153
<211> LENGTH: 9
<212> TYPE: PRT
<213> ORGANISM: Homo sapiens

<400> SEQUENCE: 153

Pro Leu Pro Met Met Pro Leu Ser Glu
1               5

<210> SEQ ID NO 154
<211> LENGTH: 9
<212> TYPE: PRT
<213> ORGANISM: Homo sapiens

<400> SEQUENCE: 154

Pro Ile Pro Met Met Pro Val Ser Gln
1               5

<210> SEQ ID NO 155
<211> LENGTH: 4
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X stands for alanine, serine, or aspartate.
<220> FEATURE:
<221> NAME/KEY: MISC_FEATURE
<222> LOCATION: (4)..(4)
<223> OTHER INFORMATION: X stands for glutamate or glutamine.

<400> SEQUENCE: 155

Ala Gly Xaa Xaa
1

<210> SEQ ID NO 156
<211> LENGTH: 4
<212> TYPE: PRT
<213> ORGANISM: Homo sapiens

<400> SEQUENCE: 156

Ala Gly Ala Glu
1

<210> SEQ ID NO 157
<211> LENGTH: 4
<212> TYPE: PRT
<213> ORGANISM: Homo sapiens

<400> SEQUENCE: 157

Ala Gly Ser Glu
1

<210> SEQ ID NO 158
<211> LENGTH: 4
<212> TYPE: PRT
<213> ORGANISM: Homo sapiens

<400> SEQUENCE: 158

Ala Gly Asp Glu
1

<210> SEQ ID NO 159
<211> LENGTH: 4
<212> TYPE: PRT
```

```
<213> ORGANISM: Homo sapiens

<400> SEQUENCE: 159

Ala Gly Asp Gln
1

<210> SEQ ID NO 160
<211> LENGTH: 5
<212> TYPE: PRT
<213> ORGANISM: Homo sapiens

<400> SEQUENCE: 160

Val Met His Thr Ser
1               5

<210> SEQ ID NO 161
<211> LENGTH: 5
<212> TYPE: PRT
<213> ORGANISM: Homo sapiens

<400> SEQUENCE: 161

Gly Ser Gly Gln Ala
1               5

<210> SEQ ID NO 162
<211> LENGTH: 14
<212> TYPE: PRT
<213> ORGANISM: Homo sapiens

<400> SEQUENCE: 162

Val Met His Thr Ser Ala Gly Ala Glu Gly Ser Gly Gln Ala
1               5                   10

<210> SEQ ID NO 163
<211> LENGTH: 5
<212> TYPE: PRT
<213> ORGANISM: Homo sapiens

<400> SEQUENCE: 163

Ile Met Phe Thr Ser
1               5

<210> SEQ ID NO 164
<211> LENGTH: 5
<212> TYPE: PRT
<213> ORGANISM: Homo sapiens

<400> SEQUENCE: 164

Gly Thr Gly Gln Ala
1               5

<210> SEQ ID NO 165
<211> LENGTH: 14
<212> TYPE: PRT
<213> ORGANISM: Homo sapiens

<400> SEQUENCE: 165

Ile Met Phe Thr Ser Ala Gly Ser Glu Gly Thr Gly Gln Ala
1               5                   10

<210> SEQ ID NO 166
<211> LENGTH: 5
<212> TYPE: PRT
<213> ORGANISM: Homo sapiens
```

<400> SEQUENCE: 166

Met Met His Thr Ser
1               5

<210> SEQ ID NO 167
<211> LENGTH: 14
<212> TYPE: PRT
<213> ORGANISM: Homo sapiens

<400> SEQUENCE: 167

Met Met His Thr Ser Ala Gly Ala Glu Gly Ser Gly Gln Ala
1               5                   10

<210> SEQ ID NO 168
<211> LENGTH: 5
<212> TYPE: PRT
<213> ORGANISM: Homo sapiens

<400> SEQUENCE: 168

Leu Met His Thr Ala
1               5

<210> SEQ ID NO 169
<211> LENGTH: 5
<212> TYPE: PRT
<213> ORGANISM: Homo sapiens

<400> SEQUENCE: 169

Gly Gly Gly Gln Ser
1               5

<210> SEQ ID NO 170
<211> LENGTH: 14
<212> TYPE: PRT
<213> ORGANISM: Homo sapiens

<400> SEQUENCE: 170

Leu Met His Thr Ala Ala Gly Asp Glu Gly Gly Gly Gln Ser
1               5                   10

<210> SEQ ID NO 171
<211> LENGTH: 5
<212> TYPE: PRT
<213> ORGANISM: Homo sapiens

<400> SEQUENCE: 171

Leu Met His Thr Gly
1               5

<210> SEQ ID NO 172
<211> LENGTH: 5
<212> TYPE: PRT
<213> ORGANISM: Homo sapiens

<400> SEQUENCE: 172

Gly Gly Gly Gln Ala
1               5

<210> SEQ ID NO 173
<211> LENGTH: 14
<212> TYPE: PRT
<213> ORGANISM: Homo sapiens

<400> SEQUENCE: 173

```
Leu Met His Thr Gly Ala Gly Asp Gln Gly Gly Gly Gln Ala
1               5                   10
```

<210> SEQ ID NO 174
<211> LENGTH: 14
<212> TYPE: PRT
<213> ORGANISM: Homo sapiens

<400> SEQUENCE: 174

```
Leu Met His Thr Ala Ala Gly Ala Glu Gly Gly Gly Gln Ser
1               5                   10
```

<210> SEQ ID NO 175
<211> LENGTH: 12
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X stands for histidine, asparagine, glutamine, or serine.
<220> FEATURE:
<221> NAME/KEY: MISC_FEATURE
<222> LOCATION: (5)..(5)
<223> OTHER INFORMATION: X stands for glycine, arginine, alanine, or is absent.
<220> FEATURE:
<221> NAME/KEY: MISC_FEATURE
<222> LOCATION: (6)..(6)
<223> OTHER INFORMATION: X stands for arginine or glutamine.
<220> FEATURE:
<221> NAME/KEY: MISC_FEATURE
<222> LOCATION: (10)..(10)
<223> OTHER INFORMATION: X stands for asparagine or histidine.
<220> FEATURE:
<221> NAME/KEY: MISC_FEATURE
<222> LOCATION: (11)..(11)
<223> OTHER INFORMATION: X stands for phenylalanine or tyrosine.
<220> FEATURE:
<221> NAME/KEY: MISC_FEATURE
<222> LOCATION: (12)..(12)
<223> OTHER INFORMATION: X stands for phenylalanine or tyrosine.

<400> SEQUENCE: 175

```
Glu Cys Xaa Gly Xaa Xaa Gly Thr Cys Xaa Xaa Xaa
1               5                   10
```

<210> SEQ ID NO 176
<211> LENGTH: 11
<212> TYPE: PRT
<213> ORGANISM: Homo sapiens

<400> SEQUENCE: 176

```
Glu Cys His Gly Arg Gly Thr Cys Asn Tyr Tyr
1               5                   10
```

<210> SEQ ID NO 177
<211> LENGTH: 12
<212> TYPE: PRT
<213> ORGANISM: Homo sapiens

<400> SEQUENCE: 177

```
Glu Cys Asn Gly Gly Arg Gly Thr Cys His Tyr Tyr
1               5                   10
```

<210> SEQ ID NO 178
<211> LENGTH: 12
<212> TYPE: PRT
<213> ORGANISM: Homo sapiens

```
<400> SEQUENCE: 178

Glu Cys Gln Gly Arg Gln Gly Thr Cys His Phe Phe
1               5                   10

<210> SEQ ID NO 179
<211> LENGTH: 12
<212> TYPE: PRT
<213> ORGANISM: Homo sapiens

<400> SEQUENCE: 179

Glu Cys Ser Gly Ala Arg Gly Thr Cys His Tyr Phe
1               5                   10

<210> SEQ ID NO 180
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X stands for proline, serine, or alanine.
<220> FEATURE:
<221> NAME/KEY: MISC_FEATURE
<222> LOCATION: (2)..(2)
<223> OTHER INFORMATION: X stands for glutamate, aspartate, or serine.
<220> FEATURE:
<221> NAME/KEY: MISC_FEATURE
<222> LOCATION: (4)..(4)
<223> OTHER INFORMATION: X stands for leucine or valine.

<400> SEQUENCE: 180

Xaa Xaa Thr Xaa Lys
1               5

<210> SEQ ID NO 181
<211> LENGTH: 5
<212> TYPE: PRT
<213> ORGANISM: Homo sapiens

<400> SEQUENCE: 181

Pro Ser Thr Leu Lys
1               5

<210> SEQ ID NO 182
<211> LENGTH: 5
<212> TYPE: PRT
<213> ORGANISM: Homo sapiens

<400> SEQUENCE: 182

Pro Ser Thr Val Lys
1               5

<210> SEQ ID NO 183
<211> LENGTH: 5
<212> TYPE: PRT
<213> ORGANISM: Homo sapiens

<400> SEQUENCE: 183

Ser Glu Thr Leu Lys
1               5

<210> SEQ ID NO 184
<211> LENGTH: 5
<212> TYPE: PRT
<213> ORGANISM: Homo sapiens

<400> SEQUENCE: 184
```

Ala Asp Thr Leu Lys
1               5

<210> SEQ ID NO 185
<211> LENGTH: 5
<212> TYPE: PRT
<213> ORGANISM: Homo sapiens

<400> SEQUENCE: 185

Pro Asp Thr Leu Lys
1               5

<210> SEQ ID NO 186
<211> LENGTH: 5
<212> TYPE: PRT
<213> ORGANISM: Homo sapiens

<400> SEQUENCE: 186

Phe Lys Lys Pro Thr
1               5

<210> SEQ ID NO 187
<211> LENGTH: 5
<212> TYPE: PRT
<213> ORGANISM: Homo sapiens

<400> SEQUENCE: 187

Ala Gly Glu Leu Arg
1               5

<210> SEQ ID NO 188
<211> LENGTH: 15
<212> TYPE: PRT
<213> ORGANISM: Homo sapiens

<400> SEQUENCE: 188

Phe Lys Lys Pro Thr Pro Ser Thr Leu Lys Ala Gly Glu Leu Arg
1               5                   10                  15

<210> SEQ ID NO 189
<211> LENGTH: 5
<212> TYPE: PRT
<213> ORGANISM: Homo sapiens

<400> SEQUENCE: 189

Phe Arg Lys Pro Ile
1               5

<210> SEQ ID NO 190
<211> LENGTH: 5
<212> TYPE: PRT
<213> ORGANISM: Homo sapiens

<400> SEQUENCE: 190

Ala Gly Glu Leu Glu
1               5

<210> SEQ ID NO 191
<211> LENGTH: 15
<212> TYPE: PRT
<213> ORGANISM: Homo sapiens

<400> SEQUENCE: 191

Phe Arg Lys Pro Ile Pro Ser Thr Val Lys Ala Gly Glu Leu Glu

```
              1               5              10              15

<210> SEQ ID NO 192
<211> LENGTH: 5
<212> TYPE: PRT
<213> ORGANISM: Homo sapiens

<400> SEQUENCE: 192

Phe Ser Lys Pro Gln
1               5

<210> SEQ ID NO 193
<211> LENGTH: 5
<212> TYPE: PRT
<213> ORGANISM: Homo sapiens

<400> SEQUENCE: 193

Ala Gly Asp Leu Arg
1               5

<210> SEQ ID NO 194
<211> LENGTH: 15
<212> TYPE: PRT
<213> ORGANISM: Homo sapiens

<400> SEQUENCE: 194

Phe Ser Lys Pro Gln Ser Glu Thr Leu Lys Ala Gly Asp Leu Arg
1               5                  10                  15

<210> SEQ ID NO 195
<211> LENGTH: 5
<212> TYPE: PRT
<213> ORGANISM: Homo sapiens

<400> SEQUENCE: 195

Gln Gly Ser Pro Ser
1               5

<210> SEQ ID NO 196
<211> LENGTH: 5
<212> TYPE: PRT
<213> ORGANISM: Homo sapiens

<400> SEQUENCE: 196

Ala Gly Leu Ile Arg
1               5

<210> SEQ ID NO 197
<211> LENGTH: 15
<212> TYPE: PRT
<213> ORGANISM: Homo sapiens

<400> SEQUENCE: 197

Gln Gly Ser Pro Ser Ala Asp Thr Leu Lys Ala Gly Leu Ile Arg
1               5                  10                  15

<210> SEQ ID NO 198
<211> LENGTH: 5
<212> TYPE: PRT
<213> ORGANISM: Homo sapiens

<400> SEQUENCE: 198

Ser Ser Ala Pro Ala
1               5
```

```
<210> SEQ ID NO 199
<211> LENGTH: 5
<212> TYPE: PRT
<213> ORGANISM: Homo sapiens

<400> SEQUENCE: 199

Glu Ser Gln Ala Gln
1               5

<210> SEQ ID NO 200
<211> LENGTH: 15
<212> TYPE: PRT
<213> ORGANISM: Homo sapiens

<400> SEQUENCE: 200

Ser Ser Ala Pro Ala Pro Asp Thr Leu Lys Glu Ser Gln Ala Gln
1               5                   10                  15

<210> SEQ ID NO 201
<211> LENGTH: 5
<212> TYPE: PRT
<213> ORGANISM: Homo sapiens

<400> SEQUENCE: 201

Gly Glu Leu Pro Val
1               5

<210> SEQ ID NO 202
<211> LENGTH: 5
<212> TYPE: PRT
<213> ORGANISM: Homo sapiens

<400> SEQUENCE: 202

Ala Gly Gln Leu His
1               5

<210> SEQ ID NO 203
<211> LENGTH: 15
<212> TYPE: PRT
<213> ORGANISM: Homo sapiens

<400> SEQUENCE: 203

Gly Glu Leu Pro Val Ser Glu Thr Leu Lys Ala Gly Gln Leu His
1               5                   10                  15

<210> SEQ ID NO 204
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X stands for serine, glutamine, or arginine.

<400> SEQUENCE: 204

Ala Xaa Arg Asn Asp
1               5

<210> SEQ ID NO 205
<211> LENGTH: 5
<212> TYPE: PRT
<213> ORGANISM: Homo sapiens

<400> SEQUENCE: 205

Ala Ser Arg Asn Asp
```

```
<210> SEQ ID NO 206
<211> LENGTH: 5
<212> TYPE: PRT
<213> ORGANISM: Homo sapiens

<400> SEQUENCE: 206

Ala Gln Arg Asn Asp
1               5

<210> SEQ ID NO 207
<211> LENGTH: 5
<212> TYPE: PRT
<213> ORGANISM: Homo sapiens

<400> SEQUENCE: 207

Ala Arg Arg Asn Asp
1               5

<210> SEQ ID NO 208
<211> LENGTH: 5
<212> TYPE: PRT
<213> ORGANISM: Homo sapiens

<400> SEQUENCE: 208

Asn Val Cys Asn Phe
1               5

<210> SEQ ID NO 209
<211> LENGTH: 5
<212> TYPE: PRT
<213> ORGANISM: Homo sapiens

<400> SEQUENCE: 209

Tyr Ser Tyr Trp Leu
1               5

<210> SEQ ID NO 210
<211> LENGTH: 15
<212> TYPE: PRT
<213> ORGANISM: Homo sapiens

<400> SEQUENCE: 210

Asn Val Cys Asn Phe Ala Ser Arg Asn Asp Tyr Ser Tyr Trp Leu
1               5                   10                  15

<210> SEQ ID NO 211
<211> LENGTH: 5
<212> TYPE: PRT
<213> ORGANISM: Homo sapiens

<400> SEQUENCE: 211

Asp Val Cys Asn Phe
1               5

<210> SEQ ID NO 212
<211> LENGTH: 15
<212> TYPE: PRT
<213> ORGANISM: Homo sapiens

<400> SEQUENCE: 212

Asp Val Cys Asn Phe Ala Ser Arg Asn Asp Tyr Ser Tyr Trp Leu
1               5                   10                  15
```

```
<210> SEQ ID NO 213
<211> LENGTH: 5
<212> TYPE: PRT
<213> ORGANISM: Homo sapiens

<400> SEQUENCE: 213

Asp Val Cys Tyr Tyr
1               5

<210> SEQ ID NO 214
<211> LENGTH: 5
<212> TYPE: PRT
<213> ORGANISM: Homo sapiens

<400> SEQUENCE: 214

Lys Ser Tyr Trp Leu
1               5

<210> SEQ ID NO 215
<211> LENGTH: 15
<212> TYPE: PRT
<213> ORGANISM: Homo sapiens

<400> SEQUENCE: 215

Asp Val Cys Tyr Tyr Ala Ser Arg Asn Asp Lys Ser Tyr Trp Leu
1               5                   10                  15

<210> SEQ ID NO 216
<211> LENGTH: 5
<212> TYPE: PRT
<213> ORGANISM: Homo sapiens

<400> SEQUENCE: 216

Gln Val Cys His Tyr
1               5

<210> SEQ ID NO 217
<211> LENGTH: 5
<212> TYPE: PRT
<213> ORGANISM: Homo sapiens

<400> SEQUENCE: 217

Arg Ser Tyr Trp Leu
1               5

<210> SEQ ID NO 218
<211> LENGTH: 15
<212> TYPE: PRT
<213> ORGANISM: Homo sapiens

<400> SEQUENCE: 218

Gln Val Cys His Tyr Ala Gln Arg Asn Asp Arg Ser Tyr Trp Leu
1               5                   10                  15

<210> SEQ ID NO 219
<211> LENGTH: 5
<212> TYPE: PRT
<213> ORGANISM: Homo sapiens

<400> SEQUENCE: 219

Glu Val Cys His Tyr
1               5

<210> SEQ ID NO 220
```

```
<211> LENGTH: 15
<212> TYPE: PRT
<213> ORGANISM: Homo sapiens

<400> SEQUENCE: 220

Glu Val Cys His Tyr Ala Arg Arg Asn Asp Lys Ser Tyr Trp Leu
1               5                   10                  15

<210> SEQ ID NO 221
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X stands for tyrosine or phenylalanine.
<220> FEATURE:
<221> NAME/KEY: MISC_FEATURE
<222> LOCATION: (2)..(2)
<223> OTHER INFORMATION: X stands for tyrosine or phenylalanine.
<220> FEATURE:
<221> NAME/KEY: MISC_FEATURE
<222> LOCATION: (3)..(3)
<223> OTHER INFORMATION: X stands for alanine or serine.
<220> FEATURE:
<221> NAME/KEY: MISC_FEATURE
<222> LOCATION: (5)..(5)
<223> OTHER INFORMATION: X stands for alanine, serine, or lysine.

<400> SEQUENCE: 221

Xaa Xaa Xaa Asn Xaa
1               5

<210> SEQ ID NO 222
<211> LENGTH: 5
<212> TYPE: PRT
<213> ORGANISM: Homo sapiens

<400> SEQUENCE: 222

Tyr Tyr Ala Asn Ala
1               5

<210> SEQ ID NO 223
<211> LENGTH: 5
<212> TYPE: PRT
<213> ORGANISM: Homo sapiens

<400> SEQUENCE: 223

Tyr Tyr Ser Asn Ser
1               5

<210> SEQ ID NO 224
<211> LENGTH: 5
<212> TYPE: PRT
<213> ORGANISM: Homo sapiens

<400> SEQUENCE: 224

Tyr Tyr Ala Asn Ser
1               5

<210> SEQ ID NO 225
<211> LENGTH: 5
<212> TYPE: PRT
<213> ORGANISM: Homo sapiens

<400> SEQUENCE: 225

Tyr Tyr Ala Asn Lys
1               5
```

<210> SEQ ID NO 226
<211> LENGTH: 5
<212> TYPE: PRT
<213> ORGANISM: Homo sapiens

<400> SEQUENCE: 226

Phe Phe Ala Asn Lys
1               5

<210> SEQ ID NO 227
<211> LENGTH: 5
<212> TYPE: PRT
<213> ORGANISM: Homo sapiens

<400> SEQUENCE: 227

Tyr Phe Ala Asn Lys
1               5

<210> SEQ ID NO 228
<211> LENGTH: 5
<212> TYPE: PRT
<213> ORGANISM: Homo sapiens

<400> SEQUENCE: 228

Arg Gly Thr Cys Asn
1               5

<210> SEQ ID NO 229
<211> LENGTH: 5
<212> TYPE: PRT
<213> ORGANISM: Homo sapiens

<400> SEQUENCE: 229

Tyr Ser Phe Trp Leu
1               5

<210> SEQ ID NO 230
<211> LENGTH: 15
<212> TYPE: PRT
<213> ORGANISM: Homo sapiens

<400> SEQUENCE: 230

Arg Gly Thr Cys Asn Tyr Tyr Ala Asn Ala Tyr Ser Phe Trp Leu
1               5                   10                  15

<210> SEQ ID NO 231
<211> LENGTH: 15
<212> TYPE: PRT
<213> ORGANISM: Homo sapiens

<400> SEQUENCE: 231

Arg Gly Thr Cys Asn Tyr Tyr Ser Asn Ser Tyr Ser Phe Trp Leu
1               5                   10                  15

<210> SEQ ID NO 232
<211> LENGTH: 15
<212> TYPE: PRT
<213> ORGANISM: Homo sapiens

<400> SEQUENCE: 232

Arg Gly Thr Cys Asn Tyr Tyr Ala Asn Ser Tyr Ser Phe Trp Leu
1               5                   10                  15

<210> SEQ ID NO 233
<211> LENGTH: 5
<212> TYPE: PRT
<213> ORGANISM: Homo sapiens

<400> SEQUENCE: 233

Arg Gly Thr Cys His
1               5

<210> SEQ ID NO 234
<211> LENGTH: 15
<212> TYPE: PRT
<213> ORGANISM: Homo sapiens

<400> SEQUENCE: 234

Arg Gly Thr Cys His Tyr Tyr Ala Asn Lys Tyr Ser Phe Trp Leu
1               5                   10                  15

<210> SEQ ID NO 235
<211> LENGTH: 5
<212> TYPE: PRT
<213> ORGANISM: Homo sapiens

<400> SEQUENCE: 235

Gln Gly Thr Cys His
1               5

<210> SEQ ID NO 236
<211> LENGTH: 15
<212> TYPE: PRT
<213> ORGANISM: Homo sapiens

<400> SEQUENCE: 236

Gln Gly Thr Cys His Phe Phe Ala Asn Lys Tyr Ser Phe Trp Leu
1               5                   10                  15

<210> SEQ ID NO 237
<211> LENGTH: 15
<212> TYPE: PRT
<213> ORGANISM: Homo sapiens

<400> SEQUENCE: 237

Arg Gly Thr Cys His Tyr Phe Ala Asn Lys Tyr Ser Phe Trp Leu
1               5                   10                  15

<210> SEQ ID NO 238
<211> LENGTH: 11
<212> TYPE: PRT
<213> ORGANISM: Homo sapiens

<400> SEQUENCE: 238

Ile Glu Arg Ser Glu Met Phe Lys Lys Pro Thr
1               5                   10

<210> SEQ ID NO 239
<211> LENGTH: 11
<212> TYPE: PRT
<213> ORGANISM: Homo sapiens

<400> SEQUENCE: 239

Leu Asn Pro Glu Arg Met Phe Arg Lys Pro Ile
1               5                   10

<210> SEQ ID NO 240
<211> LENGTH: 11

<212> TYPE: PRT
<213> ORGANISM: Homo sapiens

<400> SEQUENCE: 240

Val Asp Val Ser Asp Met Phe Ser Lys Pro Gln
1               5                   10

<210> SEQ ID NO 241
<211> LENGTH: 11
<212> TYPE: PRT
<213> ORGANISM: Homo sapiens

<400> SEQUENCE: 241

Ile Pro Glu Gln Ser Phe Gln Gly Ser Pro Ser
1               5                   10

<210> SEQ ID NO 242
<211> LENGTH: 12
<212> TYPE: PRT
<213> ORGANISM: Homo sapiens

<400> SEQUENCE: 242

Val Lys Ala Asp Leu Gln Phe Ser Ser Ala Pro Ala
1               5                   10

<210> SEQ ID NO 243
<211> LENGTH: 12
<212> TYPE: PRT
<213> ORGANISM: Homo sapiens

<400> SEQUENCE: 243

Val Glu Glu Arg Gln Gln Phe Gly Glu Leu Pro Val
1               5                   10

<210> SEQ ID NO 244
<211> LENGTH: 5
<212> TYPE: PRT
<213> ORGANISM: Homo sapiens

<400> SEQUENCE: 244

Phe Trp Leu Ala Thr
1               5

<210> SEQ ID NO 245
<211> LENGTH: 21
<212> TYPE: PRT
<213> ORGANISM: Homo sapiens

<400> SEQUENCE: 245

Phe Trp Leu Ala Thr Ile Glu Arg Ser Glu Met Phe Lys Lys Pro Thr
1               5                   10                  15

Pro Ser Thr Leu Lys
            20

<210> SEQ ID NO 246
<211> LENGTH: 5
<212> TYPE: PRT
<213> ORGANISM: Homo sapiens

<400> SEQUENCE: 246

Phe Trp Leu Ala Ser
1               5

<210> SEQ ID NO 247

<211> LENGTH: 21
<212> TYPE: PRT
<213> ORGANISM: Homo sapiens

<400> SEQUENCE: 247

Phe Trp Leu Ala Ser Leu Asn Pro Glu Arg Met Phe Arg Lys Pro Ile
1               5                   10                  15

Pro Ser Thr Val Lys
            20

<210> SEQ ID NO 248
<211> LENGTH: 21
<212> TYPE: PRT
<213> ORGANISM: Homo sapiens

<400> SEQUENCE: 248

Phe Trp Leu Ala Thr Val Asp Val Ser Asp Met Phe Ser Lys Pro Gln
1               5                   10                  15

Ser Glu Thr Leu Lys
            20

<210> SEQ ID NO 249
<211> LENGTH: 5
<212> TYPE: PRT
<213> ORGANISM: Homo sapiens

<400> SEQUENCE: 249

Phe Trp Leu Thr Thr
1               5

<210> SEQ ID NO 250
<211> LENGTH: 21
<212> TYPE: PRT
<213> ORGANISM: Homo sapiens

<400> SEQUENCE: 250

Phe Trp Leu Thr Thr Ile Pro Glu Gln Ser Phe Gln Gly Ser Pro Ser
1               5                   10                  15

Ala Asp Thr Leu Lys
            20

<210> SEQ ID NO 251
<211> LENGTH: 22
<212> TYPE: PRT
<213> ORGANISM: Homo sapiens

<400> SEQUENCE: 251

Phe Trp Leu Thr Thr Val Lys Ala Asp Leu Gln Phe Ser Ser Ala Pro
1               5                   10                  15

Ala Pro Asp Thr Leu Lys
            20

<210> SEQ ID NO 252
<211> LENGTH: 22
<212> TYPE: PRT
<213> ORGANISM: Homo sapiens

<400> SEQUENCE: 252

Phe Trp Leu Thr Thr Val Glu Glu Arg Gln Gln Phe Gly Glu Leu Pro
1               5                   10                  15

Val Ser Glu Thr Leu Lys
            20

<210> SEQ ID NO 253
<211> LENGTH: 18
<212> TYPE: PRT
<213> ORGANISM: Homo sapiens

<400> SEQUENCE: 253

Phe Ser Thr Met Pro Phe Leu Phe Cys Asn Ile Asn Asn Val Cys Asn
1               5                   10                  15

Phe Ala

<210> SEQ ID NO 254
<211> LENGTH: 18
<212> TYPE: PRT
<213> ORGANISM: Homo sapiens

<400> SEQUENCE: 254

Phe Thr Thr Met Pro Phe Leu Phe Cys Asn Val Asn Asp Val Cys Asn
1               5                   10                  15

Phe Ala

<210> SEQ ID NO 255
<211> LENGTH: 18
<212> TYPE: PRT
<213> ORGANISM: Homo sapiens

<400> SEQUENCE: 255

Phe Ser Thr Met Pro Phe Met Phe Cys Asn Ile Asn Asn Val Cys Asn
1               5                   10                  15

Phe Ala

<210> SEQ ID NO 256
<211> LENGTH: 18
<212> TYPE: PRT
<213> ORGANISM: Homo sapiens

<400> SEQUENCE: 256

Phe Ser Thr Met Pro Phe Leu Tyr Cys Asn Pro Gly Asp Val Cys Tyr
1               5                   10                  15

Tyr Ala

<210> SEQ ID NO 257
<211> LENGTH: 18
<212> TYPE: PRT
<213> ORGANISM: Homo sapiens

<400> SEQUENCE: 257

Phe Ser Thr Leu Pro Phe Ala Tyr Cys Asn Ile His Gln Val Cys His
1               5                   10                  15

Tyr Ala

<210> SEQ ID NO 258
<211> LENGTH: 18
<212> TYPE: PRT
<213> ORGANISM: Homo sapiens

<400> SEQUENCE: 258

Phe Ser Thr Met Pro Phe Ile Tyr Cys Asn Ile Asn Glu Val Cys His
1               5                   10                  15

Tyr Ala

```
<210> SEQ ID NO 259
<211> LENGTH: 18
<212> TYPE: PRT
<213> ORGANISM: Homo sapiens

<400> SEQUENCE: 259

Pro Phe Leu Phe Cys Asn Ile Asn Asn Val Cys Asn Phe Ala Ser Arg
1               5                   10                  15

Asn Asp

<210> SEQ ID NO 260
<211> LENGTH: 18
<212> TYPE: PRT
<213> ORGANISM: Homo sapiens

<400> SEQUENCE: 260

Pro Phe Leu Phe Cys Asn Val Asn Asp Val Cys Asn Phe Ala Ser Arg
1               5                   10                  15

Asn Asp

<210> SEQ ID NO 261
<211> LENGTH: 18
<212> TYPE: PRT
<213> ORGANISM: Homo sapiens

<400> SEQUENCE: 261

Pro Phe Met Phe Cys Asn Ile Asn Asn Val Cys Asn Phe Ala Ser Arg
1               5                   10                  15

Asn Asp

<210> SEQ ID NO 262
<211> LENGTH: 18
<212> TYPE: PRT
<213> ORGANISM: Homo sapiens

<400> SEQUENCE: 262

Pro Phe Leu Tyr Cys Asn Pro Gly Asp Val Cys Tyr Tyr Ala Ser Arg
1               5                   10                  15

Asn Asp

<210> SEQ ID NO 263
<211> LENGTH: 18
<212> TYPE: PRT
<213> ORGANISM: Homo sapiens

<400> SEQUENCE: 263

Pro Phe Ala Tyr Cys Asn Ile His Gln Val Cys His Tyr Ala Gln Arg
1               5                   10                  15

Asn Asp

<210> SEQ ID NO 264
<211> LENGTH: 18
<212> TYPE: PRT
<213> ORGANISM: Homo sapiens

<400> SEQUENCE: 264

Pro Phe Ile Tyr Cys Asn Ile Asn Glu Val Cys His Tyr Ala Arg Arg
1               5                   10                  15

Asn Asp

<210> SEQ ID NO 265
```

<211> LENGTH: 22
<212> TYPE: PRT
<213> ORGANISM: Homo sapiens

<400> SEQUENCE: 265

Phe Ser Thr Met Pro Phe Leu Phe Cys Asn Ile Asn Asn Val Cys Asn
1               5                   10                  15

Phe Ala Ser Arg Asn Asp
            20

<210> SEQ ID NO 266
<211> LENGTH: 22
<212> TYPE: PRT
<213> ORGANISM: Homo sapiens

<400> SEQUENCE: 266

Phe Thr Thr Met Pro Phe Leu Phe Cys Asn Val Asp Val Cys Asn
1               5                   10                  15

Phe Ala Ser Arg Asn Asp
            20

<210> SEQ ID NO 267
<211> LENGTH: 22
<212> TYPE: PRT
<213> ORGANISM: Homo sapiens

<400> SEQUENCE: 267

Phe Ser Thr Met Pro Phe Met Phe Cys Asn Ile Asn Asn Val Cys Asn
1               5                   10                  15

Phe Ala Ser Arg Asn Asp
            20

<210> SEQ ID NO 268
<211> LENGTH: 22
<212> TYPE: PRT
<213> ORGANISM: Homo sapiens

<400> SEQUENCE: 268

Phe Ser Thr Met Pro Phe Leu Tyr Cys Asn Pro Gly Asp Val Cys Tyr
1               5                   10                  15

Tyr Ala Ser Arg Asn Asp
            20

<210> SEQ ID NO 269
<211> LENGTH: 22
<212> TYPE: PRT
<213> ORGANISM: Homo sapiens

<400> SEQUENCE: 269

Phe Ser Thr Leu Pro Phe Ala Tyr Cys Asn Ile His Gln Val Cys His
1               5                   10                  15

Tyr Ala Gln Arg Asn Asp
            20

<210> SEQ ID NO 270
<211> LENGTH: 22
<212> TYPE: PRT
<213> ORGANISM: Homo sapiens

<400> SEQUENCE: 270

Phe Ser Thr Met Pro Phe Ile Tyr Cys Asn Ile Asn Glu Val Cys His
1               5                   10                  15

Tyr Ala Arg Arg Asn Asp
            20

<210> SEQ ID NO 271
<211> LENGTH: 14
<212> TYPE: PRT
<213> ORGANISM: Homo sapiens

<400> SEQUENCE: 271

Pro Phe Ile Glu Cys His Gly Arg Gly Thr Cys Asn Tyr Tyr
1               5                   10

<210> SEQ ID NO 272
<211> LENGTH: 14
<212> TYPE: PRT
<213> ORGANISM: Homo sapiens

<400> SEQUENCE: 272

Pro Phe Leu Glu Cys His Gly Arg Gly Thr Cys Asn Tyr Tyr
1               5                   10

<210> SEQ ID NO 273
<211> LENGTH: 15
<212> TYPE: PRT
<213> ORGANISM: Homo sapiens

<400> SEQUENCE: 273

Pro Phe Ile Glu Cys Asn Gly Gly Arg Gly Thr Cys His Tyr Tyr
1               5                   10                  15

<210> SEQ ID NO 274
<211> LENGTH: 15
<212> TYPE: PRT
<213> ORGANISM: Homo sapiens

<400> SEQUENCE: 274

Pro Phe Leu Glu Cys Gln Gly Arg Gln Gly Thr Cys His Phe Phe
1               5                   10                  15

<210> SEQ ID NO 275
<211> LENGTH: 15
<212> TYPE: PRT
<213> ORGANISM: Homo sapiens

<400> SEQUENCE: 275

Pro Phe Ile Glu Cys Ser Gly Ala Arg Gly Thr Cys His Tyr Phe
1               5                   10                  15

<210> SEQ ID NO 276
<211> LENGTH: 18
<212> TYPE: PRT
<213> ORGANISM: Homo sapiens

<400> SEQUENCE: 276

Ile Glu Arg Ser Glu Met Phe Lys Lys Pro Thr Pro Ser Thr Leu Lys
1               5                   10                  15

Ala Gly

<210> SEQ ID NO 277
<211> LENGTH: 18
<212> TYPE: PRT
<213> ORGANISM: Homo sapiens

<400> SEQUENCE: 277

```
Leu Asn Pro Glu Arg Met Phe Arg Lys Pro Ile Pro Ser Thr Val Lys
1               5                   10                  15

Ala Gly
```

<210> SEQ ID NO 278
<211> LENGTH: 18
<212> TYPE: PRT
<213> ORGANISM: Homo sapiens

<400> SEQUENCE: 278

```
Val Asp Val Ser Asp Met Phe Ser Lys Pro Gln Ser Glu Thr Leu Lys
1               5                   10                  15

Ala Gly
```

<210> SEQ ID NO 279
<211> LENGTH: 18
<212> TYPE: PRT
<213> ORGANISM: Homo sapiens

<400> SEQUENCE: 279

```
Ile Pro Glu Gln Ser Phe Gln Gly Ser Pro Ser Ala Asp Thr Leu Lys
1               5                   10                  15

Ala Gly
```

<210> SEQ ID NO 280
<211> LENGTH: 19
<212> TYPE: PRT
<213> ORGANISM: Homo sapiens

<400> SEQUENCE: 280

```
Val Lys Ala Asp Leu Gln Phe Ser Ser Ala Pro Ala Pro Asp Thr Leu
1               5                   10                  15

Lys Glu Ser
```

<210> SEQ ID NO 281
<211> LENGTH: 19
<212> TYPE: PRT
<213> ORGANISM: Homo sapiens

<400> SEQUENCE: 281

```
Val Glu Glu Arg Gln Gln Phe Gly Glu Leu Pro Val Ser Glu Thr Leu
1               5                   10                  15

Lys Ala Gly
```

<210> SEQ ID NO 282
<211> LENGTH: 10
<212> TYPE: PRT
<213> ORGANISM: Homo sapiens

<400> SEQUENCE: 282

```
Gly Ser Cys Leu Arg Lys Phe Ser Thr Met
1               5                   10
```

<210> SEQ ID NO 283
<211> LENGTH: 10
<212> TYPE: PRT
<213> ORGANISM: Homo sapiens

<400> SEQUENCE: 283

```
Gly Ser Cys Leu Gln Arg Phe Thr Thr Met
1               5                   10
```

```
<210> SEQ ID NO 284
<211> LENGTH: 10
<212> TYPE: PRT
<213> ORGANISM: Homo sapiens

<400> SEQUENCE: 284

Gly Ser Cys Leu Arg Arg Phe Ser Thr Met
1               5                   10

<210> SEQ ID NO 285
<211> LENGTH: 10
<212> TYPE: PRT
<213> ORGANISM: Homo sapiens

<400> SEQUENCE: 285

Gly Ser Cys Leu Ala Arg Phe Ser Thr Met
1               5                   10

<210> SEQ ID NO 286
<211> LENGTH: 10
<212> TYPE: PRT
<213> ORGANISM: Homo sapiens

<400> SEQUENCE: 286

Gly Ser Cys Leu Pro Val Phe Ser Thr Leu
1               5                   10

<210> SEQ ID NO 287
<211> LENGTH: 10
<212> TYPE: PRT
<213> ORGANISM: Homo sapiens

<400> SEQUENCE: 287

Gly Ser Cys Leu Pro Arg Phe Ser Thr Met
1               5                   10

<210> SEQ ID NO 288
<211> LENGTH: 20
<212> TYPE: PRT
<213> ORGANISM: Homo sapiens

<400> SEQUENCE: 288

Leu Arg Lys Phe Ser Thr Met Pro Phe Leu Phe Cys Asn Ile Asn Asn
1               5                   10                  15

Val Cys Asn Phe
            20

<210> SEQ ID NO 289
<211> LENGTH: 20
<212> TYPE: PRT
<213> ORGANISM: Homo sapiens

<400> SEQUENCE: 289

Leu Gln Arg Phe Thr Thr Met Pro Phe Leu Phe Cys Asn Val Asn Asp
1               5                   10                  15

Val Cys Asn Phe
            20

<210> SEQ ID NO 290
<211> LENGTH: 20
<212> TYPE: PRT
<213> ORGANISM: Homo sapiens

<400> SEQUENCE: 290
```

```
Leu Arg Arg Phe Ser Thr Met Pro Phe Met Phe Cys Asn Ile Asn Asn
1               5                   10                  15

Val Cys Asn Phe
            20

<210> SEQ ID NO 291
<211> LENGTH: 20
<212> TYPE: PRT
<213> ORGANISM: Homo sapiens

<400> SEQUENCE: 291

Leu Ala Arg Phe Ser Thr Met Pro Phe Leu Tyr Cys Asn Pro Gly Asp
1               5                   10                  15

Val Cys Tyr Tyr
            20

<210> SEQ ID NO 292
<211> LENGTH: 20
<212> TYPE: PRT
<213> ORGANISM: Homo sapiens

<400> SEQUENCE: 292

Leu Pro Val Phe Ser Thr Leu Pro Phe Ala Tyr Cys Asn Ile His Gln
1               5                   10                  15

Val Cys His Tyr
            20

<210> SEQ ID NO 293
<211> LENGTH: 20
<212> TYPE: PRT
<213> ORGANISM: Homo sapiens

<400> SEQUENCE: 293

Leu Pro Arg Phe Ser Thr Met Pro Phe Ile Tyr Cys Asn Ile Asn Glu
1               5                   10                  15

Val Cys His Tyr
            20

<210> SEQ ID NO 294
<211> LENGTH: 4
<212> TYPE: PRT
<213> ORGANISM: Homo sapiens

<400> SEQUENCE: 294

Leu Arg Lys Phe
1

<210> SEQ ID NO 295
<211> LENGTH: 4
<212> TYPE: PRT
<213> ORGANISM: Homo sapiens

<400> SEQUENCE: 295

Leu Ala Arg Phe
1

<210> SEQ ID NO 296
<211> LENGTH: 2
<212> TYPE: PRT
<213> ORGANISM: Homo sapiens

<400> SEQUENCE: 296
```

```
Gln Asp
 1

<210> SEQ ID NO 297
<211> LENGTH: 3
<212> TYPE: PRT
<213> ORGANISM: Homo sapiens

<400> SEQUENCE: 297

Asn Tyr Tyr
 1

<210> SEQ ID NO 298
<211> LENGTH: 10
<212> TYPE: PRT
<213> ORGANISM: Homo sapiens

<400> SEQUENCE: 298

Phe Cys Asn Val Asn Asp Val Cys Asn Phe
 1               5                  10

<210> SEQ ID NO 299
<211> LENGTH: 10
<212> TYPE: PRT
<213> ORGANISM: Homo sapiens

<400> SEQUENCE: 299

Tyr Cys Asn Pro Gly Asp Val Cys Tyr Tyr
 1               5                  10

<210> SEQ ID NO 300
<211> LENGTH: 10
<212> TYPE: PRT
<213> ORGANISM: Homo sapiens

<400> SEQUENCE: 300

Tyr Cys Asn Ile His Gln Val Cys His Tyr
 1               5                  10

<210> SEQ ID NO 301
<211> LENGTH: 10
<212> TYPE: PRT
<213> ORGANISM: Homo sapiens

<400> SEQUENCE: 301

Tyr Cys Asn Ile Asn Glu Val Cys His Tyr
 1               5                  10

<210> SEQ ID NO 302
<211> LENGTH: 229
<212> TYPE: PRT
<213> ORGANISM: Homo sapiens
<220> FEATURE:
<221> NAME/KEY: misc_feature
<223> OTHER INFORMATION: alpha 1 chain

<400> SEQUENCE: 302

Ser Val Asp His Gly Phe Leu Val Thr Arg His Ser Gln Thr Ile Asp
 1               5                  10                  15

Asp Pro Gln Cys Pro Ser Gly Thr Lys Ile Leu Tyr His Gly Tyr Ser
                20                  25                  30

Leu Leu Tyr Val Gln Gly Asn Glu Arg Ala His Gly Gln Asp Leu Gly
            35                  40                  45

Thr Ala Gly Ser Cys Leu Arg Lys Phe Ser Thr Met Pro Phe Leu Phe
```

```
                50                  55                  60
Cys Asn Ile Asn Asn Val Cys Asn Phe Ala Ser Arg Asn Asp Tyr Ser
 65                  70                  75                  80

Tyr Trp Leu Ser Thr Pro Glu Pro Met Pro Met Ser Met Ala Pro Ile
                 85                  90                  95

Thr Gly Glu Asn Ile Arg Pro Phe Ile Ser Arg Cys Ala Val Cys Glu
                100                 105                 110

Ala Pro Ala Met Val Met Ala Val His Ser Gln Thr Ile Gln Ile Pro
                115                 120                 125

Pro Cys Pro Ser Gly Trp Ser Ser Leu Trp Ile Gly Tyr Ser Phe Val
130                 135                 140

Met His Thr Ser Ala Gly Ala Glu Gly Ser Gly Gln Ala Leu Ala Ser
145                 150                 155                 160

Pro Gly Ser Cys Leu Glu Glu Phe Arg Ser Ala Pro Phe Ile Glu Cys
                165                 170                 175

His Gly Arg Gly Thr Cys Asn Tyr Tyr Ala Asn Ala Tyr Ser Phe Trp
                180                 185                 190

Leu Ala Thr Ile Glu Arg Ser Glu Met Phe Lys Lys Pro Thr Pro Ser
                195                 200                 205

Thr Leu Lys Ala Gly Glu Leu Arg Thr His Val Ser Arg Cys Gln Val
    210                 215                 220

Cys Met Arg Arg Thr
225

<210> SEQ ID NO 303
<211> LENGTH: 227
<212> TYPE: PRT
<213> ORGANISM: Homo sapiens
<220> FEATURE:
<221> NAME/KEY: misc_feature
<223> OTHER INFORMATION: alpha 2 chain

<400> SEQUENCE: 303

Val Ser Ile Gly Tyr Leu Leu Val Lys His Ser Gln Thr Asp Gln Glu
  1               5                  10                  15

Pro Met Cys Pro Val Gly Met Asn Lys Leu Trp Ser Gly Tyr Ser Leu
                 20                  25                  30

Leu Tyr Phe Glu Gly Gln Glu Lys Ala His Asn Gln Asp Leu Gly Leu
             35                  40                  45

Ala Gly Ser Cys Leu Ala Arg Phe Ser Thr Met Pro Phe Leu Tyr Cys
 50                  55                  60

Asn Pro Gly Asp Val Cys Tyr Tyr Ala Ser Arg Asn Asp Lys Ser Tyr
 65                  70                  75                  80

Trp Leu Ser Thr Thr Ala Pro Leu Pro Met Met Pro Val Ala Glu Asp
                 85                  90                  95

Glu Ile Lys Pro Tyr Ile Ser Arg Cys Ser Val Cys Glu Ala Pro Ala
                100                 105                 110

Ile Ala Ile Ala Val His Ser Gln Asp Val Ser Ile Pro His Cys Pro
                115                 120                 125

Ala Gly Trp Arg Ser Leu Trp Ile Gly Tyr Ser Phe Leu Met His Thr
                130                 135                 140

Ala Ala Gly Asp Glu Gly Gly Gly Gln Ser Leu Val Ser Pro Gly Ser
145                 150                 155                 160

Cys Leu Glu Asp Phe Arg Ala Thr Pro Phe Ile Glu Cys Asn Gly Gly
                165                 170                 175
```

```
Arg Gly Thr Cys His Tyr Tyr Ala Asn Lys Tyr Ser Phe Trp Leu Thr
            180                 185                 190

Thr Ile Pro Glu Gln Ser Phe Gln Gly Ser Pro Ser Ala Asp Thr Leu
            195                 200                 205

Lys Ala Gly Leu Ile Arg Thr His Ile Ser Arg Cys Gln Val Cys Met
            210                 215                 220

Lys Asn Leu
225

<210> SEQ ID NO 304
<211> LENGTH: 232
<212> TYPE: PRT
<213> ORGANISM: Homo sapiens
<220> FEATURE:
<221> NAME/KEY: misc_feature
<223> OTHER INFORMATION: alpha 3 chain

<400> SEQUENCE: 304

Ala Thr Trp Thr Thr Arg Gly Phe Val Phe Thr Arg His Ser Gln Thr
1               5                   10                  15

Thr Ala Ile Pro Ser Cys Pro Glu Gly Thr Val Pro Leu Tyr Ser Gly
            20                  25                  30

Phe Ser Phe Leu Phe Val Gln Gly Asn Gln Arg Ala His Gly Gln Asp
        35                  40                  45

Leu Gly Thr Leu Gly Ser Cys Leu Gln Arg Phe Thr Thr Met Pro Phe
    50                  55                  60

Leu Phe Cys Asn Val Asn Asp Val Cys Asn Phe Ala Ser Arg Asn Asp
65                  70                  75                  80

Tyr Ser Tyr Trp Leu Ser Thr Pro Ala Leu Met Pro Met Asn Met Ala
                85                  90                  95

Pro Ile Thr Gly Arg Ala Leu Glu Pro Tyr Ile Ser Arg Cys Thr Val
            100                 105                 110

Cys Glu Gly Pro Ala Ile Ala Ile Ala Val His Ser Gln Thr Thr Asp
            115                 120                 125

Ile Pro Pro Cys Pro His Gly Trp Ile Ser Leu Trp Lys Gly Phe Ser
        130                 135                 140

Phe Ile Met Phe Thr Ser Ala Gly Ser Glu Gly Ala Gly Gln Ala Leu
145                 150                 155                 160

Ala Ser Pro Gly Ser Cys Leu Glu Glu Phe Arg Ala Ser Pro Phe Leu
                165                 170                 175

Glu Cys His Gly Arg Gly Thr Cys Asn Tyr Tyr Ser Asn Ser Tyr Ser
            180                 185                 190

Phe Trp Leu Ala Ser Leu Asn Pro Glu Arg Met Phe Arg Lys Pro Ile
            195                 200                 205

Pro Ser Thr Val Lys Ala Gly Glu Leu Glu Lys Ile Ile Ser Arg Cys
        210                 215                 220

Gln Val Cys Met Lys Lys Arg His
225                 230

<210> SEQ ID NO 305
<211> LENGTH: 231
<212> TYPE: PRT
<213> ORGANISM: Homo sapiens
<220> FEATURE:
<221> NAME/KEY: misc_feature
<223> OTHER INFORMATION: alpha 4 chain

<400> SEQUENCE: 305
```

```
Pro Gly Tyr Leu Gly Phe Leu Leu Val Leu His Ser Gln Thr Asp
1               5                   10                  15

Gln Glu Pro Thr Cys Pro Leu Gly Met Pro Arg Leu Trp Thr Gly Tyr
            20                  25                  30

Ser Leu Leu Tyr Leu Glu Gly Gln Glu Lys Ala His Asn Gln Asp Leu
            35                  40                  45

Gly Leu Ala Gly Ser Cys Leu Pro Val Phe Ser Thr Leu Pro Phe Ala
50                  55                  60

Tyr Cys Asn Ile His Gln Val Cys His Tyr Ala Gln Arg Asn Asp Arg
65                  70                  75                  80

Ser Tyr Trp Leu Ala Ser Ala Pro Leu Pro Met Met Pro Leu Ser
                85                  90                  95

Glu Glu Ala Ile Arg Pro Tyr Val Ser Arg Cys Ala Val Cys Glu Ala
                100                 105                 110

Pro Ala Gln Ala Val Ala Val His Ser Gln Asp Gln Ser Ile Pro Pro
            115                 120                 125

Cys Pro Gln Thr Trp Arg Ser Leu Trp Ile Gly Tyr Ser Phe Leu Met
130                 135                 140

His Thr Gly Ala Gly Asp Gln Gly Gly Gly Ala Leu Met Ser Pro
145                 150                 155                 160

Gly Ser Cys Leu Glu Asp Phe Arg Ala Ala Pro Phe Leu Glu Cys Gln
                165                 170                 175

Gly Arg Gln Gly Thr Cys His Phe Phe Ala Asn Lys Tyr Ser Phe Trp
            180                 185                 190

Leu Thr Thr Val Lys Ala Asp Leu Gln Phe Ser Ser Ala Pro Ala Pro
            195                 200                 205

Asp Thr Leu Lys Glu Ser Gln Ala Gln Arg Gln Lys Ile Ser Arg Cys
            210                 215                 220

Gln Val Cys Val Lys Tyr Ser
225                 230

<210> SEQ ID NO 306
<211> LENGTH: 229
<212> TYPE: PRT
<213> ORGANISM: Homo sapiens
<220> FEATURE:
<221> NAME/KEY: misc_feature
<223> OTHER INFORMATION: alpha 5 chain

<400> SEQUENCE: 306

Ser Val Ala His Gly Phe Leu Ile Thr Arg His Ser Gln Thr Thr Asp
1               5                   10                  15

Ala Pro Gln Cys Pro Gln Gly Thr Leu Gln Val Tyr Glu Gly Phe Ser
            20                  25                  30

Leu Leu Tyr Val Gln Gly Asn Lys Arg Ala His Gly Gln Asp Leu Gly
            35                  40                  45

Thr Ala Gly Ser Cys Leu Arg Arg Phe Ser Thr Met Pro Phe Met Phe
50                  55                  60

Cys Asn Ile Asn Asn Val Cys Asn Phe Ala Ser Arg Asn Asp Tyr Ser
65                  70                  75                  80

Tyr Trp Leu Ser Thr Pro Glu Pro Met Pro Met Ser Met Gln Pro Leu
            85                  90                  95

Lys Gly Gln Ser Ile Gln Pro Phe Ile Ser Arg Cys Ala Val Cys Glu
            100                 105                 110

Ala Pro Ala Val Val Ile Ala Val His Ser Gln Thr Ile Gln Ile Pro
            115                 120                 125
```

```
His Cys Pro Gln Gly Trp Asp Ser Leu Trp Ile Gly Tyr Ser Phe Met
    130                 135                 140

Met His Thr Ser Ala Gly Ala Glu Gly Ser Gly Gln Ala Leu Ala Ser
145                 150                 155                 160

Pro Gly Ser Cys Leu Glu Glu Phe Arg Ser Ala Pro Phe Ile Glu Cys
                165                 170                 175

His Gly Arg Gly Thr Cys Asn Tyr Tyr Ala Asn Ser Tyr Ser Phe Trp
            180                 185                 190

Leu Ala Thr Val Asp Val Ser Asp Met Phe Ser Lys Pro Gln Ser Glu
        195                 200                 205

Thr Leu Lys Ala Gly Asp Leu Arg Thr Arg Ile Ser Arg Cys Gln Val
    210                 215                 220

Cys Met Lys Arg Thr
225

<210> SEQ ID NO 307
<211> LENGTH: 228
<212> TYPE: PRT
<213> ORGANISM: Homo sapiens
<220> FEATURE:
<221> NAME/KEY: misc_feature
<223> OTHER INFORMATION: alpha 6 chain

<400> SEQUENCE: 307

Met Arg Val Gly Tyr Thr Leu Val Lys His Ser Gln Ser Glu Gln Val
1               5                   10                  15

Pro Pro Cys Pro Ile Gly Met Ser Gln Leu Trp Val Gly Tyr Ser Leu
            20                  25                  30

Leu Phe Val Glu Gly Gln Glu Lys Ala His Asn Gln Asp Leu Gly Phe
        35                  40                  45

Ala Gly Ser Cys Leu Pro Arg Phe Ser Thr Met Pro Phe Ile Tyr Cys
    50                  55                  60

Asn Ile Asn Glu Val Cys His Tyr Ala Arg Arg Asn Asp Lys Ser Tyr
65                  70                  75                  80

Trp Leu Ser Thr Thr Ala Pro Ile Pro Met Met Pro Val Ser Gln Thr
                85                  90                  95

Gln Ile Pro Gln Tyr Ile Ser Arg Cys Ser Val Cys Glu Ala Pro Ser
            100                 105                 110

Gln Ala Ile Ala Val His Ser Gln Asp Ile Thr Ile Pro Gln Cys Pro
        115                 120                 125

Leu Gly Trp Arg Ser Leu Trp Ile Gly Tyr Ser Phe Leu Met His Thr
    130                 135                 140

Ala Ala Gly Ala Glu Gly Gly Gln Ser Leu Val Ser Pro Gly Ser
145                 150                 155                 160

Cys Leu Glu Asp Phe Arg Ala Thr Pro Phe Ile Glu Cys Ser Gly Ala
                165                 170                 175

Arg Gly Thr Cys His Tyr Phe Ala Asn Lys Tyr Ser Phe Trp Leu Thr
            180                 185                 190

Thr Val Glu Glu Arg Gln Gln Phe Gly Glu Leu Pro Val Ser Glu Thr
        195                 200                 205

Leu Lys Ala Gly Gln Leu His Thr Arg Val Ser Arg Cys Gln Val Cys
    210                 215                 220

Met Lys Ser Leu
225
```